United States Patent [19]
Zannis et al.

[11] Patent Number: 5,877,009
[45] Date of Patent: Mar. 2, 1999

[54] ISOLATED APOA-I GENE REGULATORY SEQUENCE ELEMENTS

[75] Inventors: Vassilis I. Zannis, Newton; Christos Cladaras, Needham, both of Mass.

[73] Assignee: Trustees of Boston University, Boston, Mass.

[21] Appl. No.: 174,672

[22] Filed: Dec. 28, 1993

Related U.S. Application Data

[63] Continuation-in-part of Ser. No. 746,332, Aug. 16, 1991, abandoned.
[51] Int. Cl.[6] .......................... C12N 15/63; C12N 15/11
[52] U.S. Cl. .................................. 435/320.1; 536/24.1
[58] Field of Search ................................. 536/24.1, 23.1; 435/320.1

[56] References Cited

PUBLICATIONS

Kinya Ogami et al., "Purification and Characterization of a Heat Stable Nuclear Factor CIIIB1 Involved in the Regulation of the Human ApoC–III Gene", The Journal of Biological Chemistry, vol. 266, No. 15, Issue of May 25, pp. 9640–9646, 1991.

Jean Chambaz et al., "Promoter Elements and Factors Required for Hepatic Transcription of the Human ApoA–II Gene" The Journal of Biological Chemistry, vol. 266, No. 18, Issue of Jun. 25, pp. 11676–11685, 1991.

Philippe Cardot et al., "Regulation of the Human ApoA–II Gene by Synergistic Action of Factors Binding to the Proximal and Distal Regulatory Elements", The Journal of Biological Chemistry, vol. 266, No. 36, Issue of Dec. 25, pp. 24460–24470, 1991.

Dimitris Kardassis et al, "Organization of the Regulatory Elements and Nuclear Activities Participating in the Transcription of the Human Apolipoprotein B Gene", The Journal of Biological Chemistry, vol. 267, No. 4, Issue of Feb. 5, pp. 2662–2632, 1992.

Panagiota Papazafiri et al., "Promoter Elements and Factor Involved in Hepatic Transcription of the Human Apo–A–I Gene Positive and Negative Regulators Bind to Overlapping Sites", The Journal of Biological Chemistry, vol. 266, No. 9, Issue of Mar. 25, pp. 5790–5797, 1991.

Dimitris Kardassis et al., "Purification and Characterization of the Nuclear Factor BA1", The Journal of Biological Chemistry, vol. 265, No. 35, Issue of Dec. 15, pp. 21733–21740, 1990.

Philippe Cardot et al., "Factors Participating in the Liver–Specific Expression of the Human Apolipoprotein A–II Gene and Their Significance for Transcription", Biochemistry, vol. 32, pp. 9080–9093, 1993.

Vassilis I. Zannis et al., "Molecular biology of the human apolipoprotein genes: gene regulation and structure/function relationship", Current Opinion in Lipidology, vol. 3, pp. 96–113, 1992.

Jean Chambaz et al., "Promoter Elements and Factors Required for Hepatic Transcription of the Human Apo A–II Gene", Circulation, 82, 532, 1990.

Kinya Ogami et al., "Purification and Characterization of the Heat Stable Nuclear Factor (C111b1) Regulating the Human Apo C–III Gene Transcription", Circulation, 82, 532, 1990.

Panagiota Papazafiri et al., "Hepatic Factors Regulating the Transcription of the Human Apo A–I Gene", Circulation, 82, 532, 1990.

Elizabeth M. Hardon et al., "Two distinct factors interact with the promoter regions of several liver–specific genes", The EMBO Journal, vol. 7, No. 6, pp. 1711–1719, 1988.

Shula Metzger, "Nuclear Factors AF–1 and C/EBP Bind to the Human ApoB Gene Promoter and Modulate its Transcriptional Activity in Hepatic Cells", The Journal of Biological Chemistry, vol. 265, No. 17, Issue of Jun. 15, pp. 9978–9983, 1990.

Hriday K. Das, "Cell Type–specific Expression of the Human ApoB Gene is Controlled by Two cis–acting Regulatory Regions", The Journal of Biological Chemistry, vol. 263, No. 23, Issue of Aug. 15, pp. 11452–11458, 1988.

Dimitris Kardassis et al., "Characterization of the Promoter Elements Required for Hepatic and Intestinal Transcription of the Human apoB Gene: Definition of the DNA–Binding Site of a Tissue–Specific Transcriptional Factor", Molecular and Cellular Biology, vol. 10, No. 6, pp. 2653–2659, Jun. 1990.

Miguel A. Lucero et al., "Interaction of DNA–binding proteins with the tissue–specific human apolipoprotein–AII enhancer", vol. 17, No. 6, pp. 2283–2300, 1989.

Ladias J.A.A. et al., "Transcriptional Regulation of Human Apolipoprotein Genes ApoB, ApoCIII, and ApoAII by members of the steroid hormone receptor superfamily HNF–4, ARP–1, EAR–2, and EAR–3", J. Biol. Chem. 267:15849–15860, 1992.

Paulweber, B. et al., "Identification of a Negative Regulatory Region '5 of the Human Apolipoprotein B Promoter", J. Biol. Chem. 266: 11057–10074, 1991.

Paulweber, B. et al., "The Mechanism by the Human Apolipoprotein B Gene Reducer Operates Involves Blocking of Transcriptional Activation by Hepatocyte Nuclear Factor 3". Mol. Cell. Biol. 13:1534–1546, 1993.

(List continued on next page.)

*Primary Examiner*—Terry McKelvey
*Attorney, Agent, or Firm*—Brenda Herschbach Jarrell; Sam Pasternack; Choate, Hall & Stewart

[57] ABSTRACT

The present invention provides isolated apolipoprotein transcription factors and gene regulatory elements. The invention also provides methods of modulating apolipoprotein gene expression by interfering with interactions between apolipoprotein transcription factors and their cognate regulatory elements and/or by interfering with protein-protein interactions between or among apolipoprotein transcription factors or between an apolipoprotein transcription factor and the transcription machinery. This invention has application in the treatment of disorders relating to lipid metabolism (e.g. atherosclerosis, hypertriglyceridemia, etc.).

10 Claims, 11 Drawing Sheets

OTHER PUBLICATIONS

Rottman, J.N. et al., "A Retinoic Acid–Responsive Element in the Apolipoprotein A–I Gene Distinguishes Between Two Different Retinoic Acid Responsive Pathways", Mol. Cell. Biol. 11:3814–3820, 1991.

Sladek, F.M. et al., "Liver Enriched Transcription Factor HNF–4 is a Novel Member of the Steroid Hormone Receptor Superfamily", Genes Dev. 2353, 1990.

Michele Mietus–Snyder et al., "Antagonism between Apolipoprotein AI Regulatory Protein 1, Ear3/COUP–TF, and Hepatocyte Nuclear Factor 4 Modulates Apolipoprotein CIII Gene Expression in Liver and Intestinal Cell", Molecular and Cellular Biology, vol. 12, No. 4, pp. 1708–1718, Apr., 1992.

Widom, R.L. et al., "Synergistic Interactions Between Transcription Factors Control Expression of the Apolipoprotein A–I Gene in Liver Cells", Mol. Cell. Biol. 11:677–687, 1991.

Higuchi et al, J. of Biological Chemistry, Dec. 5, 1988, vol. 263 (34):pp. 18530–18536.

(a)

-911 AAGCTTCTGATATCTATTTAACTGATTTCACCCAAATGCTTTGAACCTGGGAATGTACTTCTCCCCACCCCCAACAGGAGTGAGACAAGGCCAGGCTATTGCCCCTGTGACTCAATATTGG

-903   N   -879                                -853  M  -829          -803  L

-781 CTAATCACTCCCTAGAACTGATAAGGTCATCAAATGACCAGGTGCCTTCAACCTTTACCCTGGTAGAAGCCTCTTATTCACCTCTTTTCCTGCCAGAGCCCTCCATTGGGAGGACGGGCGGAAGTGTTTC

-773                         -760 K -743       -734  J  -716     -706        I              -680

DISTAL REGION

-649 TGAATTTGTTTTACTGGGGTAGGGTATGTCAGTGATGATCAGCATCCAGGTCTCCTCCCCGTCTCATTACTACATTAACTCAAAAAGGACAAGATCATTTACACTTGCCCTCTTACCC

-573  H   -554

-514 GACCCTCATTCCCCTAACCCCATAGCCTGTCCCTGATTTCAATTCCTTTCCCTTTCTCTCCCAATATCCTCTGCCAAGTTGCAGTAAGTGGGATAAGGTTGAGAGATGAGATCTAC

-468 G -455                                     -404 F -384

-381 CCATAATGGAATAAAGACACCAGAGCTTTCCATGGTATGGGTTGATATGTCAGCTTCCAGACGAAATAACTTGGAATCCTGCTTCCTGTTGCATTCAAGTCAAGGACC

-377 E -364                                      -276 D -255

MIDDLE REGION

-248 TCAGATCTCAAAAGAATGAACCTCAAATATACCTGAAGTGTACCCCTTAGCCTCACTAGAGAGCTGTACCCTGCCTCTCCACCCCATCACCATCAGTGTCTTCCATGCTGTTGCTCCTCCTCCCCATTTC

-126 C

-116 TCCAACTTGTTTTATCCTCACATAATCCCTGCCCACTGGGCCCATCCATAGTCCTGTCACCTGTCATGACAGTCCTGACAGGGGTGGGTAAACAGACAGGTATATAGCCCCTTTCCCTCTCCAGCCAGGGGCAGGCAGGCACAGACACCA

-110                                        -65     B       -42 -40 A -33

PROXIMAL REGION

+15 AGGACAGAGACGCTG

| FIG. 2A |
| FIG. 2B |

AAGCCAG TGTAGAAACCAA CAGG TCAGGCCC CGGGAGGGCCCTT TGGACCTTTTG CAATCCTG GCGCTCTTGCAGCCTGGGCTT-//-TCTCGGTTGCTGCCGCTGAGG

-118 Element I -98

-112 Element II -94

-86 Element III -62

-72 Element IV -53

Element V -33

+33 Element E +52

```
-1411  GAATTCTGAGGGCAGAGAGCGGGCCACTTTCTCAGGCCCTCTGATTTCATACTGTGTGGTGTTAGTTACTTC
-1344  TGAGAGGACAGCTTGCGCCAGAGCTTCTATTTTTTATGTTAGAGGCTCCTCCTTCTGCCTGCAGACTCTG
-1278  CTGTCTGGGAAGGGCACAGCGTTAGGAGGAGAGGAGGTGTGAGTCCCTCCGTGACCCGCTG
-1214  CTTTGTACTTCTCTATCTCATTTCCTTTTCAGCACCACTCTGGGAAATCAGTATTCCAGCCCCATTT
-1147  TATCCTCAGAAAATTCAGGTCTCTGAGATGTTATCTGTGACCTGGGTCCTATTACGTGCCAAAGG
-1081  CATCATTTAAGCCTAAGATGTCCTGGCTCCAAGGTGTCAGCATCTGGAAGACAGGCGCCCTCAT
-1017  CCTGCCATCCTGCTGCTTCACTGTGGGCCCAGAACTCCTCTGTGCCCTCTCAGCCCCGAGAAGGTCAG
-954   CGGCCCCTCCTGGACTCCCACCGCCCCCAGGGGCCAGGGACATCTCAGCCCCTCCTCACCAGACCTT
-891   GTTCCTCCCAGTTGCTCCCACAGCCAGGGGCAGTGAGGGCTGCTCTTCCCCAGCCCCACTG
-828   AGGAACCCAGGAAGGTGAACGAGAGAATCAGTCCTGGTGGGGCTGGGGAGGGCCCRGACAT
-766   GAGACCAGCTCCTCCCCCAGGGATGTTATCAGTGGGTCCAGAGGGCAAAATAGGAGCCTGGT
-703   GGAGGGAGGGCAAAGGCCTCGGGCTCTGAGCGGCCTTGGCTTCTCCACCAACCCCTGCCCT
-641   ACACTCAGGGGAGGGGAGGGCACACAGGGTGGGGCGGGTGGGGGCTGGGTG
-579   AGCAGCACTCGCCTGCCTGGATTGAAACCCAGAGAGATGAGGTGCTGGGAGGGCTGTGAGAGC
-516   TCAGCCCTGTAACCAGGCCTTGCGAGCCACTGATGCCCGGTTCTTCTGTGCCTTTACTCCAAACRT
-451   CCCCCAGCCCAGCACCCACTTGTTCTCAAGTCTGGAGGGCCTGAAGAAGCCCCTACCCCTCTACTCCAGG
-387   CTGTGTTCAGGGCTTGGGGCTGGTGGAGGGGCCTGAAATTCCAGTGTGAAAGGCTGAGATG
-322   GGCCCCAGCCCTGGCCTATGTCCAAGCCATTCCCCTCCCAGCCCTCTCCCTGGGAGCCAG
-258   TCAGCTAGGAAGGAATGAGGCTCCCCAGGCCTCCCCCACCCCCAGTTCCTAGGCTGCTGCAG
-194   GGCTGGCGGGACAGCAGCGTGGGACTCAGTCTCAGGGATTTCCCAACTCTCCCGCCCGTTGC
-130   TGCATCTGGACACCCTCAGGCCCTGCTCCCTCATCTCCACTGGTCAGCAGGTCAGCCTTTGCCCAGCG
-66    CCCTGGGTCCTCAGTGCCTGCCCCCTGGAGATGATATAAAACAGGTCAGAACCCCTCCTGCCTG
-2     TCTGCTCAGTTCATCCCTAGAGGCAG
```

ISOLATED APOA-I GENE REGULATORY SEQUENCE ELEMENTS

The present application is a Continuation-in-Part of application Ser. No. 07/746,332, filed Aug. 16, 1991, now abandonded. The entire contents of Ser. No. 08/746,332 are incorporated herein by reference.

This invention was made in the course of work supported in part by United States Government funds (grants number HL 33952 and number HL 43909), and the Government has certain rights to the invention.

BACKGROUND OF THE INVENTION

Lipoproteins are macromolecular complexes of lipids and proteins that are involved in the transport and distribution of dietary and/or endogenously synthesized lipids (e.g. cholesterol, triglycerides, and phospholipids) in the body. Plasma lipoproteins have traditionally been grouped in four major lipoprotein classes: Chylomicrons, very low density lipoproteins (VLDL), low-density lipoproteins (LDL), and high density lipoproteins (HDL).

The protein components of lipoproteins are called apolipoproteins and have been designated apoA-I, apoA-II, apoA-IV, apoB, apoCI, apoCII, apoCIII, and apoE. The biological roles played by each of these apolipoproteins in lipoprotein function and metabolism, and therefore in lipid transport and distribution, are being defined. Studies have revealed that genetic changes which alter either the function or the plasma concentration of any of these apolipoproteins can perturb the pathway of lipid metabolism and may directly or indirectly contribute to the pathogenesis of atherosclerosis and other disorders.

The plasma concentration of apolipoproteins may be altered by changes in the level of apolipoprotein gene transcription. Thus, it is important to understand the molecular mechanisms responsible for modulating apolipoprotein gene expression.

Gene transcription in eukaryotes is controlled by the interaction of nuclear proteins (transcription factors) with specific nucleotide sequences (regulatory elements, enhancers, silencers, etc.). Such interactions direct tissue-specific gene expression, gene expression during differentiation and development, and gene expression in response to intracellular and extracellular stimuli such as hormones and metabolites. Transcriptional regulatory elements are often found in front of (upstream) of genes, but can also be located within, or even downstream of, genes. In some cases, important transcriptional regulatory sequences that control tissue-specific or developmentally-regulated gene expression are located very far away, perhaps several kilobases, from the gene they regulate.

Studies of the transcriptional regulation of a gene (or genes) of interest often begin with DNA mapping analyses (e.g. DNase I protection studies or deletion analyses coupled with in vitro or in vivo transcription reactions) that identify broad sequence regions involved in modulating gene expression. However, identification of the exact protein factors and regulatory sequences involved, which is necessary for full understanding of the transcriptional regulation of a gene, is complicated by several realities of eukaryotic transcriptional regulation systems.

First of all, the regulatory elements recognized by different transcription factors are often adjacent or overlapping. Interactions between transcription factors bound to neighboring regulatory elements can profoundly alter the extent, or even the direction, of transcriptional regulation. In some cases, adjacent transcriptional activators can stimulate transcription synergistically, so that the increase in gene expression is greater than would be predicted by summing effects of the individual regulators. In other instances, proteins that are transcriptional activators in one regulatory context (i.e. in the presence of a particular set of neighboring regulatory factors) can function as transcriptional repressors under different circumstances (see, for example, Keleher et al. Mol. Cell. Biol. 9:5228–5230; Diamond et al. Science 249:1266–1272, 1990).

Secondly, individual regulatory sequences can often be recognized by more than one protein factor. In some cases, the different protein factors capable of binding to one regulatory element have opposite effects on gene expression. That is, both transcriptional activators and transcriptional repressors can sometimes recognize the same nucleotide sequence (see, for example Tanaka et al. Mol. Cell. Biol. 13:4531–4538, 1993).

Thirdly, some protein factors that are involved in regulating transcription from a particular promoter do not bind to regulatory elements within that promoter at all, but rather modulate gene expression by interacting with other factors that do bind to nucleotide sequence elements within that promoter.

For these and other reasons, identification and characterization of the exact regulatory elements and protein factors involved in transcriptional regulation is difficult. Such identification and characterization is required, however, for a full understanding of the transcriptional regulation of gene expression.

SUMMARY OF THE INVENTION

It is an object of the present invention to provide identification and characterization of several regulatory sequences and protein factors involved in regulating apolipoprotein gene transcription. It is a further object of the invention to provide methods for altering the expression of an apolipoprotein gene. Such regulatory sequences, protein factors, and methods may have application in the treatment of disorders relating to lipid metabolism (e.g. atherosclerosis).

According to the invention, novel, isolated, apolipoprotein transcription factors are provided that are capable of binding to a regulatory sequence element of an apolipoprotein gene promoter. In particular, one aspect of the invention relates to a novel, isolated apolipoprotein transcription factor that is capable of binding to a regulatory sequence element of an apolipoprotein A-I (apoA-I) gene promoter. In preferred embodiments, the invention provides a novel, isolated apolipoprotein transcription factor that is capable of binding to a sequence element that has a nucleotide sequence comprising a nucleotide sequence found between approximately nucleotide number –175 and nucleotide number –148 (element C; 59 to 86 of SEQ ID NO:10) of the apoA-I gene promoter; or a novel, isolated apolipoprotein transcription factor that is capable of binding to a sequence element that has a nucleotide sequence comprising a nucleotide sequence found between approximately nucleotide number –220 and nucleotide number –190 (element D; 14 to 44 of SEQ ID NO:10) of the apoA-I gene promoter.

Another aspect of the invention relates to a novel, isolated apolipoprotein transcription factor that is capable of binding to a regulatory sequence element of an apolipoprotein A-II (apoA-II) gene promoter. In preferred embodiments, the invention provides a novel, isolated apolipoprotein transcription factor that is capable of binding to a sequence element that has a nucleotide sequence comprising a nucleotide sequence found between approximately nucleotide number −65 and nucleotide number −33 (element AB; 847 to 879 of SEQ ID NO:11) of the apoA-II gene promoter; a novel, isolated apolipoprotein transcription factor that is capable of binding to a sequence element that has a nucleotide sequence comprising a nucleotide sequence found between approximately nucleotide number −276 and nucleotide number −255 (element D; 636 to 657 of SEQ ID NO:11) of the apoA-II gene promoter; a novel, isolated apolipoprotein transcription factor that is capable of binding to a sequence element that has a nucleotide sequence comprising a nucleotide sequence found between approximately nucleotide number −853 and nucleotide number −829 (element M; 59 to 83 of SEQ ID NO:11) of the apoA-II gene promoter; or a novel, isolated apolipoprotein transcription factor that is capable of binding to a sequence element that has a nucleotide sequence comprising a nucleotide sequence found between approximately nucleotide number −903 and nucleotide number −879 (element N; 9 to 33 of SEQ ID NO:11) of the apoA-II gene promoter.

Yet another aspect of the invention relates to a novel, isolated apolipoprotein transcription factor that is capable of binding to a regulatory sequence element of an apolipoprotein B (apoB) gene promoter. In preferred embodiments, the invention provides a novel, isolated apolipoprotein transcription factor that is capable of binding to a plurality of regulatory sequence elements of an apoB gene promoter, comprising a first sequence element having a nucleotide sequence comprising a nucleotide sequence found between approximately nucleotide number −118 and nucleotide number −98 (element I; 1 to 21 of SEQ ID NO:12) of the apoB gene promoter; a second sequence element having a nucleotide sequence comprising a nucleotide sequence found between approximately nucleotide number −72 and nucleotide number −53 (element IV; 47 to 66 of SEQ ID NO:12) of the apoB gene promoter; a third sequence element having a nucleotide sequence comprising a nucleotide sequence found between approximately nucleotide number −53 and nucleotide number −33 (element V; 66 to 86 of SEQ ID NO:12) of the apoB gene promoter; and a fourth sequence element having a nucleotide sequence comprising a nucleotide sequence found between approximately nucleotide number +33 and +52 (element E; SEQ ID NO:13) of the apoB gene promoter. In alternate preferred embodiments, the invention provides a novel, isolated apolipoprotein transcription factor that is capable of binding to a sequence element has a nucleotide sequence comprising a nucleotide sequence found between approximately nucleotide number −112 and nucleotide number −94 (element II; 7 to 25 of SEQ ID NO:12) of the apoB gene promoter; or a novel, isolated apolipoprotein transcription factor that is capable of binding to a sequence element that has a nucleotide sequence comprising a nucleotide sequence found between approximately nucleotide number −86 and nucleotide sequence number −62 (element III; 27 to 43 of SEQ ID NO:12) of the apoB promoter.

Still another aspect of the invention relates to a novel, isolated apolipoprotein transcription factor that is capable of binding to a regulatory sequence element of an apolipoprotein CIII (apoCIII) gene promoter. In preferred embodiments, the invention provides a novel, isolated apolipoprotein transcription factor that is capable of binding to a sequence element that has a nucleotide sequence comprising a nucleotide sequence found between approximately nucleotide number −87 and nucleotide number −72 (element B; 1325 to 1340 of SEQ ID NO:14) of the apoCIII gene promoter; or a novel, isolated apolipoprotein transcription factor that is capable of binding to a sequence element that has a nucleotide sequence comprising a nucleotide sequence found between approximately nucleotide number −138 and nucleotide number −119 (element C; 1274 to 1293 of SEQ ID NO:14) of the apoCIII gene promoter.

The invention also provides novel, isolated regulatory sequences of apolipoprotein gene promoters. In particular, one aspect of the invention relates to a novel, isolated regulatory sequence element of an apoA-I gene promoter, which preferably has a nucleotide sequence comprising either a nucleotide sequence found between approximately nucleotide number −175 and nucleotide number −148 (element C; 59 to 86 of SEQ ID NO:10) of the apoA-I gene promoter or, a nucleotide sequence comprising a nucleotide sequence found between approximately nucleotide number −220 and nucleotide number −190 (element D; 14 to 44 of SEQ ID NO:10) of the apoA-I gene promoter.

Another aspect of the invention relates to a novel, isolated regulatory sequence element of an apoA-II gene promoter, which preferably has a nucleotide sequence comprising either a nucleotide sequence found between approximately nucleotide number −40 and nucleotide number −33 (element A; 872 to 879 of SEQ ID NO:11) of the apoA-II gene promoter; a nucleotide sequence found between approximately nucleotide number −65 and nucleotide number −42 (element B; 847 to 870 of SEQ ID NO:11) of the apoA-II gene promoter; a nucleotide sequence found between approximately nucleotide number −126 and nucleotide number −110 (element C; 786 to 802 of SEQ ID NO:11) of the apoA-II gene promoter; a nucleotide sequence found between approximately nucleotide number −276 and nucleotide number −255 (element D; 636 to 657 of SEQ ID NO:11) of the apoA-II gene promoter; a nucleotide sequence found between approximately nucleotide number −377 and nucleotide number −364 (element E; 535 to 548 of SEQ ID NO:11) of the apoA-II gene promoter; a nucleotide sequence found between approximately nucleotide number −404 and nucleotide number −384 (element F; 508 to 528 of SEQ ID NO:11) of the apoA-II gene promoter; a nucleotide sequence found between approximately nucleotide number −468 and nucleotide number −455 (element G; 444 to 457 of SEQ ID NO:11) of the apoA-II gene promoter; a nucleotide sequence found between approximately nucleotide number −573 and nucleotide number −554 (element H; 339 to 358 of SEQ ID NO:11) of the apoA-II gene promoter; or a nucleotide sequence found between approximately nucleotide number −903 and −879 (element N; 9 to 33 of SEQ ID NO:11) of the apoA-II gene promoter.

Yet another aspect of the invention relates to a novel, isolated regulatory sequence element of an apoB gene promoter, which preferably has a nucleotide sequence comprising a nucleotide sequence found between approximately nucleotide number −118 and nucleotide number −98 (element I; 1 to 21 of SEQ ID NO:12) of said apoB gene promoter; a nucleotide sequence found between approximately nucleotide number −112 and nucleotide number −94 (element II; 7 to 25 of SEQ ID NO:12) of the apoB gene promoter; a nucleotide sequence found between approximately nucleotide number −86 and nucleotide number −62 (element III; 33 to 57 of SEQ ID NO:12) of the apoB gene promoter; a nucleotide sequence found between approximately nucleotide number −72 and nucleotide number −53 (element IV; 47 to 66 of SEQ ID NO:12) of the apoB gene promoter; or a nucleotide sequence comprising a nucleotide sequence found between approximately nucleotide number −53 and nucleotide number −33 (element V; 66 to 86 of SEQ ID NO:12) of the apoB gene promoter.

The invention also provides oligonucleotides having a nucleotide sequence comprising a binding site portion of a sense or antisense strand of an apolipoprotein gene promoter, the apolipoprotein gene promoter being selected from the group consisting of apoA-I, apoA-II, apoB, and apoCIII.

According to the invention, an isolated apolipoprotein transcription factor is provided, which factor is selected from the group consisting of AIC1, AIC2, AIC3, AIC4, AIC5, AID2, AID1a, AID3, AIIAB1, AIID1, AIID2, AIID3, AIID4, AIIM1, AIIM2, AIIN3, NF-BA2, NF-BA3, BCB1, BCB2, BCB3, NF-BA1, CIIIB1, and CIIIC1.

Also provided by the invention is an isolated apolipoprotein regulatory sequence element, which sequence element has a nucleotide sequence comprising a nucleotide sequence selected from the group consisting of a nucleotide sequence found between approximately nucleotide number −175 and nucleotide number −148 (element C; 59 to 86 of SEQ ID NO:10) of an apoA-I gene promoter; a nucleotide sequence found between approximately nucleotide number −220 and nucleotide number −190 (element D; 14 to 44 of SEQ ID NO:10) of an apoA-I gene promoter; a nucleotide sequence found between approximately nucleotide number −40 and nucleotide number −33 (element A; 872 to 879 of SEQ ID NO:11) of an apoA-II gene promoter; a nucleotide sequence found between approximately nucleotide number −65 and nucleotide number −42 (element B; 847 to 870 of SEQ ID NO: II) of an apoA-II gene promoter; a nucleotide sequence found between approximately nucleotide number −126 and nucleotide number −110 (element C; 786 to 802 of SEQ ID NO: II) of an apoA-II gene promoter; a nucleotide sequence found between approximately nucleotide number −276 and nucleotide number −255 (element D; 636 to 657 of SEQ ID NO: II) of an apoA-II gene promoter; a nucleotide sequence found between approximately nucleotide number −377 and nucleotide number −364 (element E; 535 to 548 of SEQ ID NO:11) of an apoA-II gene promoter; a nucleotide sequence found between approximately nucleotide number −404 and nucleotide number −384 (element F; 508 to 528 of SEQ ID NO:11) of an apoA-II gene promoter; a nucleotide sequence found between approximately nucleotide number −468 and nucleotide number −455 (element G; 444 to 457 of SEQ ID NO:11) of an apoA-II gene promoter; a nucleotide sequence found between approximately nucleotide number −573 and nucleotide number −554 (element H; 339 to 358 of SEQ ID NO:11) of an apoA-II gene promoter; a nucleotide sequence found between approximately −903 and −879 (element N; 9 to 33 of SEQ ID NO:11) of an apoA-II gene promoter; a nucleotide sequence found between approximately nucleotide number −118 and nucleotide number −98 (element I; 1 to 19 of SEQ ID NO:12) of an apoB gene promoter; a nucleotide sequence found between approximately nucleotide number −112 and nucleotide number −94 (element II; 7 to 25 of SEQ ID NO:12) of an apoB gene promoter; a nucleotide sequence found between approximately nucleotide number −86 and nucleotide number −62 (element III; 33 to 57 of SEQ ID NO:12) of an apoB gene promoter; a nucleotide sequence found between approximately nucleotide number −72 and nucleotide number −53 (element IV; 47 to 66 of SEQ ID NO:12) of an apoB gene promoter; and a nucleotide sequence found between approximately nucleotide number −53 and nucleotide number −33 (element V; 66 to 86 of SEQ ID NO:12) of an apoB gene promoter.

The invention also provides methods for modulating apolipoprotein gene transcription. In one aspect, the invention relates to a method of modulating apolipoprotein gene transcription comprising the step of interfering with an interaction between the apolipoprotein transcription factor of the invention and its cognate regulatory sequence element. In another aspect, the invention relates to a method of modulating apolipoprotein gene transcription comprising interfering with an interaction between the apolipoprotein transcription factor of the invention and another apolipoprotein transcription factor. In yet another aspect, the invention relates to a method of modulating apolipoprotein gene transcription comprising interfering with an interaction between an apolipoprotein transcription factor of the invention and a transcription machinery component.

DETAILED DESCRIPTION OF THE INVENTION

Definitions

The term "transcription factor", as that term is used herein, refers to a protein factor that is involved in modulating transcription from a promoter. The term "transcription factor" may refer to a protein factor that binds to a regulatory sequence element within a promoter. The term "transcription factor" may alternatively refer to a protein factor that does not itself bind to a regulatory sequence element within a promoter but that modulates transcription from that promoter through protein-protein interactions with other transcription factors. Such a non-binding transcription factor may be referred to as a "bridging" transcription factor.

The term "isolated", when applied to nucleic acids of the invention, means an RNA or DNA polymer which, by virtue of its origin or manipulation (i) is not associated with all of a nucleic acid with which it is associated in nature; (ii) is linked to a nucleic acid or other chemical moiety other than that to which it is linked in nature; or (iii) does not occur in nature. By "isolated" it is further meant a nucleic acid (i) amplified in vitro by, for example, polymerase chain reaction; (ii) synthesized by, for example, chemical synthesis; (iii) recombinantly produced by cloning; or (iv) purified, as by cleavage and gel separation.

The term "isolated", when applied to protein factors or polypeptides of the invention, means polypeptides (i) that are encoded by nucleic acids that were generated using recombinant DNA methods, (ii) that were synthesized by, for example, chemical synthetic methods; (iii) that are separated from at least some of the biological materials with which they are associated in nature; (iv) that are associated with chemical moieties (e.g. polypeptides, carbohydrates, fatty acids and the like) other than those with which they are associated in nature; or (v) do not occur in nature.

The term "sense", when applied to a nucleic acid of the invention, refers to a nucleic acid having a nucleotide sequence corresponding to a nucleotide sequence found in a coding strand of a gene nucleic acid. The term "antisense", when applied to a nucleic acid of the invention, refers to a nucleic acid having a nucleotide sequence corresponding to a nucleotide sequence found in a non-coding strand of a gene nucleic acid.

BRIEF DESCRIPTION OF THE DRAWINGS

FIG. 1A depicts proximal regulatory sequence elements. FIG. 1B depicts protein factors that bind to proximal regulatory sequence elements of the apoA-I gene promoter. FIG. 1C depicts the transcriptional effects of mutations that disrupt factor binding to regulatory sequence elements. The sequences depicted in this Figure are apoA-I sequences −233 to −72 and −26 to +31, which correspond to sequences 1 to 162 and 208 to 261, respectively, of SEQ ID NO:10.

FIG. 2A–2C are a schematic representation of regulatory sequence elements and transcription factors that bind to them in the apoA-II gene promoter. FIG. 2A depicts the regulatory sequence elements. FIG. 2B depicts the transcriptional effects of mutations that disrupt factor binding to regulatory sequence elements. FIG. 2C depicts protein factors that bind to regulatory sequence elements of the apoA-II gene promoter. The sequences depicted in this Figure are apoA-II sequences −903 to −879, −853 to −829, −803 to −716, −573 to −554, and −65 to −33, which correspond to sequences 9 to 33, 59 to 83, 109 to 196, 339 to 358, and 847 to 879, respectively, of SEQ ID NO:11.

FIG. 3A depicts long-distance regulatory sequence elements. FIG. 3B depicts proximal regulatory sequence elements. FIG. 3C depicts protein factors that bind to proximal regulatory sequence elements of the apoB gene promoter. FIG. 3D depicts the transcriptional effects of mutations that disrupt transcription factor binding to regulatory sequence elements. The sequences depicted in this Figure are apoB sequences −118 to −33 (SEQ ID NO:12) and +33 to +52 (SEQ ID NO:13).

FIG. 4A–4D are a schematic representation of regulatory sequence elements and transcription factors that bind to them in the apoCIII gene promoter. FIG. 4A depicts long distance regulatory sequence elements. FIG. 4B depicts proximal and distal regulatory sequence elements. FIG. 4C depicts protein factors that bind to regulatory sequence elements in the apoCI gene promoter. FIG. 4D depicts the transcriptional effects of mutations that disrupt factor binding to regulatory sequence elements. The sequences depicted in this Figure are apoCI sequences −797 to −776, −771 to −722, −714 to −682, −674 to −639, −619 to −586, −429 to −394, −165 to −114, −92 to −67, and −37 to −12, which correspond to sequence numbers 615 to 636, 641 to 690, 698 to 730, 738 to 773, 792 to 826, 983 to 1018, 1247 to 1298, 1320 to 1345, and 1375 to 1400, respectively, of SEQ ID NO:14.

FIG. 6A–6D depict nucleotide sequences of the apoA-I, apoA-II, apoB, and apoCIII promoters. FIG. 6A is SEQ ID NO:10, which is the apoA-I promoter sequence between nucleotide position numbers −233 and +32. FIG. 6B is SEQ ID NO:11, which is the apoA-II promoter sequence between nucleotide position numbers −911 and +29. FIG. 6C is SEQ ID NO:12, which is the apoB promoter sequence between nucleotide position numbers −118 and −33, and; SEQ ID NO:13, which is the apoB promoter sequence between nucleotide position numbers +33 and +52. FIG. 6D is SEQ ID NO:14, which is the apoCIII promoter sequence between nucleotide position numbers −1411 and +24.

DESCRIPTION OF THE SEQUENCE

Figure 1:
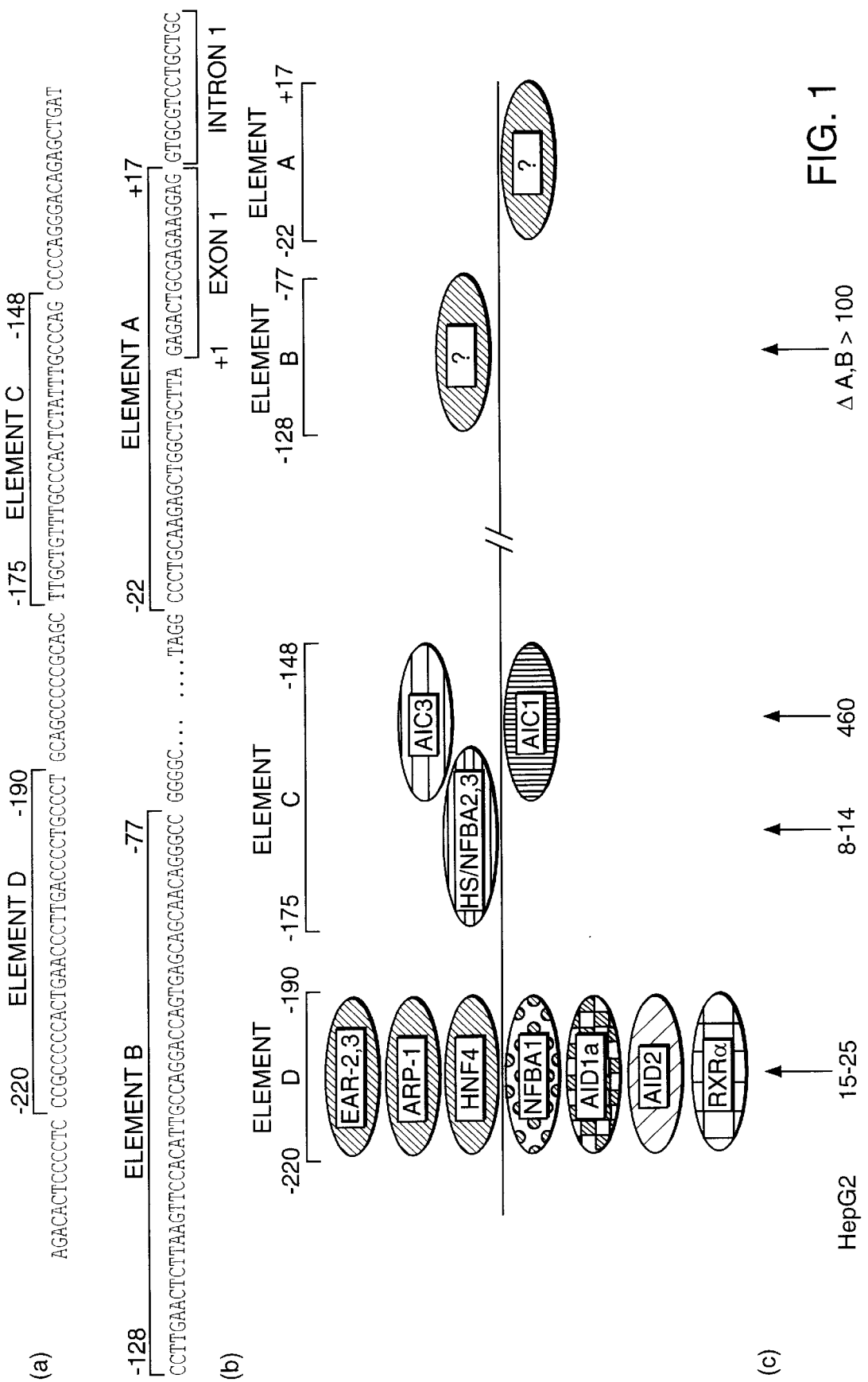
FIGS. 1A–1C are a schematic representation of regulatory sequence elements and transcription factors that bind to them in the apoA-I gene promoter.
Figure 2B:
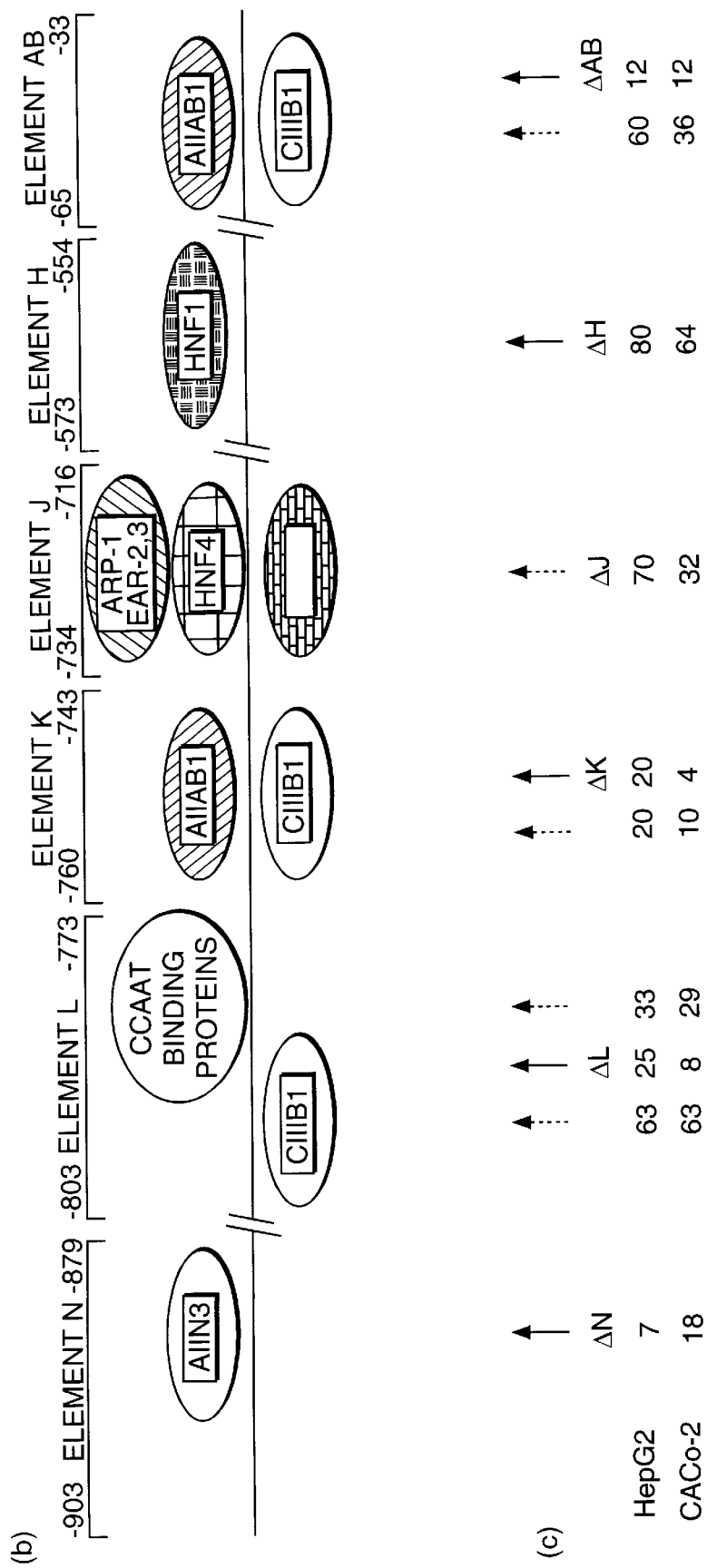
Figure 3:
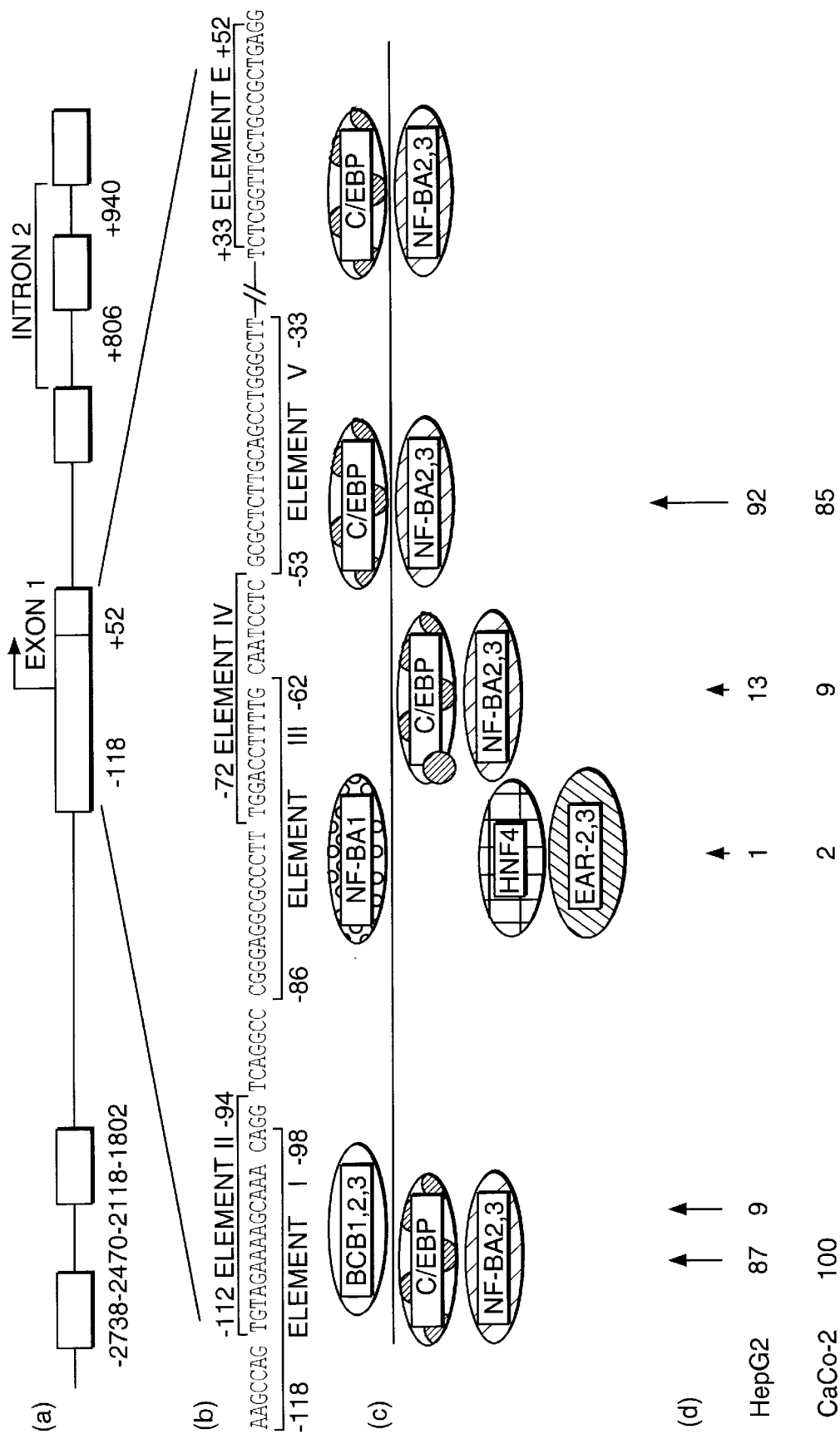
FIG. 3A–3D are a schematic representation of regulatory sequence elements and transcription factors that bind to them in the apoB gene promoter.
Figures 4, 4A:
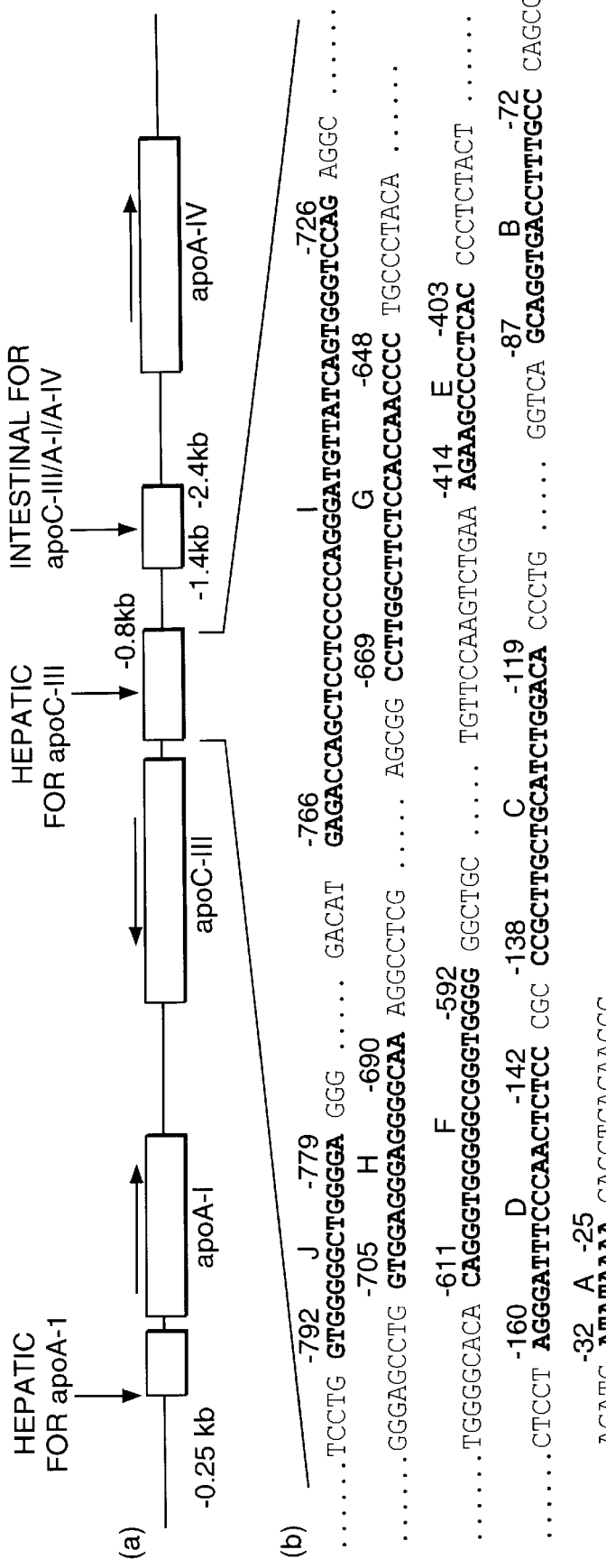
Figure 4B:
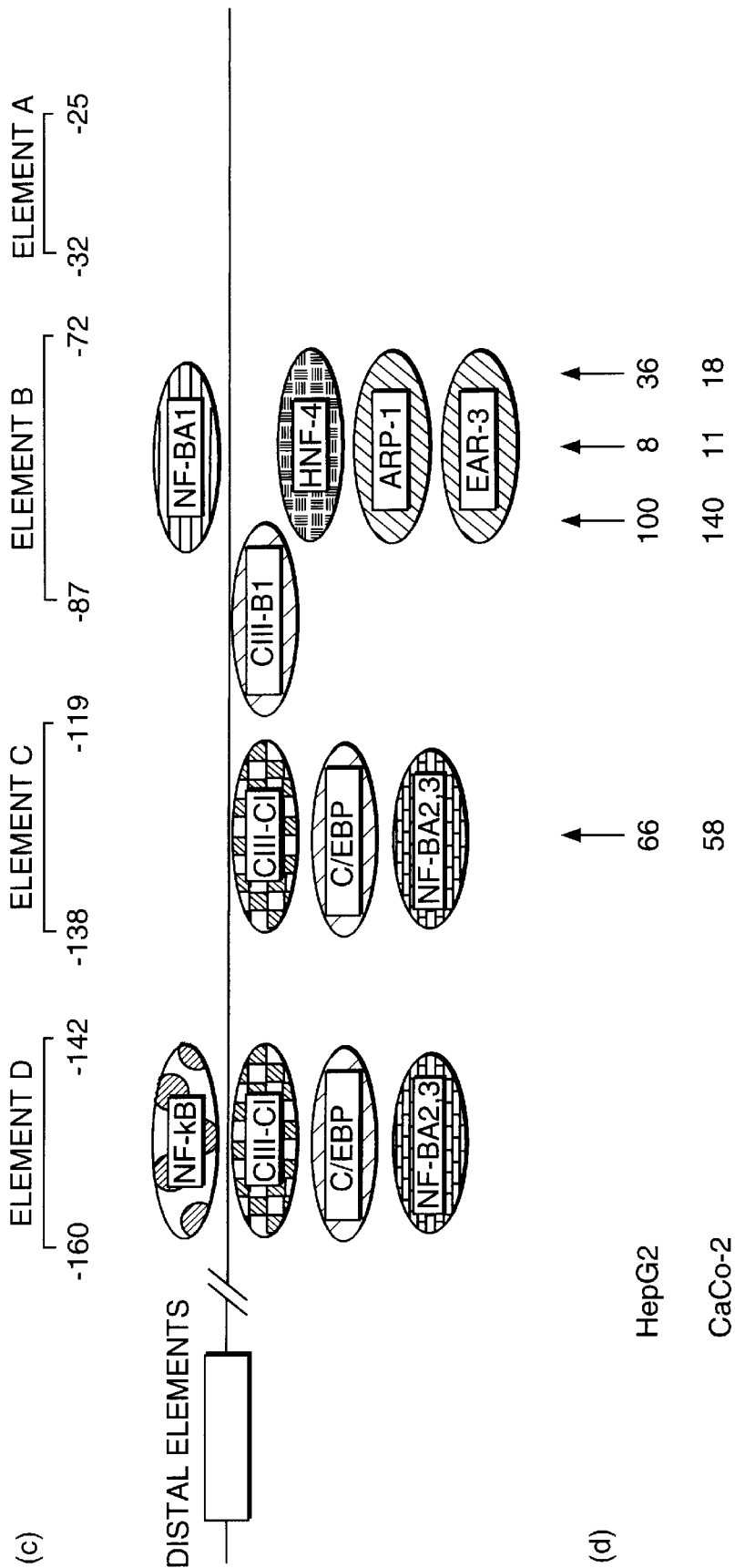

SEQ ID NO:1 is apoA-II promoter region −911 to −650.
SEQ ID NO:2 is apoB promoter region −79 to −63.
SEQ ID NO:3 is apoB promoter sequences in the apoB-CAT construct.
SEQ ID NO:4 is apoB promoter sequences −154 to +53.
SEQ ID NO:5 is apoB promoter region −88 to −62.
SEQ ID NO:6 is apoB promoter elements I to IV.
SEQ ID NO:7 is the apoCIII promoter region −1411 to +24 (same as SEQ ID NO:14).
SEQ ID NO:8 is apoA-I promoter regions A through D.
SEQ ID NO:9 is apoA-II promoter regions A through M.
SEQ ID NO:10 is the apoA-I promoter region −233 to +32.
SEQ ID NO:11 is the apoA-II promoter region −911 to +29.
SEQ ID NO:12 is the apoB promoter region −118 to −33.
SEQ ID NO:13 is the apoB promoter region +33 to +52.
SEQ ID NO:14 is the apoCIII promoter region −1411 to +24 (same as SEQ ID NO:7).
SEQ ID NO:15 is the direct repeat found at −210 to −203 of apoA-I promoter element D.
SEQ ID NO:16 is the direct repeat found at −202 to −195 of apoA-I promoter element D.
SEQ ID NOs: 17–34 are sequences of competitor oligonucleotides used in the analysis of the apoA-I promoter and presented in Table 1.
SEQ ID NOs:35–66 are sequences of competitor oligonucleotides used in the analysis of the apoA-II promoter and presented in Table 3.
SEQ ID NOs:67–70 are sequences of apoB promoter oligonucleotides presented in Table 4.
SEQ ID NO:71–87 are sequences of mutant apoB promoter oligonucleotides presented in Table 6.
SEQ ID NOs:88–90 are sequences of mutant apoCIII promoter oligonucleotides presented in Table 7.
SEQ ID NO:91 is the octameric motif 5'-CAGGTGAC-3'
SEQ ID NO:92 is a polylinker region used in constructing plasmids for the analysis of the apoA-I promoter.
SEQ ID NO:93 is the primer PCR-LM5.
SEQ ID NO:94 is the primer rev-5-26.
SEQ ID NO:95 is the primer PCR-LM5c.
SEQ ID NO:96 is the primer PCR-B8R.
SEQ ID NO:97 is the primer PCR-LM6.
SEQ ID NO:98 is the primer PCR-LM6c.
SEQ ID NOs:99–100 are the two strands of an oligonucleotide linker used in plasmid construction.
SEQ ID NOs:101–102 are the two strands of an oligonucleotide used in affinity chromatography.
SEQ ID NO:103 is oligonucleotide PCR264AI.
SEQ ID NO:104 is oligonucleotide OL-AI-1c.
SEQ ID NO:105 is oligonucleotide PCRAII3.
SEQ ID NO:106 is an oligonucleotide corresponding to −80 to −63 of apoB.
SEQ ID NOs: 107–108 are the strands of a double-stranded oligonucleotide corresponding to apoCIII −90 to −73, which double-stranded oligonucleotide was used on an affinity column.
SEQ ID NO:109 is a primer including a strong translation initiation sequence.
SEQ ID NOs: 110–111 are forward and reverse primers, respectively, used in PCR reactions employed to clone the rat HNF-4 gene.
SEQ ID NO:112 is a BamHI/XhoI linker.
SEQ ID NO:113 is a BamHI linker.

Description of the Preferred Embodiments

The present invention relates to the regulation of apolipoprotein gene transcription. In particular, the invention relates to the identification and characterization of the exact regulatory sequences and protein factors involved in regulating transcription of the apoA-I, apoA-II, apoB, and apoCIII genes. For simplicity, we propose a nomenclature that describes the protein factors that bind to regulatory elements of apolipoprotein genes based on (i) the name of the target gene (e.g. apoA-I); (ii) the identified region to which the factor binds (regions are given letter names, as indicated below); and (iii) the mobility of the DNA-protein complexed that is formed when the factor binds to the regulatory element (higher numbers reflect increased mobility). For example, the protein factor that forms the lowest mobility complex with region D of the apoA-I promoter (see below) is designated AID1. The protein factor name may interchangeably be used to refer to the gel shift complex.

Much of our work involved purification of protein factors. As will be appreciated by those skilled in the art, successful purification of protein factors by column chromatography involves careful selection of column types, elution conditions, and column order. Workers skilled in the art will further appreciate that, once purification studies have been performed with a particular protein factor, the information provided thereby can used to develop alternate purification strategies for the same factor.

We discuss the regulation of each apolipoprotein gene individually below. For convenience of presentation, we often describe apolipoprotein promoter sequences by the nucleotide position at which they are located in the apolipoprotein gene. FIGS. 1-4 provide schematic representations of the apoA-I, apoA-II, apoB, and apoCIII promoters, respectively, with the numbering scheme indicated.

ApoA-I

Apolipoprotein A-I (apoA-I) is the major protein component of high density lipoprotein and has defined protein and gene sequences (see Zannis et al. Curr. Op. Lipidology 3:96–113, 1992; Zannis et al. Adv. Human Genet. 21:145–319, 1993; and references cited therein). Plasma apoA-I serves as a cofactor for lecithin-cholesterol acyltransferase. Furthermore, in tissue culture studies, apoA-I promotes cholesterol efflux from cultured cells, a process known as reverse cholesterol transport. It is believed that the latter function is mediated by interaction of high density lipoprotein with a cell surface receptor designated the "high density lipoprotein receptor". ApoA-I synthesis has been demonstrated predominantly in the liver and in the intestine of most but not all mammalian species. Small quantities of apoA-I mRNA have also been found in a variety of mammalian tissues.

Recent studies have shown that tissue apoA-I mRNA levels are controlled by hormonal and nutritional factors and are developmentally regulated (see Sorci-Thomas et al. J. Lipid. Res. 30:1397–1403, 1989; El Shourbagy et al. Proc. Natl. Acad. Sci. U.S.A. 82; 8242–8246, 1985; Tamet of Proc. Natl. Acad. Sci. U.S.A. 83:3111–3115, 12986; Haddad et al. J. Biol. Chem 261:13268–13277, 1986). Human subjects with genetically determined low or high plasma apoA-I or high density lipoprotein levels have an increased or decreased risk of developing atherosclerosis, respectively, indicating the importance of regulation of synthesis of apoA-I. (See Castelli et al. Circulation 55:767–772, 1977; Heiss et al. Proc. Wkshp. Apolip. Quant. NIH Pub. 83–1266, pp. 7–24, U.S. Dept. of HHS, NIH, 1982; Glueck et al. Arch. Intern. Med. 135:1025–1028, 1975; Glueck et al. J. Lab. Clin. Med. 88:941–957, 1976; Patsch et al. Arteriosclerosis 1:156–161, 1981)

Prior to our work, little information was available about the sequence elements and protein factors involved in transcriptional regulation of the apoA-I gene. Studies had indicated that the sequence elements required for hepatic transcription of the apoA-I gene were located downstream of nucleotide −239 relative to the transcription start site (Higuchi et al. J. Biol. Chem. 263:18530–18536, 1988; Sastri et al. Mol. Cell. Biol. 8:605–614, 1988; Walsh et al. J. Biol. Chem. 264:2488–6494, 1989). However, the exact location of the individual regulatory elements were not known.

Additionally, little was known about the protein factors involved in regulating the apoA-I promoter. Hardon et al. had identified a factor they called LF-A1, that is present in rat liver extracts but not in spleen extracts, and that can bind to a sequence found between approximately −221 and −195 (EMBO J. 7:1711–1719, 1988). The significance of LF-A1 binding to the apoA-I promoter was not addressed and no other factors were identified or regulatory sequences mapped.

We have performed a detailed analysis of the apoA-I promoter and have and characterized the regulatory sequences and protein factors involved in transcriptional regulation of the apoA-I gene (Papazafiri et al. J. Biol. Chem. 266:5790–5797, 1991, incorporated herein by reference). In particular, we have defined four sequence elements, A–D, that are involved in transcriptional regulation of the apoAI gene. We have identified five protein factors, AIC1–5, that bind to sequence element C. Two of these factors, AIC1 and AIC3, are novel regulators of the apoA-I gene. We have purified factor AIC1. We have also identified new factors, AID2, AID1a, and AID3 that bind to apoA-I sequence element D. We have performed purification studies of factors AID2 and AID3. For a description of the detailed procedures we used in these studies, see Example 1. The results of our investigations are summarized in FIG. 1.

Promoter mapping studies

DNaseI footprinting analysis of the proximal apoA-I promoter sequences with hepatic nuclear extracts identified four protected regions "downstream" (closer to the transcription start site) of nucleotide −239, the approximate boundaries of which are:

A: −22 to +17 (212 to 250 of SEQ ID NO:10)
B: −128 to −77 (106 to 158 to SEQ ID NO:10)
C: −175 to −148 (59 to 86 of SEQ ID NO:10)
D: −220 to −190 (14 to 44 of SEQ ID NO:10)

As will be discussed further below, the identities of the protein factors that bind to these elements were established by DNA binding and competition assays. The transcriptional significance of these sequences, and of the factors that bind to them was studied in transcription assays. In some cases, individual protein factors were further characterized through purification.

Analysis of Region C

We have use gel shift assays to identify protein factors that bind to region C (−175 to −148) of the apoA-I promoter. We have identified five distinct protein-DNA complexes, designated AIC1–AIC5, that form on an oligonucleotide corresponding to apoA-I sequences −175 to −148 in a rat liver nuclear extract.

We have characterized the AIC1–AIC5 protein factors by determining their stability to heat treatment at 85° C. for 5 minutes. We found that three specific protein-DNA complexes formed when heat treated extracts were incubated with the apo-AI −175 to −148 probe. The three complexes formed with heat-treated extracts corresponded in mobility with complexes AIC2, AIC4, and AIC5 that form with untreated extracts. This analysis indicated that the AIC1 and AIC3 activities are heat-labile and the AIC2, AIC4, and AIC5 activities are heat-stable.

We investigated the relationship of the AIC1, AIC2, AIC3, AIC4, and AIC5 protein factors to known transcription factors using gel shift competition and DNaseI protection studies. The competitor oligonucleotides that we tested contained binding sites for the known factors NFY (Maire et al. Science 244:343–346, 1989), C/EBP (Maire et al. id; Raymondjean et al. Proc. Natl. Acad. Sci. U.S.A. 85:757–761, 1988; Dorn et al. Cell 50:863–872, 1987), NF1 (Maire et al. id), NFY (Maire et al. id), and NFY* (Dorn et al. supra). We also tested oligonucleotides BA3 (SEQ ID NO:43), which contains apoB sequences between −78 and −48 (element IV), 41–71 of SEQ ID NO:12, including and CIIID (SEQ ID NO:20), which contains apoCIII sequences between −160 to −142 (element D; 1252 to 1270 of SEQ ID NO:14) Both apoB element IV and apoCIII element D are recognized by C/EBP and other protein factors (see sections on apoB and apoCIII for a full description of the protein factors that bind to apoB element IV; 47 to 66 of SEQ ID NO:12 and apoCIII element D; 1252 to 1270 of SEQ ID NO:14). The sequences of the competitor oligonucleotides we used are presented in Table 1 (see Example 1).

We found that complexes AIC2, AIC4, and AIC5 are competed out by oligonucleotides containing the binding sites of C/EBP and NFY, as well as by the oligonucleotides containing apoB sequences −78 to −48 (element IV) and apoCIII sequences −160 to −142 (element D; 1252 to 1270 of SEQ ID NO:14). DNaseI footprinting analysis with heat-treated extracts further revealed that protein factors AIC2, AIC4, and AIC5 protected the same region (−175 to −155) of element C of the apo-AI promoter as is protected by C/EBP produced in bacteria using the rat C/EBP cDNA. These results suggested that the AIC2, AIC4, and AIC5 protein factors might be related to C/EBP. However, we found that DNA binding by bacterially-produced C/EBP gave a gel shift complex with different mobility than that of any of the AIC1–5 complexes. We therefore conclude that the AIC2, AIC4, and AIC5 protein factors are distinct from C/EBP. The AIC2, AIC4, and/or AIC5 protein factors may be related to two protein factors, designated NF-BA2 and NF-BA3, that we have identified and characterized as activators of apoB transcription (see discussion of apoB promoter elements I, IV, V, and E below).

Our gel shift competition studies also revealed that the AIC1 complex could be competed out by oligonucleotides containing the binding site for NFY or NFY*. The AIC3 gel shift complex could be competed out by oligonucleotides containing apoCIII sequences −160 to −142 (element D).

The results of our gel shift competition experiments allowed us to determine experimental conditions under which only complex AIC1 or complex AIC3 would form on a DNA fragment containing apo-AI promoter element C. In particular, we performed DNaseI competition experiments in the presence of either (i) an oligonucleotide that contains an NFY binding site and that competes out the AIC1 complex but not the AIC3 complex; (ii) an oligonucleotide that contains apoCIII sequences −160 to −142 (element D; 1252 to 1270 of SEQ ID NO:14) and that competes out the AIC3 complex but not the AIC1 complex; or (iii) an oligonucleotide that contains a C/EBP binding site and that competes neither the AIC1 complex nor the AIC3 complex. All three of the competitor oligonucleotides used competed complexes AIC2, AIC4, and AIC5. Therefore, in the presence of the oligonucleotide that contains an NFY binding site, only complex AIC3 forms; in the presence of the oligonucleotide that contains apoCIII sequences −160 to −142 (element D; 1252 to 1270 of SEQ ID NO:14), only the AIC1 complex forms; and in the presence of the oligonucleotide that contains a C/EBP binding site, both complexes AIC1 and AIC3 form, but complexes AIC2, AIC4, and AIC5 do not. The results of these studies indicated that the AIC1 and AIC3 protein factors bind to overlapping sites in the apo-AI −168 to −148 promoter region.

We used mutational studies to disrupt the protein-DNA interactions that we had identified and to thereby determine the relationship between protein factor binding and transcriptional activity. In particular, we found that AIC1 formation is not competed by a mutant oligonucleotide, AICM3 (SEQ ID NO:32), which contains apo-AI sequences −177 to −142 but includes a substitution mutation of residues −164 to −159. Apparently, the mutation of AICM3 abolishes AIC1 binding. By contrast, mutant oligonucleotide AICM4 (SEQ ID NO:33), which contains a substitution mutation of apo-AI residues −158 to −153, partially competes the AIC1 complex, and oligonucleotide AICM2 (SEQ ID NO:31), which contains a substitution mutation of apo-AI residues −171 to −166, competes the AIC1 complex fully. The results indicated that the AIC1 protein factor does not bind to the AICM3 mutant oligonucleotide and that AIC1 binding probably does not require apo-AI sequences between −171 to −166, but does require sequences between approximately −164 to −153.

When we introduced the AICM3 mutation, which apparently abolishes AIC1 binding, into a Chloramphenicol Transferase ("CAT") reporter construct assayed in HepG2 cells, we found that expression increased approximately 4.6 fold. This result indicated that AIC1, when bound to apo-AI promoter region C, functions as a transcriptional repressor.

Our mutational studies also revealed that the AIC3 complex and the AIC2,and AIC4, complexes are all partially competed by mutant oligonucleotides AICM2 and AICM4, and are completely competed by mutant oligonucleotide AICM3. Furthermore, direct binding studies with heat-treated extracts revealed that the formation of complexes AIC2, AIC4, and AIC5 is dramatically reduced with mutant oligonucleotides AICM2 and AICM4, but not with mutant oligonucleotide AICM3. We therefore conclude that the AICM2 and AICM4 mutations can disrupt the binding of the AIC3 heat-labile and AIC2, AIC4, and AIC5 heat stable protein factors.

The introduction of mutations AICM2 or AICM4 into a CAT reporter construct decreased transcription to 8% and 14%, respectively, of control levels. The result is consistent with the idea that the AIC3, AIC2, AIC4, and AIC5 protein factors, when bound to the apo-AI promoter region C, function as transcriptional activators.

We have performed purification studies of the AIC1 protein factor. We have found that AIC1 activity elutes at 40 mM KCl from a phosphocellulose column and from a Q-Sepharose column, and that AIC1 can be further purified using sequence specific DNA affinity chromatography with an oligonucleotide probe containing apoA-I sequences −178 to −142.

ApoA-I element C is also recognized by protein factors NF-BA2 and NF-BA3, which we identified as regulators of apoB transcription (see discussion of apoB elements I, IV, V, and E). Protein factors AIC1 and AIC3 can be distinguished from NF-BA3 on the basis of, for example, stability to heat inactivation by treatment at 85° C. for five minutes. AIC1 and AIC3 activities are heat labile while NA-BA2 and NF-13A3 activities are heat stable. Protein factors AIC2, AIC4, and AIC5, as mentioned above, may be related to NF-BA2 and NF-BA3.

Analysis of region D

We have identified and characterized protein factors that are present in rat liver nuclear extracts and that can bind to region D of the apo-AI promoter. One of these factors is NF-BA1, a protein we originally identified as a transcriptional activator of the apoB gene (see discussion of apoB promoter element m and Example 3). Two other factors, designated AID1 and AID2, were identified by fractionation of rat liver nuclear extracts on heparin-agarose followed by DNA binding gel electrophoresis ("gel shift") with element D (−220 to −190; 14 to 44 of SEQ ID NO:10) of the apoA-I promoter (Papazafiri et al. 1991 supra). Factor AID1 eluted from the heparin-agarose column at an average concentration of 500 mM KCl; factor AID2 eluted at an average concentration of 350 mM KCl. The AID1 gel shift complex had lower mobility than did the AID2 gel shift complex. Additional activities, designated AID1a and AID3, were identified by fractionation of rat liver nuclear extracts on Q-Sepharose. Factor AID1a eluted from Q-Sepharose at approximately 0.2–0.3M KCl and produced a gel shift complex with lower mobility than the AID1, AID2, and NF-BA1 complexes; factor AID3 eluted at approximately 0.4M KCl and produced a gel shift complex with higher mobility than the other complexes. The AID2, AID1a, and AID3 activities were heat labile to treatment at 85° C. for five minutes.

The relationship of AID1 and AID2 to known transcription factors was investigated by DNA binding competition assays. This analysis showed that AID1 binding to an apoA-I fragment including apoA-I sequences −215 to −191 can be competed out by the same apoA-I fragment, by the apoB −88 to −62 fragment, or by an oligonucleotide containing the binding site for LF-A1. Furthermore, AID1 bound to and retarded the oligonucleotide containing the LF-A1 site in a gel shift assay. These results indicated that AID1 is identical to LF-A1. We therefore refer to this factor as AID1(LF-A1).

DNA binding competition analysis revealed that AID2 binding to a fragment that includes apoA-I sequences −215 to −191 can be completely competed by the same apoA-I fragment, and partially competed by a fragment containing apoB sequences −88 to −62. However, the binding is not competed by oligonucleotides that contain the binding sites for NF1 (Paonessa et al. EMBO J. 7:3115–3123, 1988), NFY (Marie et al. Science 244:343–346, 1989), SP1 (Briggs et al. Science 234:47–52, 1986), octamer motif binding protein (Bohman et al. Nature 325:268–272), or LF-A1 (Hardon et al. supra). The results indicated that AID2 is a novel DNA-binding protein.

We have performed purification studies with factors AID2 and AID3. Factor AID2 eluted from a Q-Sepharose column at approximately 0.2M KCl, and from a Bio-Rex 70 column at approximately 0.4 to 0.5M KCl. Factor AID2 can be further purified by sequence-specific DNA-affinity chromatography using a concatenated double-stranded oligonucleotide corresponding to apoA-I promoter element D (−220 to −190; 14 to 44 of SEQ ID NO:10) as a ligand. These studies revealed that factor AID2 may be related to factor NF-BA1, which is discussed in detail below (see discussion of apoB promoter element III).

Factor AID3 was purified by chromatography on a Q-Sepharose column, followed by a Bio-Rex 70 column. AID3 eluted at approximately 0.4M KCl from each column. AID3 can be further purified by sequence-specific DNA-affinity chromatography using a concatenated double-stranded oligonucleotide corresponding to apoA-I promoter element D (−220 to −190; 14 to 44 of SEQ ID NO:10) as a ligand.

Further studies by us and others have revealed that additional factors can bind to element D of the apoA-I promoter. Specifically, these studies have revealed that transcription factors HNF4, ARP-1, EAR-2, and EAR-3, which are members of the steroid/thyroid hormone receptor superfamily, can bind to this element (see Sladek et al. Genes Dev. 4:2353–2365, 1990; Ladias et al. Science 251:561–565, 1991; Ladias et al. J. Biol. Chem. 267:15849–15860, 1992, incorporated herein by reference; and Example 5). We have also found that the thyroid and retinoic acid receptor proteins RARα, RXRα, and TRβ can bind to this element in homo- or hetero-dimer complexes. The gel shift complexes produced by these steroid receptor factors are distinct in mobility from the AID1a, AID1, NF-BA1, AID2, and AID3 complexes.

Gel shift studies have revealed that the protein factors that recognize element D of the apoA-I promoter also bind to sequences in element J (−734 to −716; 178 to 196 of SEQ ID NO:11) of the apoA-II promoter, element III (−86 to −62; 33 to 57 of SEQ ID NO:12) of the apoB promoter, and element B (−87 to −72; 1325 to 1340 of SEQ ID NO:14) of the apoCIII promoter.

We have assayed the transcriptional significance of DNA binding by these factors using several different assays. Co-transfection experiments in HepG2 cells have revealed that ARP-1, EAR-2, and EAR-3 function as transcriptional repressors from apoA-II element J (−743 to −716; 178 to 196 of SEQ ID NO: II), apoB element III (−86 to −62; 33 to 57 of SEQ ID NO:12), and apoCIII element B (−87 to −72; 1325 to 1340 of SEQ ID NO:14). In similar experiments, Ladias et al. (Science 251:561–565, 1991) found that ARP-1 functions as a transcriptional repressor from apoA-I element D. We further found that HNF4 acts as a transcriptional activator from apoA-II element J (−743 to −716; 178 to 196 of SEQ ID NO:11), apoB element m (−86 to −62; 33 to 57 of SEQ ID NO:12), and apoCIII element B (−87 to −72; 1325 to 1340 of SEQ ID NO:14), and can reverse the repression mediated by ARP-1.

In vivo transcription experiments using a CAT reporter construct revealed that introduction of nucleotide substitution mutations within element D of the apoA-I promoter resulted in a reduction of hepatic transcription to background levels. This result indicates that the observed binding by ARP-1, EAR-2, and EAR-3 is unlikely to have physiological significance, since those factors function as transcriptional repressors. By contrast, we have found that factor NF-BA1 functions as a transcriptional activator (see discussion of apoB promoter element III). Furthermore, gel shift studies with mutant oligonucleotides have revealed that the direct repeats 5'-TGAACCCT-3' (SEQ ID NO:15) and 5'-TGACCCCT-3' (SEQ ID NO:16), found at −210 to −203 and −202 to −195 of apoA-I promoter element D, respectively, are important for DNA binding by NF-BA1, AID1, AID2, AID1a, AID3, and HNF-4. Introduction of the same mutations into our CAT expression system correlates with a decrease in transcription. We therefore conclude that NF-BA1, AID1, AID2, AID1a, AID3, and HNF-4 function as transcriptional activators of the apoA-I gene.

ApoA-II

Human apolipoprotein A-II (apoA-II) is a major protein component of HDL (plasma concentration of 0.3–0.5 mg/mL) and is synthesized by the liver and, to a much lesser extent, by the intestine (See Zannis et al. Curr. Op. Lipidol. 3:96–113, 1992; Zannis et al. Adv. Human Genet. 21:145–319, 1993; and references cited therein). ApoA-II has known protein and gene sequences and exists in plasma as a dimer of two 77-amino-acid-long subunits linked by an intra-disulfide bond at residue 6. Following synthesis, apoA-II is subject to intra- and extra-cellular modifications, which include a new type of modification, O-glycosylation, propeptide cleavage, and cyclization of the N-terminal glutamine. Following secretion, apoA-II is mostly incorporated into lipoprotein particles containing apoA-I and apoA-II (LpAI:AII).

It has been reported that inbred strains of mice with increased apoA-II levels are associated with increased HDL size, suggesting that the plasma concentration of apoA-II may affect HDL structure and function(s) (Lusis J. Lipid Res. 29:397–429, 1988; Doolittle et al. J. Biol. Chem.

265:16380–16388, 1990). Overexpression of the human apoA-II gene in transgenic mice affected the size and the distribution of HDL particles, but did not affect the plasma HDL concentration (Schultz et al. 1991).

Prior to our work, five sequence regions had been identified upstream of the apoA-II gene, between about –853 and –671, that are important for the regulation of apoA-II transcription, and some protein factors that could potentially bind within those regions had been identified (Shelley et al. Nuc. Acid Res. 15:3801–3821, 1987; Lucero et al. Nuc. Acid Res. 17:2283–2300, 1989). This information provided a preliminary framework for understanding the transcriptional regulation of the apoA-II gene, but was incomplete.

We have performed a detailed analysis of the apoA-II promoter and have identified and characterized the regulatory sequences and protein factors involved in transcriptional regulation of the apoA-II gene (see Chambaz et al. J. Biol. Chem. 266:11676–11685, 1991; Cardot et al. J. Biol. Chem. 266:24460–24470, 1991; and Cardot et al. Biochemistry 32:9080–9093, 1993, each of which is incorporated herein by reference). In particular, we have identified 14 sequence elements, designated A–N, that are involved in transcriptional regulation of the apoA-II gene. Nine of those elements, A–H and N, are outside of the region previously recognized to be important for apoA-II transcriptional regulation. We have also identified protein factors AIIAAB1, AIID1, AIID2, AIID3, AIID4, AIIM1, AIIM2, and AIIN3 that bind to the apoA-II regulatory sequences. Factors AIIAB1 AIID1, AIID2, AIID3, and AIID4 have been purified. For a description of the detailed procedures we used in these studies, see Example 2. The results of our investigations are summarized in FIG. 2.

Promoter mapping studies

We first studied the regulatory elements that direct tissue-specific expression of the apoA-II gene by generating a fusion construct in which transcription of a CAT reported gene was out under the control of the apoA-II promoter. We then tested the transcriptional effects of sequential and internal promoter deletions on expression of the reporter gene. We found that the apoA-II –911 to +29 promoter region (SEQ ID NO:11) has strong promoter activity in hepatic and intestinal cells. We further found that the –911 to +29 apoA-II promoter fragment (SEQ ID NO:11) was able to direct tissue-specific gene expression.

An apoA-II promoter fragment containing sequences between approximately –860 and +29 was still able to direct tissue-specific expression, but at reduced levels: hepatic transcription was reduced to 7% of control levels and intestinal transcription was reduced to 18% of control levels. This result indicated that the apoA-II region between –911 and –860 includes a sequence element(s) that is(are) important for hepatic and intestinal transcription.

Smaller fragments, including apoA-II sequences –614 to +29 or less, were inactive for both hepatic and intestinal transcription. We investigated the transcriptional sequences downstream of –614 by generating internal deletions within the –911 to +29 apoA-II promoter fragment. We found that deletion of sequences between –614 and –230 reduced hepatic transcription to 60% of control levels, but increased intestinal transcription to 140% of control levels. These results indicated that, while sequences between –614 and –230 may contribute to optimal gene expression, they are not essential for apoA-II expression and further that different sets of regulatory factors may direct apoA-II transcription in hepatic and intestinal cells.

The regulatory elements controlling hepatic transcription of the apoA-II gene were further defined in DNaseI footprinting experiments using fragments that span apoA-II sequences –911 to +29 (SEQ ID NO:11). These studies identified 14 regulatory elements in the apoA-II promoter that are protected from DNaseI digestion in rat liver extracts, the approximate boundaries of which are:

A: –40 to –33 (872 to 879 of SEQ ID NO:11)
B: –65 to –42 (847 to 870 of SEQ ID NO:11)
C: –126 to –110 (786 to 802 of SEQ ID NO:11)
D: –276 to –255 (636 to 657 of SEQ ID NO:11)
E: –377 to –364 (535 to 548 of SEQ ID NO:11)
F: –404 to –384 (508 to 528 of SEQ ID NO:11)
G: –468 to –455 (444 to 457 of SEQ ID NO:11)
H: –573 to –554 (339 to 358 of SEQ ID NO:11)
I: –706 to –680 (206 to 232 of SEQ ID NO:11)
J: –734 to –716 (178 to 196 of SEQ ID NO:11)
K: –760 to –743 (152 to 169 of SEQ ID NO:11)
L: –803 to –773 (109 to 139 of SEQ ID NO:11)
M: –853 to –829 (59 to 83 of SEQ ID NO:11)
N: –903 to –879 (9 to 33 of SEQ ID NO:11)

Elements A–H and N are outside of the regions that had previously been studied and therefore represent previously unidentified regulatory elements.

As will be discussed further below, the identities of the protein factors that bind to these elements were established by DNA binding and competition assays. The transcriptional significance of these sequences, and of the factors that bind to them was studied in transcription assays. In some cases, individual protein factors were further characterized by purification.

Element AB

Gel shift studies with an oligonucleotide probe corresponding to apoA-II promoter sequences –65 to –33 (element AB; 847 to 879 of SEQ ID NO:11) identified two protein-DNA complexes that formed in rat liver nuclear extracts. Further studies revealed that the binding activity responsible for one of these complexes is heat-labile after treatment at 85° C. for 5 minutes, while the other is heat stable. The heat-labile binding activity is designated AIIAB1; the heat-stable activity is likely to be identical to factor CIIIB1, which we identified as a transcriptional regulator of the apoCIII gene. See the discussion of apoCIII promoter element B below for a description of our analyses of factor CIIIB1 and its role in regulating transcription of the apoA-II and apoCIII genes.

We investigated the relationship of AIIAB1 to known DNA-binding factors by performing competitor gel shift assays with competitor oligonucleotides that contain binding sites for known transcription factors. AIIAB1 binding was competed out by an oligonucleotide (SEQ ID NO:39) containing apoCIII promoter sequences –92 to –67 (1320 to 1345 of SEQ ID NO:14, including element B) and by an oligonucleotide (SEQ ID NO:18) containing α1-antitrypsin promoter region –130 to –93. The apoCIII (–92 to –67) competitor oligonucleotide contains binding sites for two known protein factors, CIIIB1 (see discussion of apoCIII promoter element B) and NF-BA1 (see discussion of apoB promoter element E).

AIIAB1 can be distinguished from CIIIB1, as mentioned above, on the basis of, for example, heat-stability: AIIAB1 activity is heat-labile while CIIIB1 activity is heat-stable to treatment at 85° C. for 5 minutes. AIIAB1 can be distinguished from NF-BA1 on the basis of, for example, gel shift complex mobility; the NF-BA1-DNA runs faster in a gel-shift assay than does the CIIIB1-DNA complex, whereas the AIIAB1-DNA complex runs more slowly than does the CIIIB1 complex.

We further found that AIIAB1 is not identical to C/EBP, which also binds to the apoA-II promoter element AB, because the electrophoretic mobility of the C/EBP-DNA gel shift complex formed on an oligonucleotide probe containing apoA-II sequences −65 to −33 (element AB) is faster than that of the AIIAB1-DNA complex. We therefore conclude that factor AIIAB1 represents a novel DNA binding activity.

We have performed purification studies of factor AIIAB1. AIIAB1 activity eluted from a Q-Sepharose column at approximately 0.2M KCl, from a Bio-Rex 70 at approximately 0.4M KCl, and from an S-Sepharose column at approximately 0.3M KCl. Partially purified AIIAB1 may be further purified by sequence specific DNA affinity chromatography using a column containing a concatemerized double stranded oligonucleotide corresponding to apoA-II promoter sequences −65 to −33 (element AB; 847 to 879 of SEQ ID NO:11) as a ligand.

Element D

Gel shift experiments using a double stranded oligonucleotide probe corresponding to apoA-II promoter sequences −276 to −255 (element D; 636 to 657 of SEQ ID NO:11) revealed that incubation of this probe with a rat liver nuclear extract results in production of a broad band corresponding to at least three superimposed protein-DNA complexes, designated AIID1, AIID2, and AIID3. Further experiments revealed that AIID1 and AIID2 are heat-labile activities that are inactivated by treatment at 85° C. for five minutes. AIID3 activity is stable to such heat treatment.

AIID1, AIID2, and AIID3 binding activities were first separated by column chromatography. Briefly, AIID1 and AIID2 were separated from AIID3 by Q-Sepharose anion exchange chromatography. AIID1 and AIID2 both eluted from this column at approximately 0.3M KCL; AIID3 eluted at 0.2M KCl. AIID1 and AIID2 were then separated from each other by cation exchange chromatography on a BioRex 70 column, from which AIID1 eluted at approximately 0.4M–0.5M KCl and AIID2 eluted at approximately 0.2M KCl. An additional activity, designated AIID4, eluted from the BioRex 70 column at approximately 0.3M KCl. AID4 activity is heat-labile to treatment at 85° C. for five minutes.

AIID2 and AIID4 have been further purified using sequence specific DNA affinity chromatography with the apoA-II element D (−276 to −255; 636 to 657 of SEQ ID NO:11) oligonucleotide probe. SDS-Page analysis of affinity-purified AIID2 revealed three predominant polypeptide bands, labelled α, β, and γ, that have apparent molecular weights of approximately 54 kDa, 59 kDa, and 63 kDa, respectively. SDS-PAGE analysis of affinity-purified AIID4, that had been purified by three successive rounds of affinity chromatography, revealed enrichment of three predominant polypeptide bands, labelled α, β, and γ, that have an apparent molecular weight of approximately 31 kDa, 66 kDa, and 130 kDa, respectively.

We have investigated the relationship of factors AIID1, AIID2, and AIID3 to known transcription factors using DNA binding and competition analysis. We have found that the AIID3 complex is competed out by oligonucleotides containing binding sites for C/EBP (SEQ ID NO:27), NF1 (SEQ ID NO:46), NFY (SEQ ID NO:24), AP1 (SEQ ID NO:48), AP2/3 (SEQ ID NO:49), α1AT (SEQ ID NO:18), and OTF (SEQ ID NO:50), and by oligonucleotides corresponding to apoB element IV, apoA-II elements AB (SEQ ID NO:51), C (SEQ ID NO:53), F (SEQ ID NO:56), G (SEQ ID NO:57), and L (SEQ ID NO:63), apoCIII elements C (SEQ ID NO:40) and D (SEQ ID NO:20), and albumin ( (SEQ ID NO:47) Maire et al.; DeSimone et al.; Bos et al.; Mitchell et al.; Scheidereit et al.). These results suggest that the AIID3 complex may result from DNA binding by C/EBP-related factors.

The AIID1 complex is competed out by oligonucleotides containing apoA-I promoter element C and apoCIII promoter element C, as well as by the oligonucleotide TKC/EBP (Dorn et al. Cell 50:863–872, 1987).

The AIID2 complex is not competed out by any of the oligonucleotides we tested (see Table 3 and Cardot et al. Biochemistry 32:9080–9093, 1993).

Element D of the apoA-II promoter is also recognized by factors NF-BA2 and NF-BA3, which we identified as regulators of apoB transcription (see discussion of apoB elements I, IV, V, and E). Protein factors AIID1, AIID2, and AIID4 can be distinguished from NF-BA2 and NF-BA3 on the basis of, for example, stability to heat inactivation. AIID1, AIID2, and AIID4 activities are heat labile to treatment at 85° C. for five minutes, whereas NF-BA2 and NF-BA3 activities are stable to such treatment. AIID3 may be similar to NF-BA2 and NF-BA3.

Element D of the apoA-II promoter is also recognized by heat labile factor CIIIC1 (see discussion of apoCI promoter element C). AIID1, AIID2, and AIID4 can be distinguished from CIIIC1 on the basis of, for example, competition of binding activity with various competitor oligonucleotides (see Table 3).

Element J

DNA binding and competition experiments have revealed that apoA-II element J is bound by the same factors that bind to apoA-I element D, which factors also recognize apoB element III and apoCIII element B (see discussion of apoA-I element D).

We evaluated the transcriptional significance of factor binding to element J by studying the effects of element J deletion on expression of a CAT reporter construct. We found that deletion of element J reduced hepatic and intestinal transcription to 70% and 32% of control levels, respectively. This result indicates that the observed binding by ARP-1, EAR-2, and EAR-3 is unlikely to have physiological significance since those factors function as transcriptional repressors (see Ladias et al. J. Biol. Chem 267:15849–15860, 1992; and example 5).

Element K

Similar DNA binding and competition analyses as those described for apoA-II element AB revealed that factors AIIAB1 and CIIIB1 bind to apoA-II element K (−760 to −743; 152 to 169 of SEQ ID NO:11). Purified C/EBP does not bind to this element. The competition analyses further revealed that the CIIIB1 protein factor probably also recognizes apoA-II promoter element L.

Element L

As mentioned above, competition DNA binding experiments performed to analyze protein factors that recognize element K of the apoA-II promoter revealed that factor CIIIB1 probably also recognizes apoA-II promoter element L.

Gel shift experiments performed with a double stranded oligonucleotide probe corresponding to apoA-II promoter sequences −803 to −773 (element L; 109 to 139 of SEQ ID NO:11) revealed that multiple protein-DNA complexes, designated AIIL1–9, are formed when that probe is incubated with rat liver nuclear extracts.

Competition experiments and mobility comparisons with known factors indicated that (i) the AIIL3 shift is competed out with oligonucleotides containing the binding site for NFY; (ii) the mobility of the AIIL4 shift corresponds to the mobility of a partially-purified CIIIB1-DNA shift; (iii) complexes AIIL5, AIIL6, AIIL7, and AIIL8 are competed out with oligonucleotides containing the DNA binding sites for DBP, C/EBP, and/or NFY, and by oligonucleotides containing apoB sequences −78 to −48 (41 to 71 of SEQ ID NO:12, including element IV) and apoA-I promoter sequences −175 to −148 (element C; 59 to 86 of SEQ ID NO:10); (iv) partially purified NF-BA3 (see discussion of apoB promoter elements I, IV, V, and E) forms a protein-DNA complex with mobility similar to that of AIIL7; (v) bacterially produced C/EBP forms a gel shift complex with the apoA-II element L (−803 to −773; 109 to 139 of SEQ ID NO:11) probe whose mobility is slower than that of any of the complexes AIIL1–9; and (vi) the AIIL9 complex is competed out with an oligonucleotide containing the binding site for HNF1/LFB1.

The results of these analyses indicated that apoA-II promoter element L, in addition to being recognized by factor CIIIB1, is also recognized by factors that bind to the CCAAT motif (e.g. NFY, C/EBP, NF-BA2, NF-BA3 etc.) NF-BA2 and NF-BA3 are transcription factors that we identified as regulators that bind to apoB promoter elements I, IV, V and E (see below). CIIIB1 can be distinguished from NF-BA2 and NF-BA3 on the basis of, for example, binding specificity and gel shift complex mobility.

We were able to correlate CCAAT-factor binding with transcriptional activity by introducing mutations in element L that interfered with CCAAT-factor binding into a CAT reporter construct. We found that deletion of element L, which eliminated binding by all element L-binding factors, reduced hepatic and intestinal transcription to 20–25% of control levels. Nucleotide substitution mutation LM1, which affected binding by NFY to apoA-II element L, reduced both hepatic and intestinal transcription to 30% of control levels. These results, when combined with our results for mutations that disrupt CIIIB1 binding to apoA-II promoter element L (see discussion of apoCIII promoter element B), indicated that CIIIB1 and NFY1 act synergistically to regulate transcription of the apoA-II gene.

Element M

Gel shift analysis using a double stranded oligonucleotide probe corresponding to apoA-II promoter sequences −853 to −829 (element M; 59 to 83 of SEQ ID NO:11) revealed that two predominant complexes, designated AIIM1 and AIIM2, form when this probe is incubated with rat liver nuclear extracts. The AIIM1 complex, but not the AIIM2 complex also forms when this probe is incubated with extracts from CaCo2 intestinal cells. The AIIM1 and AIIM2 activities were heat-labile to treatment at 85° C. for five minutes.

We compared the DNA binding properties of AIIM1 and AIIM2 with those of known DNA binding factors using gel shift competition assays. We determined that neither the AIIM1 nor the AIIM2 complex is competed out by oligonucleotides containing the binding sites for C/EBP, NF1, HNF1/LFB1, or NFY, or by oligonucleotides containing apoB promoter elements HI, IV, or V, apoA-I promoter element D, or apoCIII promoter element D, albumin promoter element D, or α1-antitrypsin promoter sequences. These results suggest that AIIM1 and AIIM2 represent novel DNA-binding activities.

We further determined, using a CAT reporter construct, that deletion of element M from the apoA-II promoter reduces intestinal transcription to 30% of control levels, but has no effect on hepatic transcription. This results indicates that binding by factor AIIM4 is important for intestinal transcription of the apoA-II gene, but may not be important for hepatic transcription.

Element N

Gel shift reactions in which a double-stranded oligonucleotide probe corresponding to apoA-II promoter sequences −903 to −879 (element N; 9 to 33 of SEQ ID NO:11) was incubated with a rat liver nuclear extract yielded a single predominant gel shift complex, designated AIIN3, and two minor complexes, designated AIIN1 and AIIN2. AIIN3 activity was heat-labile to treatment at 85° C. for five minutes.

We investigated the relationship of AIIN3 to known protein factors by performing gel shift competition experiments with competitor oligonucleotides that contain binding sites for known transcription factors. We found that AIIN3 binding was not competed out by oligonucleotides containing the binding site for NF-1 (Maire et al. Science 244:343–346, 1989) or NF-Y (Maire et al. id), or by oligonucleotides corresponding to apoA-I promoter sequences −218 to −188 (12 to 46 of SEQ ID NO:10, including element D), apoB promoter sequences −88 to −62 (31 to 57 of SEQ ID NO:12, including element D), apoCIII promoter sequences −160 to −142 (element D; 252 to 270 of SEQ ID NO:14), $\alpha_1$-antitrypsin promoter sequences −122 to −101. This result indicated that the AIIN3 protein factor is distinct from protein factors that recognize a binding site in the competitor oligonucleotides we tested.

We found that AIIN3 binding was partially competed with an oligonucleotide containing the HNF1/LFB1 binding site from the albumin promoter (Frain et al. Cell, 59:145–157; Maire et al. Science 244:343–346). HNF1/LFB1 is known to retain its binding activity when heated to 85° C. We tested whether AIIN3 were similarly heat stable by performing gel shift assays on our element N (−903 to −879; 9 to 33 of SEQ ID NO:11) probe with rat liver nuclear extracts that had been heated to 85° C. for five minutes. AIIN3 binding activity was inactivated by this treatment. We therefore conclude that AIIN3 binding activity is heat labile and is not identical to HNF1/LBF1.

We further demonstrated that HNF1/LFB1 produced by vaccinia virus expression of the corresponding cDNA binds only weakly to our apoA-II element N (−903 to −879; 9 to 33 of SEQ ID NO:11) probe. HNF/LFB1 bound to this probe with one twentieth the affinity with which it binds to its site in the albumin promoter. This result is consistent with the idea that AIIN3 and HNF1/LBF1 are non-identical.

We determined the tissue distribution of the protein factors (AIIN3, AIIN2, and AIIN1) that bind to element N of the apoA-II promoter by comparing the results of gel shift assays performed in nuclear extracts from cells that do (HepG2 and CaCo2) and do not (HeLa) express our apoA-II/CAT fusion construct. We found that AIIN3 activity is abundant in HepG2 liver extracts and CaCo2 intestinal extracts, but is absent from HeLa extracts. AIIN1 activity showed a similar profile. AIIN 2 activity, which was minor in HepG2 liver extracts, was abundant in CaCo2 intestinal extracts and was the only activity observed in HeLa extracts.

We performed methylation interference analysis of the AIIN3 complex and determined that G residues at −890, −883, −881, and −879 of the noncoding strand and −888 of the coding strand participate in formation of the DNA-protein complex. Other residues within element N (−903 to −879; 9 to 33 of SEQ ID NO:11) may also contribute to complex formation.

Our promoter deletion studies described above indicated that deletion of sequences between −911 and −860 (2 to 52 of SEQ ID NO:11, including element N) of the apoA-II promoter drastically reduced both hepatic and intestinal transcription from the apoA-II promoter (to 7% and 18% of control levels, respectively). As AIIN3 is the predominant binding activity that recognizes apoA-II element N, we conclude that factor AIIN3, when bound to element N, is likely to be a transcriptional activator of the apoA-II gene in both hepatic and intestinal cells.

We have attempted to purify factor AIIN3 and have found it to be unstable to fractionation on a variety of cation and anion exchange columns.

ApoB

Apolipoprotein B (apoB) plays a major role in the regulation of cellular cholesterol homeostasis and the pathogenesis of atherosclerosis (see Brunzell et al. Arteriosclerosis 4:79–83, 1984; Heiss et al. Proc. on. Wkshp. Apolip. Quant., Pub. 83–1266, 7–24, U.S. Dept. of HHS, NIH, Bethesda, Md., 1982; Kannel et al. Ann. Intern. Med. 90; 85–91, 1982; Sniderman et al. Proc. Natl. Acad. Sci. U.S.A. 77: 604–608, 1980; and Zannis et al. Curr. Op. in Lipidology 3: 96–113, 1992 and references therein). It is the protein part of the low density lipoprotein particle that serves as a ligand for the recognition and catabolism of plasma low density lipoprotein by the low density lipoprotein receptor. The primary structure of human apoB has been studied by cDNA and gene cloning and by direct protein sequencing. ApoB mRNA has been detected in the liver, intestine, and placenta, indicating that apoB gene transcription is regulated in a tissue-specific manner (see Cladaras et al. Biochemistry 25: 5351–5357, 1986; Demmer et al. Proc. Natl. Acad. Sci. U.S.A. 83: 8102–8106, 1986).

Prior to our work, mutational studies by Das et al. (J. Biol. Chem. 1988 263, 11452) identified positive and negative regulatory regions involved in liver-specific transcription of the apoB gene. In particular, Das et al. found evidence for a series of negative regulatory elements located between −900 and −670, −261 and −152, and −138 and −128 relative to the transcription start site, and positive regulatory elements located between −128 and −86 and between −86 and −70.

Using gel mobility shift studies, Das et al. identified at least five protein-DNA complexes of distinct electrophoretic mobilities that could form in nuclear extracts from hepatoma (HepG2) cells on sequences between −128 and +122. Das et al. found that two of the complexes required sequences between −86 and −70, while three complexes required sequences between −83 to −62. DNaseI footprinting experiments identified a single protected region extending from −83 to −62 that is protected in HepG2 nuclear extracts. The protein factors responsible for the protection, and the exact DNA sequences that they recognized, were not identified. Das et al. did not observe protein binding was observed in the −128 to −86 region.

Kardassis et al. have also investigated the transcriptional regulatory sequences of the apoB promoter and have found that strong regulatory elements capable of directing tissue-specific expression of the apoB gene are located on a promoter fragment that extends from approximately nucleotides −150 to +124 (Mol. Cell. Biol. 10:2653–2659, 1990). Kardassis et al. (id identified four protected sequence regions, designated C (−124 to −100), B (−97 to −93), A (−86 to −33), and E (+33 to +52), in DNaseI footprinting assays in extracts from rat liver and human HepG2 cells, and found that at least nine protein—DNA complexes could form on a doublestranded oligonucleotide probe including region A incubated in rat liver nuclear extracts. Kardassis et al. (id) further found that a single shifted species can be detected with a probe including −88 to −62 (probe BA1; SEQ ID NO:41), several shifted species' that are not easily resolved can be detected with a probe including −61 to −36 (probe BA2; SEQ ID NO:42), and at least five shifted species' can be detected with a probe including −78 to −48 (probe BA3; SEQ ID NO:43). Kardassis et al. (id identified the exact binding motif (5'-GCGCCTITGGACCTTT-3', found between −79 and −63 of the apoB promoter, corresponding to 40 to 56 of SEQ ID NO:12) of the protein factor responsible for the single gel shift species observed with probe BA1 (−88 to −62; SEQ ID NO:41). However, Kardassis et al. (id) did not identify that protein factor, or any other protein factor that recognizes DNA sequences within the apoB promoter (between 40 and 56 of SEQ ID NO:12) region.

In the present invention, we describe full characterization of five regulatory sequences (I–V) between −150 and +8 that are involved, along with the downstream element E (+33 to +52; SEQ ID NO:13), in transcriptional regulation of the apoB gene. We further describe the identification, characterization, and purification of new protein factors, NF-BA2, NF-BA3, BCB1, BCB2, BCB3, NF-BA1, that bind to regulatory sequences of the apoB promoter. We have purified the factor, NF-BA1, that binds between −79 and −63 of the apoB promoter to homogeneity. For detailed procedures used in our studies of the apoB promoter, see Example 3. The results of our investigations are summarized in FIG. 3. We have found that synergistic action of protein factors that bind to elements in the apoB promoter and stimulate transcription probably controls the expression of the apoB gene in hepatic and intestinal cells.

Promoter mapping studies

To define the exact regulatory elements within the apoB promoter region, we performed DNaseI footprinting competition experiments in rat liver nuclear extracts with the apoB promoter fragment −268 to +8 in the presence of one or more of the same three double-stranded oligonucleotide probes, BA1 (−88 to −62; SEQ ID NO:41), BA2 (−61 to −36; SEQ ID NO:42), and BA3 (−78 to −48; SEQ ID NO:43), used by Kardassis et al. 1990 (supra) and/or a fourth probe, BC1 (−116 to −99; SEQ ID NO:44) (Kardassis et al. J. Biol. Chem. 267:2622–2632, 1992, incorporated herein by reference). These experiments revealed that regions A (−86 to −33; 33 to 86 of SEQ ID NO:12) and BC (−124 to −93) contain five overlapping regulatory elements that are the binding sites for protein factors, the approximate boundaries of which are:

I: −118 to −98 (1 to 21 of SEQ ID NO:12)
II: −112 to −94 (7 to 25 of SEQ ID NO:12)
III: −86 to −62 (33 to 57 of SEQ ID NO:12)
IV: −72 to −53 (47 to 66 of SEQ ID NO:12)
V: −53 to −33 (66 to 86 of SEQ ID NO:12)

As will be discussed further below, we have identified and, in some cases have purified, protein factors that bind to these elements and to element E (+33 to +52; SEQ ID NO:13). The transcriptional significance of these sequence elements, and of the proteins that bind to them has also been investigated.

Elements I, IV, V, and E

DNaseI competition footprinting analysis revealed that there is simultaneous deprotection of sequences in elements I, IV, and V. Element IV includes the sequence 5'-GCAAT-3' at position −62 to −58 (57 to 61 of SEQ ID NO:12), which sequence has been shown to be important for the binding of the enhancer-binding protein C/EBP (Landschultz et al. Science 245:1681–1688, 1989); elements I and V contain the sequences 5'-CCAGT-3' and 5'-GCAAG-3', which differ from the C/EBP consensus at no more than two positions. Element E also contains a related sequence, 5'-GCAAC-3'.

We therefore expressed C/EBP in bacteria and tested its ability to interact with elements I, IV, V, and E. We found that bacterially-expressed C/EBP retards double-stranded oligonucleotides corresponding to element I (oligonucleotide BC1: −116 to −99; SEQ ID NO:44), element IV (oligonucleotide BA4: −72 to −54; SEQ ID NO:68), element IV (oligonucleotide BA2: −61 to −36; SEQ ID NO:42), and element E (oligonucleotide BE: +31 to +52; SEQ ID NO:69) in a gel-shift assay, indicating that C/EBP can bind to sequence elements I, IV, V, and E.

C/EBP is not the only protein factor that can bind to these sequence elements.

As mentioned above, Kardassis et al. 1990 had observed that a least five protein-DNA complexes can form on probe BA3 (−78 to −48; SEQ ID NO:43) when it is incubated in a rat liver nuclear extract (Kardassis et al. 1990 supra. Binding of C/EBP alone cannot account for all five of these complexes. In order to investigate whether the observed DNA-protein complexes result from binding of distinct protein factors to the BA3 (−78 to −48; SEQ ID NO:43) probe, and to identify any factors other than C/EBP that recognize the BA3 (−78 to −48; SEQ ID NO:43) probe, we fractionated rat liver nuclear extracts as described in Example 3.

In brief, nuclear extracts were first heated at 85° C. for five minutes. Heated nuclear extracts retained the ability to form five DNA-protein complexes with probe BA3 (−78 to −48; SEQ ID NO:43), as observed with native extracts. This result indicated that the protein factors responsible for the observed DNA-protein complexes are heat-stable, at least to five minute treatment at 85° C.

Heat treated extracts were then fractionated on a Bio-Rex 70 column. We observed specific DNA-protein complexes on the BA3 (−78 to −48; SEQ ID NO:43) probe were observed in Bio-Rex 70 fractions eluting at 0.3–0.5M KCl. Two predominant complexes with mobilities distinct from that of the C/EBP-BA3 complex, and therefore presumably formed by proteins other than C/EBP, were formed by proteins that eluted in the 0.4M KCl fraction.

The protein factors responsible for these two gel-shift complexes were further resolved by chromatography on a Mono-S FPLC column using a shallow linear gradient of 0.2–0.6M KCl. One binding activity, designated NF-BA2 peaked in two fractions eluted at approximately 0.4M KCl. The other binding activity, designated NF-BA3, peaked in two fractions eluted at approximately 0.45M KCl. NF-BA2 and NF-BA3 were further purified on a small scale using sequence specific DNA affinity chromatography with a concatenated double stranded oligonucleotide corresponding to apoB sequences −75 to −45.

Gel shift and DNaseI footprinting experiments revealed that NF-BA2 and NF-BA3, like C/EBP, can bind to probes BC1 (−116 and −99; SEQ ID NO:44), BA4 (−72 to −54; SEQ ID NO:68), BA2 (−61 to −36; SEQ ID NO:42), and BE (+31 to +52; SEQ ID NO:69), corresponding to sequence elements I, IV, V, and E, respectively of the apoB promoter. In all cases, the C/EBP-probe shift migrated most slowly, followed by the NF-BA2-probe shift and then the NF-BA3-probe shift. C/EBP, NF-BA2, and NF-BA3 all protect sequence element I (−118 to −98; 1 to 19 of SEQ ID NO:12), sequence element IV (−72 to −53; 47 to 66 of SEQ ID NO:12), and sequence element V (−53 to −33; 66 to 86 of SEQ ID NO:12) from attack by DNaseI, but the different protein factors show different affinities for individual sequence elements. For example, C/EBP binds strongly to probe BA4 (−72 to −54; SEQ ID NO:68), corresponding to element IV. C/EBP binds to probe BA2 (−61 to −36; SEQ ID NO:42), corresponding to element V, and to probe BC1 (−116 to −99; SEQ ID NO:44), corresponding to element I, with one fifth and one-tenth, respectively, of the affinity with which it binds to probe BA3 (−78 to −48; SEQ ID NO:43), corresponding to element IV. Thus, for C/EBP, the template specificity follows the order element IV>element V>element I. By contrast, the template specificity of factor NF-BA3 follows the order element IV>element I>element V. In addition, higher amounts of oligonucleotides BA4 (−72 to −54; SEQ ID NO:68), BC1, (−116 to −99; SEQ ID NO:44), and BA2 (−61 to −36; SEQ ID NO:42) are required to compete for the same levels of NF-BA3, as compared with C/EBP, which indicates that NF-BA3 has higher affinity for sequence elements I, IV, and V than does C/EBP. The higher binding affinity displayed by NF-BA3 relative to C/EBP makes it very likely that protein factor NF-BA3 plays an important role in the regulation of apoB transcription in hepatic cells.

NF-BA2 and NF-BA3 also bind to element C (−175 to −148; 59 to 86 of SEQ ID NO:10) of the apoA-I promoter, to elements C (−126 to −110; 786 to 802 of SEQ ID NO:11), D (−276 to −255; 636 to 657 of SEQ ID NO:11), and L (−803 to −773; 109 to 139 of SEQ ID NO:11) of the apoA-II promoter, and to element CD (−160 to −119) of the apoCIII promoter.

We were able to correlate the ability of factors C/EBP, NF-BA2, and NF-BA3 to bind to sequence element with the level of transcription of the apoB gene. Specifically, Kardassis et al. 1990 supra had shown that a mutation that changed the C/EBP recognition sequence 5'-GCAAT-3', found at −62 to −58 of element IV, to 5'-GATAT-3', reduced the hepatic and intestinal transcription of the apoB gene to 13% and 9%, respectively, of the control level. We performed gel shift assays with an oligonucleotide probe, BM6, that contained the same mutation and found that none of C/EBP, NF-BA2, nor NF-BA3 could bind to the mutated element. This result confirms that NF-BA2 and NF-BA3 recognize the same sequence, 5'-GCAAT-3', that is recognized by C/EBP and that NF-BA2 and NF-BA3 may be part of a family of C/EBP-like DNA binding proteins. The result also indicates that the binding by protein factors to element IV is likely to be important for full expression of the apoB gene, that is, that C/EBP, NF-BA2, and NF-BA3 are likely to be activators of apoB gene transcription.

Element II

We investigated the binding activities responsible for protection of element II (−112 to −94; 7 to 25 of SEQ ID NO:12) of the apoB promoter by performing gel shift assays in rat liver nuclear extracts with a double-stranded oligonucleotide probe, termed BCB (SEQ ID NO:70), that includes apoB sequences −115 to −86 (4 to 23 of SEQ ID NO:12). We observed three predominant complexes, termed BCB1, BCB2, and BCB3, that are not competed by a nonspecific oligonucleotide, by oligonucleotides BC1 (−116 to −99; SEQ ID NO:44), BA1 (−88 to −62; SEQ ID NO:41), BA2 (−61 to −36; SEQ ID NO:42), or BA3 (−78 to −48; SEQ ID NO:43), nor by a variety of other oligonucleotides whose binding activities have been well defined (see Table 5) The BCB1, BCB2, and BCB3 activities were heat-labile to treatment at 85° C. for five minutes.

To determine whether the observed complexes resulted from interaction of distinct proteins with the BCB probe, we fractionated rat liver nuclear extracts on a heparin-Sepharose column. A binding activity that gives rise to a protein-DNA complex with the same mobility as the BCB2 band remained in the flow through fraction (approximately 40 mM KCl, whereas binding activities that give rise to complexes with the same electrophoretic mobilities as the BCB3 and BCB1 bands eluted at approximately 0.4M and 0.5M KCl, respectively. This indicates that BCB1, BCB2, and BCB3 may represent distinct protein factors that can interact with the BCB (−115 to −86; SEQ ID NO:70) probe. The BCB1, BCB2, and BCB2 protein factors can be further purified by sequence specific DNA affinity chromatography using a concatenated double-stranded oligonucleotide corresponding to apoB element II sequences −112 to −94; 7 to 25 of SEQ ID NO:12 as a ligand.

We next investigated the possibility that the BCB1, BCB2, and BCB3 protein factors could be distinguished from each other on the basis of the exact nucleotide sequences that they recognize. For this analysis, we used oligonucleotides containing substitution mutations within the BCB region (−115 to −86; SEQ ID NO:70), the sequences of which are presented in Table 6. DNA binding by the factors that give rise to the BCB1, BCB2, and BCB3 complexes is abolished for mutant oligonucleotides LM4 (SEQ ID NO:74), LM5 (SEQ ID NO:75), LM6 (SEQ ID NO:76), LM9 (SEQ ID NO:79), LM13 (SEQ ID NO:83), and LM15 (SEQ ID NO:85). By contrast, all three complexes still formed, with reduced affinity, with the previously-described (Kardassis et al. 1990 supra) mutants LM2 and LM3. Complexes with different electrophoretic mobilities from those of BCB1, BCB2, and BCB3, formed with mutants LM7 (SEQ ID NO:77), LM8 (SEQ ID NO:78), and LM14 (SEQ ID NO:84). Competition with oligonucleotides BCB (−115 to −86 (SEQ ID NO:70)) or BC1 (−116 to −99 (SEQ ID NO:44) did not eliminate the formation of these new complexes, indicating that these complexes represent binding of factors that are unrelated to the BCB1, BCB2, and BCB3 factors. Mutations downstream of nucleotide −94 (LM10 [SEQ ID NO:80], LM11 [SEQ ID NO:81] and LM12 [SEQ ID NO:82]) and mutations upstream of −106 (LM16 [SEQ ID NO:86] and LM17 [SEQ ID NO:87]) had no effect on the formation of the BCB1, BCB2, and BCB3 complexes. These results indicate that the BCB1, BCB2, and BCB3 protein factors probably recognize the same nucleotide sequence. In particular, it appears that the sequence 5'-AAAAGCAAACAG-3', which is found between −106 and −95 (13 to 24 of SEQ ID NO:12), is important for formation of all three BCB complexes.

We investigated the transcriptional significance of DNA binding by the BCB1, BCB2, and BCB3 protein factors by introducing some of the same substitution mutations into a CAT expression plasmid and assaying activity after transfection into HepG2 cells. The LM5 and LM6 mutations that abolish the formation of all three BCB complexes also reduced transcription of the reporter construct to 9.5% and 8.5% of control levels, respectively. By comparison, the LM2 and LM3 mutations that reduce, but do not eliminate, formation of all three BCB complexes reduce expression of a linked reporter gene to 20–30% of control levels (Kardassis et al. 1990 supra). Our results indicate that DNA binding by the BCB protein factors is likely to be important for transcription of the apoB gene in hepatic cells. That is, the BCB1, BCB2, and BCB3 protein factors are likely to be transcriptional activators of apoB transcription.

Element III

As mentioned above, Kardassis et al. (1990, supra) had identified a protein factor that binds to a motif (5'-GCGCCTlTGGACCTTT-3') that is found between −79 and −63 of the apoB promoter (between 40 and 56 of SEQ ID NO:12) and also binds upstream of several other apolipoprotein genes. In order to understand the function of this factor, which we designate NF-BA1, in transcriptional regulation of the apoB gene, we worked out a purification scheme that allowed us to purify NF-BA approximately 16,000 fold to apparent homogeneity (Kardassis et al. J. Biol. Chem. 265:21733–21740, 1990, incorporated herein by reference). The scheme involved fractionation on Q-Sepharose, Bio-Rex 70, S-Sepharose, and DNA affinity columns, as described in Example 3. The activity of NF-BA1 was monitored throughout the purification by a DNA-binding gel electrophoresis ("gel shift") assay using probe BA2 (SEQ ID NO:42), corresponding to ApoB sequences −88 to −62 (31 to 57 of SEQ ID NO:12). NF-BA1 activity was beat-labile to treatment at 85° C. for five minutes.

In brief, our purification scheme involved applying nuclear extracts to a Q-Sepharose anion exchange column at approximately 0.04M KCl and eluting bound proteins with a linear gradient of 0.04M to 0.3M KCl, or alternately with a step gradient with 0.1M, 0.2M, 0.3M, 0.3M, and 1.0M KCl steps. The majority the NF-BA1 activity eluted gradient versus a linear gradient did not appear to affect the yield or the levels of the minor contaminants in the final preparation. The active fractions eluted from the Q-Sepharose column were pooled and chromatographed on a cation-exchange Bio-Rex 70 column, from which the NF-BA1 activity eluted at approximately 0.4M KCl. More than 60% of the total activity was recovered from the Bio-Rex 70 column. Further purification (approximately eight-fold) was achieved by chromatography on an S-Sepharose column. NF-BA1 activity eluted from this column at approximately 0.3M KCl, resulting in a recovery of approximately 54%.

The final purification step involved a sequence-specific DNA affinity column. A double-stranded oligonucleotide probe, corresponding to apoB sequences −80 to −63 (39 to 56 of SEQ ID NO:12) within element III, was self-ligated to produce concatenated DNA molecules containing an average of 15 copies of the original probe. The concatenated DNA was attached covalently to cyanogen-bromide activated Sepharose beads to make a sequence-specific DNA affinity column. The 0.3M fraction from the S-Sepharose column, which contained the peak NF-BA1 activity, was chromatographed on this sequence-specific DNA affinity column, from which the NF-BA1 activity eluted at approximately 0.5M KCl. The NF-BA1 factor was further purified by two additional cycles of the DNA-specific affinity chromatography.

Our entire purification procedure resulted in about 16,000 fold purification of NF-BA1 with an overall yield of about 33%. Based on this yield and the total amount of protein extracted per nucleus (20 pg), we estimate that there are approximately 13,000 NF-BA1 molecules per rat liver nucleus.

The purified NF-BA1 protein has a molecular mass of approximately 60 kDa, as estimated from SDS-polyacrylamide gel electrophoresis (SDS-PAGE) of column fractions and of the components of an NF-BA1 gel-shift band excised from a preparative DNA-binding gel. We confirmed this molecular weight estimate by radioactively labelling purified NF-BA1 in vitro through photoactivated crosslinking to a $^{32}$P-labelled BA1 (−88 to −62; SEQ ID NO:41) probe containing 5 bromodeoxyuridine residues and analyzing the crosslinked complex by SDS-PAGE. The crosslinked complex had an apparent molecular weight of approximately 67 kDa, approximately 7 kDa of which presumably reflect the presence of the crosslinked DNA sequence.

We further analyzed the purified NF-BA1 protein by examining its ability to protect element III of the apoB promoter from attack by DNaseI. We found, as expected, that purified NF-BA1 protects apoB sequences between −79 and −63. We further found that purified NF-BA1 can footprint sequences within apoAI element D (−212 to −191; 22 to 53 of SEQ ID NO:10), apoA-II element J (−740 to −719; 172 to 193 of SEQ ID NO:11), and apoCIII element B (−87 to −63; 1325 to 1349 of SEQ ID NO:14). Gel shift analysis confirmed the ability of purified NF-BA1 to bind to these regions. It therefore seems possible that NF-BA1 plays a role in transcriptional regulation of apoA-I, apoA-II, and apoCIII as well as of apoB.

Methylation interference studies showed that G resides at −78, −71, and −70 of the coding (sense) strand and −76, −75, and −68 of the non-coding (antisense) strand are important for NF-BA1 binding to apoB promoter element III.

We examined the transcriptional properties and DNA binding requirements of the purified NF-BA1 protein using an in vitro transcription-complementation system.

We assayed transcription of in vitro templates in which the −268 to +8 apoB promoter fragment was fused to a G-minus cassette (Lue et al. Proc. Natl. Acad. Sci. 84:8839–8843, 1987). Control templates contained the Adenovirus major late (AdML) promoter region −404 to +9 fused to a shorter G-minus cassette. Transcription from templates including the wild type apoB −268 to +8 fragment was compared with that from templates including the BM2 or BM3 mutations, which were previously described by Kardassis et al. (1990 supra) as mutations that abolish NF-BA1 binding to the BA1 (−88 to −62; SEQ ID NO:41) probe in rat liver nuclear extracts.

Templates containing the wild type apoB −268 to +8 promoter fragment are transcribed efficiently in in vitro reactions containing native rat liver nuclear extracts. The levels of in vitro transcripts observed with these templates decreases dramatically if the rat liver nuclear extracts are first depleted for NF-BA1 activity. In such reactions, addition of purified NF-BA1 restores transcriptional activity. Templates containing the BM2 or BM3 apoB promoter mutations yield greatly reduced levels of in vitro transcripts with native or NF-BA1-depleted rat liver nuclear extracts. Furthermore, the level of transcription observed with NF-BA1-depleted extracts is unaffected by the addition of purified NF-BA1. These results indicate, first of all, that NF-BA1 acts as a transcriptional activator of the apoB gene and, secondly, that purified NF-BA1 can stimulate transcription from the wild type apoB promoter but not from mutant promoters to which it does not bind.

We have used double-stranded competitor oligonucleotides in our in vitro transcription reactions to further demonstrate that interference with NF-BA1 binding inhibits transcription. For these experiments, we generated a "homopolymer" template containing five BA1 (−88 to −62) sites upstream of the core (−35 to +8) apoB promoter. This homopolymer promoter was as active as is the wild type apoB −268 to +8 promoter in our in vitro transcription reactions. Addition of oligonucleotide BA1 (−88 to −62; SEQ ID NO:41) to these in vitro transcription reactions inhibited transcription from both the homopolymer template and the wild type apoB −268 to +8 promoter template, presumably by interfering with NF-BA1 binding and therefore preventing NF-BA1 transcriptional activation. Transcription from the AdML control template was not affected in these experiments. These results indicate that the purified NF-BA1 protein stimulates transcription by specifically binding to its recognition sequence in element III of the apoB promoter and that interference with this binding disrupts NF-BA1 activation, thereby inhibiting transcription.

We have also investigated whether NF-BA1, or other protein factors capable of binding to element m of the apoB promoter, are present in other tissues and cells. We performed gel shift assays with the BA1 (−88 to −62; SEQ ID NO:41) probe in extracts from nuclei isolated from rat liver and spleen and cultured cells of hepatic (HepG2) and intestinal (Caco-2) origin. The single NF-BA1 binding activity observed in liver extracts was also found in HepG2 extracts. CaCo-2 extracts gave two complexes, one with higher and one with lower electrophoretic mobility as compared with the NF-BA1 complex observed in liver extracts. HeLa extracts gave two complexes of still different mobility. These observations suggest that element III of the apoB promoter may be recognized by structurally distinct factors in different cell types.

ApoCIII

Human apoCIII is a 79-amino acid protein of known primary structure and is a major component of very low density lipoprotein and a minor component of high density lipoprotein (see Zannis et al. Curr. Op. Lipidology 3:96–113, 1992; Zannis et al. Adv. Human Genet. 21:145–319, 1993; and references therein). The gene and cDNAs encoding human apoCIII have been isolated, mapped to the long arm of chromosome 11. ApoCIII has been implicated in the modulation of the catabolism of triglyceride-rich lipoproteins and thus may play some role in the development of hypertriglyceridemia. This concept is further supported by recent findings showing that overexpression of the apoCIII gene is associated with hypertriglyceridemia in transgenic mice (Ho et al. Science 299: 790–793, 1990). ApoCIII gene expression is tissue-specific and developmentally regulated (see Wu et al. J. Biol. Chem. 254: 7316–7322, 1979; Zannis et al. Biochemistry 24: 4450–4455, 1985; Lenich et al. J. Lipid Res. 29: 755–764, 1988; Haddad et al. J. Biol. Chem. 261: 13268–13277, 1986).

Previous studies have indicated that the regulatory elements which control hepatic and intestinal transcription of the human apoCIII gene are distributed in the −792 to −25 region of the apoCIII promoter (Reve et al. J. Biol. Chem. 263: 6857–6864, 1988; Leff et al. J. Biol. chem. 264: 16132–16137, 1989; Ogami et al. J. Biol. Chem. 265: 9808–9815, 1990). In particular, Ogami et al. 1990 (id) have defined ten regions within the apoCIII −1411 to +24 promoter region (SEQ ID NO:14) that are protected from DNaseI digestion in rat liver nuclear extracts. The approximate boundaries of the protected regions are:

A: −32 to −25 (1380 to 1387 of SEQ ID NO:14)
B: −87 to −72 (1325 to 1340 of SEQ ID NO:14)
C: −138 to −119 (1274 to 1293 of SEQ ID NO:14)
D: −160 to −142 (1252 to 1270 of SEQ ID NO:14)
E: −414 to −403 (998 to 1009 of SEQ ID NO:14)
F: −611 to −592 (801 to 820 of SEQ ID NO:14)
G: −669 to −648 (743 to 764 of SEQ ID NO:14)
H: −705 to −690 (707 to 722 of SEQ ID NO:14)
I: −766 to −726 (646 to 686 of SEQ ID NO:14)
J: −792 to −799 (620 to 613 of SEQ ID NO:14)

Ogami et al. 1990 (id) found that the region −890 to −686 (elements H, I, and J; 522 to 724 of SEQ ID NO:14) is recognized by protein factors that promote both intestinal and hepatic transcription, whereas the region −686 to −553 (part of element F and element G; 724 to 859 of SEQ ID NO:14) is recognized by factors that promote only hepatic transcription.

Ogami et al. 1990 (id) identified two distinct protein factors, CIIIB1 and CIIIB2, that bind to overlapping recognition sequences within element B. CIIIB2 is identical to factor NF-BA1 described above. Ogami et al. 1990 (id) found that DNA binding by CIIIB1 and NF-BA1 was mutually exclusive. Furthermore, they found that both factors activated ApoCIII transcription, although CIIIB1 activation was weaker.

We have purified the CIIIB1 protein approximately 6,800 fold to near homogeneity from rat liver nuclear extracts (Ogami et al. J. Biol. Chem. 266:9640–9646, 1991, incorporated herein by reference). Additionally, we have identified, characterized, and purified a new protein factor, designated CIIIC1, that binds to element CD of the apoCIII promoter. For detailed procedures used in our studies of the apoCIII promoter, see Example 4 and Example 2. The results of our investigations are summarized in FIG. 4.

Element B

As mentioned above, element B of the apo CIII promoter is bound by the same factors that recognize element D of the apoA-I promoter (and element J of the apoA-II promoter and element III of the apoB promoter), and by protein factor CIIIB1. Gel shift, purification, and mutational studies have indicated that CIIIB1 is distinct from the factors that recognize apoA-I promoter element D. Gel shift and methylation interference analyses further indicated that the CIIIB1 and NF-BA1 binding site within apoCIII promoter element B are overlapping.

We investigated the relationship of CIIIB1 to known protein transcription factors. We performed competition gel shift experiments in which CIIIB1 binding to a double stranded oligonucleotide probe, CIIIB(WT) (SEQ ID NO:39), that includes ApoCIII promoter sequences −92 to −67 (1320 to 1345 of SEQ ID NO:47) was challenged with double-stranded oligonucleotides containing binding sites for known transcription factors (see Table 7). For this analysis, we first partially purified CIIIB1 by heat treatment at 85° C. for five minutes, which inactivates NF-BA1 but not CIIIB1, followed by Bio-Rex 70 cation exchange chromatography. The results of these experiments indicated that CIIIB1 binding to the CIIIB(WT) (−92 to −67; SEQ ID NO:39) probe was not competed by oligonucleotides containing the binding sites for C/EBP (Maire et al. Science 244:343–346, 1989; Dorn et al. Cell 50:863–872, 1987), NF1 (Maire et al. supra, HNF1 (Maire et al. supra), NFY (Maire et al. supra), AP2 (Mitchell et al. Cell 50:847–861, 1987), OTF (Scheidereit et al. Cell 51:783–793), DBP (Maire et al. supra) or by the BA3 oligonucleotide (SEQ ID NO:43) containing sequences (−78 to −48) in element IV of the apoB promoter. The results therefore suggested that CIIIB1 is distinct from the protein factors whose binding sites we tested.

We further demonstrated that CIIIB1 is distinct from C/EBP by showing that bacterially-expressed C/EBP, which binds to an oligonucleotide (SEQ ID NO:41) containing a C/EBP site in the Albumin D −115 to −90 promoter region, does not bind to the CIIIB(WT) (−92 to −67; SEQ ID NO:39) probe.

To more fully characterize the CIIIB1 protein factor, we have purified it to near homogeneity from rat liver nuclear extracts using ion exchange and DNA affinity chromatography. In brief, nuclear extracts were fractionated on a Q-Sepharose column, from which the CIIIB1 activity eluted at 0.2M KCl, with a yield of approximately 54%. The active fractions eluted from Q-Sepharose were pooled and chromatographed on a Bio-Rex 70 column, from which the CIIIB1 activity eluted at 0.4M KCl, with a yield of over 52%. Further purification was achieved by stepwise elution of an S-Sepharose column at 0.2M, 0.3M, and 0.4M KCl. CIIIB1 activity eluted from S-Sepharose at approximately 0.3M KCl. The active S-Sepharose fraction was further purified through two cycles of sequence specific DNA affinity chromatography, using a double stranded oligonucleotide that contained a substitution mutation in apoCI promoter element B, which substitution mutation disrupted DNA binding by NF-BA1 but not by CIIIB1. CIIIB1 activity eluted from the sequence specific DNA affinity column at approximately 0.5M KCl with a yield of approximately 58%. The final purification step involved heat treatment at 85° C. for five minutes.

Our entire purification procedure resulted in approximately 6,800 fold purification of CIIIB1, with an overall yield of approximately 14.4%. Based on this yield and the total amount of protein extracted per nucleus (20 pg), we estimate that there are approximately 20,350 CIIIB1 molecules per rat liver nucleus.

The purified CIIIB1 protein has an apparent molecular mass of approximately 41 kDa, as estimated from SDS-PAGE analysis of chromatography fractions. Heat treatment did not affect CIIIB1 and resulted in a nearly homogenous preparation of the 41 kDa protein. This result indicates that the 41 kDa protein is probably responsible for the CIIIB1DNA binding activity. We confirmed this observation by radioactively labelling purified CIIIB1 in vitro through photoactivated crosslinking to a $^{32}$P-labelled CIIIB(WT) (−92 to −67; SEQ ID NO:39) probe containing 5 bromodeoxyuridine residues and analyzing the crosslinked complexes by SDS-PAGE. The crosslinked complex had an apparent molecular mass of approximately 50 kDa, approximately 8 kDa of which presumably reflects the presence of the crosslinked DNA sequence. The apparent molecular weight of purified CIIIB1 is not affected by the presence or absence of β-mercaptoethanol, indicating that CIIIB1 probably does not form homo- or hetero-dimers through disulfide bridges.

We compared the DNA binding characteristics of the purified CIIIB1 protein with those of CIIIB1 in liver extracts. Ogami et al. (1990, supra) had shown that oligonucleotides carrying mutations within apoCIII region −86 to −82 (CIIIBM1; SEQ ID NO:88) or apoCIII region −82 to −79 (CIIIBM2; SEQ ID NO:89) are not shifted by CIIIB1 in rat liver extracts. We found that purified CIIIB1 also does not shift these oligonucleotides. Furthermore, both crude and purified CIIIB1 still bind oligonucleotide CIIIBM5 (SEQ ID NO:90, which carries mutations within apoCIII region −78 to −73.

We further analyzed the purified CIIIB1 protein by examining its ability to protect element B of the apoCIII promoter from attack by DNaseI. We found, as expected, that purified CIIIB1 protects apoCIII promoter sequences from approximately −93 to −76 (1319 to 1336 of SEQ ID NO:14). Purified CIIIB1 also protected a sequence in the apoA-II promoter region, between approximately −65 and −48 (element AB; 837 to 864 of SEQ ID NO:1 1), and bound to sequences in element K (−760 to −743; 152 to 169 of SEQ ID NO:11) and element L (−803 to −773; 109 to 139 of SEQ ID NO: 11) of the apoA-II promoter (see Example 2 and Cardot et al. J. Biol. Chem. 266:24460–24470). Element B of the apoCIII promoter and element AB of the apoA-II promoter both contain the octameric motif 5'-CAGGTGAC-3' (SEQ ID NO:91). Elements K and L of the apoA-II promoter contain related motifs. Mutations in elements AB, K, and L of the apoA-II promoter that disrupt this octamer motif abolish detectable DNA binding by CIIIB1. Presumably, the octamer motif serves as a recognition site for CIIIB1.

Competition experiments revealed that the affinity of CIIIB1 for its cognate sequences in the apoCIII and apoA-II promoters follows the order apoA-II element AB>ApoCIII element B>apoA-II element L>apoA-II element K.

Further analysis of CIIIB1 binding to sequences in the apoA-II promoter revealed that CIIIB1 binds to sequences between −773 and −740 in element K (139 to 172 of SEQ ID NO:11) and between −803 and −783 in element L (109 to 116 of SEQ ID NO:11). Methylation interference studies revealed that G residues at −794 and −797 are involved in CIIIB1 binding to apoA-II element L.

It seemed likely that CIIIB1 is involved in transcriptional regulation of both the apoCIII and apoA-II genes. We therefore determined the transcriptional effects of promoter mutations that disrupt CIIIB1 binding. In particular, we introduced mutations that disrupt CIIIB1 binding to its cognate sites in the apoA-II promoter into a CAT reporter construct (see Example 2 and Cardot et al. J. Biol. Chem. 266:24460–24470, 1991). We found that deletion of element K or L reduced hepatic transcription to 20–25% of control levels and reduced intestinal transcription to 4–8% of control levels. A nucleotide substitution mutant, called LM2 that affected CIIIB1 binding to apoA-II element L reduced hepatic and intestinal transcription to approximately 63% of control levels. Similarly, substitution mutants ABM1 and KM1, that affected CIIIB1 binding to apoA-II elements AB and K respectively, reduced hepatic transcription to 60% and 20% of control levels, respectively, and reduced intestinal transcription to 36% and 10% of control levels, respectively. A double mutation in elements L and K reduced hepatic and intestinal transcription to 16% and 19% of control levels, respectively; a triple mutation in elements AB, K, and L reduced hepatic and intestinal transcription to 7% and 6% of control levels, respectively.

These results, taken together, indicate that protein factor CIIIB1 binds to regulatory elements within the apoCIII and apoA-II promoters and affects their transcriptional regulation. CIIIB1 functions as a transcriptional activator of the apoA-II gene. Furthermore, CIIIB1 molecules bound at apoA-II regulatory sites AB, K, and L act synergistically to regulate hepatic and intestinal transcription of the apoA-II gene.

Element CD

The CD region of the apoCIII promoter is recognized by several different protein factors. For example, C/EBP binds within the CD region, as do factors NF-BA2 and NF-BA3, which factors bind in several locations within the apoCIII promoter. The CD region also contains two binding sites for a novel activity, designated CIIIC1. CIIIC1 activity is heat-labile to treatment at 85° C. for 5 minutes. Mutations in element C that prevent the binding by CIIIC1, NF-BA2 and NF-BA3 reduced hepatic and intestinal transcription to 60–70% of control levels.

We have purified CIIIC1 by Q-Sepharose anion exchange chromatography followed by Bio-Rex 70 cation exchange chromatography and sequence specific DNA affinity chromatography using apoCIII sequences −160 to −142 as a ligand. CIIIC1 eluted from Q-Sepharose at approximately 0.3M KCl and from Bio-Rex 70 at approximately 0.4M to 0.5M KCl. CIIIC1 eluted from the sequence specific DNA affinity chromatography column at approximately 0.5M KCl. The purified CIIIC1 has an apparent molecular mass of approximately 100 kDa as estimated from SDS-PAGE analysis of chromatography fractions. The apparent molecular weight of the purified CIIIC1 protein is not affected by the presence or absence of β-mercaptoethanol, indicating that CIIIC1 probably does not form homo- or hetero-dimers through disulfide bridges.

We investigated the relationship of CIIIC1 to known protein transcription factors by performed competition gel shift experiments in which binding of partially purified CIIIC1 to a double stranded oligonucleotide probe corresponding to apoCIII promoter element D (−160 to −142; 1252 to 1270 of SEQ ID NO:14) was challenged with double-stranded oligonucleotides containing binding sites for known transcription factors C/EBP (Maire et al. Science 244:343–346, 1989; Dorn et al. Cell 50:863–3 872, 1987), NF1 (Maire et al. supra), NFY (Maire et al. supra, AP2/3 (Mitchell et al. Cell 50:847–861, 1987), OTF (Scheidereit et al. Cell 51:783–793), DBP (Maire et al. supra), NFkB, or by the BA3 oligonucleotide containing sequences (−78 to −48; SEQ ID NO:43) in element IV of the apoB promoter (see Table 7). The partially purified CIIIC1 used in these experiments had been chromatographed over Q-Sepharose (collected in the 0.3M KCl fraction) and Bio-Rex 70 (collected in the 0.4M KCl fraction). The results indicated that CIIIB1 is distinct from the protein factors whose binding sites we tested.

Factor CIIIC1 also binds to apoA-II promoter element D (−276 to −255; 636 to 657 of SEQ ID NO:11).

Utility

The present invention provides sequence elements and protein factors involved in apolipoprotein gene regulation, and reveals that apolipoprotein gene regulation involves the coordinated, often synergistic, action of many distinct protein factors bound to their cognate regulatory elements. The present invention further provides tools for modulating apolipoprotein gene expression. As has been discussed, apolipoproteins are involved in lipid metabolism and changes in apolipoprotein expression levels can significantly alter lipid metabolic pathways. For example, it is known that human subjects with low plasma apoA-I or low plasma HDL (of which apoA-II is a major component) have an increased risk of developing atherosclerosis (Castelli et al. Circulation 55:767–772, 1977; Heiss et al. Proc. Wkshp. Apolip. Quant. NIH Pub. 83–1266, pp. 7–24, U.S. Dept. of HHS, NIH, 1982; Glueck et al. Arch. Intern. Med. 135:1025–1028, 1975; Glueck et al. J. Lab. Clin. Med. 88:941–957, 1976; Patsch et al. Ateriosclerosis 1:156–161, 1981). It is also known that human subjects with lipoproteinemia, a condition in which apoB and LDL levels are reduced, are protected from atherosclerosis (reviewed in Zannis et al. Adv. Human Genet. 21:145–319, 1993). Furthermore, overexpression of the apoCIII gene is associated with hypertriglyceridemia in transgenic mice (Ho et al. Science 299:790–793, 1990). The present invention therefore provides tools that could prove useful for treatment of lipid metabolism disorders (e.g. atherosclerosis, hypertriglyceridemia, etc.).

Disruption of protein factor-sequence element interactions

We have demonstrated that apolipoprotein gene transcription can be modulated by disruption of protein factor-regulatory sequence interactions. Protein factor-regulatory sequence interactions can be disrupted by any of several different mechanisms.

We have shown, for example, that introduction of the AICM3 mutation into element C of the apoA-I promoter disrupts DNA binding by factor AIC1, and increases gene transcription 4.6 fold. Similarly, introduction of the LM2 or LM3 mutation into element C of the apoB promoter disrupts binding by factors BCB1, BCB2, and BCB3, and results in decreased gene expression. Other examples of point mutations that disrupt factor binding and affect gene transcription levels are also provided, as are procedures for identifying additional disruptive mutations (see above and Examples).

Protein factor-DNA sequence element interactions may be disrupted by methods other than introduction of mutations into sequence elements. For example, the presence of sufficient levels of competitor oligonucleotides to which a protein factor binds can prevent factor binding to a regulatory site in a transcription template. We have provided many examples of competitor oligonucleotides that can disrupt protein factor binding to its cognate regulatory site. We have further demonstrated that the presence of a competitor oligonucleotide capable of disrupting a protein factor-regulatory site interaction can have significant transcriptional consequences. In particular, we have demonstrated that the presence of competitor oligonucleotide BA1, which can compete the interaction between factor NF-BA1 and its cognate regulatory site on a transcription template, can reduce in vitro transcription of that template. It is well within the ordinary skill in the art to perform similar tests with other transcription factors and identify appropriate competitor oligonucleotides whose presence has significant transcriptional consequences. Transcriptional consequences can be determined in in vitro or in vivo transcription systems.

Other methods of disrupting protein factor-regulatory site interactions are also within the scope of the invention. Any disruptive agent known in the art may be used, although it is generally preferred that the agent specifically disrupt a particular protein factor-regulatory site interaction. It is further preferred that the agents be capable of entering a cell and passing into the nucleus, and that they not be toxic to a cell.

For example, agents that interfere with protein DNA-binding activity can disrupt transcription factor-regulatory site interactions. In particular, preferred agents include antibodies to apolipoprotein transcription factors, which antibodies are capable of interfering with factor DNA binding. Such antibodies can be generated by any method known in the art (see Harlow et al. Antibodies: a Laboratory Manual, Cold Spring Harbor Press, Cold Spring Harbor, N.Y., 1988; and Catty et al. Antibodies: a Practical Approach, Vols. I and II, IRL Press, Oxford, England, 1988 (Vol. I) and 1989 (Vol. II), each of which is incorporated herein by reference) and can be tested in DNA binding assays for their ability to interfere with protein factor DNA binding and in in vivo or in vitro transcription assays to determine their transcriptional significance.

DNA binding and in vivo or in vitro transcription assays can also be used to identify other chemical agents such as, for example, DNA intercalating agents, that are capable of disrupting protein factor-regulatory site interactions.

Protein-DNA interactions can also be disrupted by mutagenesis of the protein factor and selection of mutant variants with altered binding characteristics. Generally, protein factors are mutagenized by mutagenesis of DNA sequences that encode them. If such DNA sequences are not known, a purified factor can be isolated and subjected to standard amino-terminal sequencing techniques. DNA probes capable of encoding the identified amino-terminal protein sequence can then be generated by, for example, chemical synthesis, and used to probe gene libraries to identify DNA sequences capable of encoding the complete protein factor. Once the DNA sequence that encodes the protein factor is known, it can be mutagenized using any technique known in the art including, for example, transformation through known mutator bacterial strains, chemical mutagenesis, or site-directed mutagenesis. As described herein, point mutations, insertions, or deletions can be efficiently introduced into double-stranded DNA using PCR, chemical synthesis of overlapping mutant oligonucleotides, and/or site-directed mutagenesis procedures. Oligonucleotide site-directed mutagenesis can be used to simultaneously change more that one nucleotide.

Mutant protein factors produced by such mutagenized sequences can be assayed in DNA-binding and/or transcription assays. Particularly preferred mutant variants show a "dominant negative" effect in that they are able to interfere with DNA binding by wild type protein factors. Such dominant negative variants, if provided to a cell, could disrupt an interaction between an endogenous wild type protein and its cognate DNA sequence element.

Disruption of protein-protein interactions

We have demonstrated that apolipoprotein gene regulation involves the synergistic action of multiple protein transcription factors bound to their cognate regulatory sites within the same promoter. Interference with interactions between or among transcription factors bound to their cognate regulatory sites, with interactions between transcription factors bound to their regulatory sites and "bridging" transcription factors that are not bound to DNA, or with interactions between transcription factors and the transcription machinery (i.e. RNA polymerase and the general transcription factors) could also affect apolipoprotein gene expression levels.

Protein-protein interactions may be disrupted by any of several different mechanisms. Any disruptive agent known in the art may be used, although it is generally preferred that agents disrupt only a particular protein-protein interaction. It is further preferred that the agents be capable of entering a cell and passing into the nucleus, and that they not be toxic to a cell. Agents can be assayed for their ability to disrupt protein-protein interactions using techniques known in the art such as, for example, native gel electrophoresis, protein blotting, column chromatography, density gradient centrifugation (see Rickwood et al. *Centrifugation*, 2nd Ed. IRL Press, Oxford England, 1984, incorporated herein by reference), di-hybrid fusion screens (see Song et al. Nature 340:245–245, 1989, incorporated herein by reference), etc.

Antibodies to apolipoprotein transcription factors may be used to disrupt interactions between those factors and other apolipoprotein transcription factors or the transcription machinery. Such antibodies can be generated by any method known in the art (see Harlow et al. supra; Catty et al. supra) and can be tested in in vivo or in vitro transcription assays for their ability to affect apolipoprotein gene transcription.

Alternatively, peptides may be provided that disrupt a particular protein-protein interaction. Peptide fragments of apolipoprotein transcription factors, or of the components of the transcription machinery, may be used. Alternately, any peptide capable of disrupting an interaction between or among apolipoprotein transcription factors, or between an apolipoprotein transcription factor and the transcription machinery, can be used. Peptides may be generated by any method known in the art including, but not limited to, chemical synthesis or cleavage of protein factors. Libraries of peptides may be generated using, for example, phage display methodologies (see Parmley et al. Gene 73:305–318, 1988; Scott et al. Science 249:386–390, 1990; Smith, G. P. Science 228:1315–1317, 1985; Smith, G. P. Gene 128:1–2, 1993, each of which is incorporated herein by reference). Peptides can be tested in in vivo or in vitro transcription assays for their ability to affect apolipoprotein gene transcription.

Other molecules can also be used to disrupt protein-protein interactions involved in regulation of apolipoprotein gene transcription. Particularly preferred disruptive molecules are small molecules that interfere with protein-protein interactions. For example, known pharmaceutical agents may be tested for their effects on apolipoprotein gene transcription.

Protein-protein interactions involved in regulating apolipoprotein gene transcription can also be disrupted by protein factor mutagenesis. Generally, protein factors are mutagenized by mutagenesis of DNA sequences that encode them. If such DNA sequences are not known, a purified factor can be isolated and subjected to standard amino-terminal sequencing techniques. DNA probes capable of encoding the identified amino-terminal protein sequence can then be generated by, for example, chemical synthesis, and used to probe gene libraries to identify DNA sequences capable of encoding the complete protein factor. Once the DNA sequence that encodes the protein factor is known, it can be mutagenized using any technique known in the art including, for example, transformation through known mutator bacterial strains, chemical mutagenesis, or site-directed mutagenesis (see McPherson et al. *Directed Mutagenisis* IRL Press, Oxford, England, 1991, incorporated herein by reference). As described herein, point mutations, insertions, or deletions can be efficiently introduced into double-stranded DNA using PCR, chemical synthesis of overlapping mutant oligonucleotides, and/or site-directed mutagenesis procedures. Oligonucleotide site-directed mutagenesis can be used to simultaneously change more that one nucleotide.

Mutant protein factors produced by such mutagenized sequenced can be assayed in in vivo and/or in vitro transcription assays for their effects on apolipoprotein gene expression. Particularly preferred mutant variants show a "dominant negative" effect in that they are able to interfere with interactions between wild type protein factors. Such dominant negative variants, if provided to a cell, could disrupt an interaction between an endogenous wild type protein factor and other apolipoprotein transcription factors or the transcription machinery.

Other Embodiments

The present invention encompasses sequence elements and protein factors involved in transcriptional regulation of apolipoprotein genes, and methods of regulating apolipoprotein gene regulation using the information provided thereby. It will be appreciated that the above-described preferred embodiment is not meant to limit the scope of the invention. Other embodiments are encompassed within the claims.

For example, additional protein factors involved in transcriptional regulation of apolipoprotein genes can be identified using DNA binding assays known in the art including, but not limited to the gel shift and footprinting assays described in detail herein. The use of competitor oligonucleotides in gel shift and footprinting studies can provide valuable information about the relationship of a bound protein factor to known factors and can also provide information about the number of distinct protein factors responsible for a given footprint (see, for example, Examples 1–5).

The exact regulatory site to which an identified protein factor binds can be more precisely defined using known methods such as, for example, methylation protection, or DNA binding and competition studies using mutated versions of the regulatory sequence.

The transcriptional significance of identified protein factors and regulatory sequences can be assessed using in vitro and in vivo transcription systems. For example, transcription assays can be used to monitor the effects of disrupting a particular protein-DNA interaction. Some examples of useful in vivo and in vitro transcription assays are described herein. Other systems are known in the art and can equally well be used. In particular, many methods for the detection of RNA produced by transcription are known in the art, e.g. Northern analysis, primer extension analysis, S1 protection analysis, etc. (see Sambrook et al. supra, incorporated herein by reference). If transcription levels decrease when an interaction between a particular protein factor and its cognate regulatory site is disrupted, that protein factor is revealed to be a transcriptional activator; conversely, if transcription levels increase when an interaction between a particular protein factor and its cognate regulatory site is disrupted, that protein factor is revealed to be a transcriptional repressor.

DNA binding and transcription assays can also be used to identify protein-protein interactions between and among apolipoprotein transcription factors by revealing synergy in DNA binding and/or transcriptional regulatory properties. For example, enhancement of the DNA binding capabilities of one factor in the presence of another factor suggests that the two factors are likely to physically interact, either directly or through mutual interaction with one or more bridging transcription factors. Protein-protein interactions can be further studied using any technique known in the art including, for example, native gel electrophoresis, protein blotting, column chromatography, density gradient centrifugation (see Rickwood et al. supra), di-hybrid fusion screens (see Song et al. supra, etc. Such techniques can be further combined with protein deletion and mutagenesis studies to precisely map interaction domains.

The transcriptional significance of identified protein-protein interactions can be analyzed using, for example, in vitro and in vivo transcription systems, as discussed above for protein factor-regulatory site interactions. For example, transcription assays can be used to monitor the effects of disrupting a particular protein-protein interaction.

Figure 5:
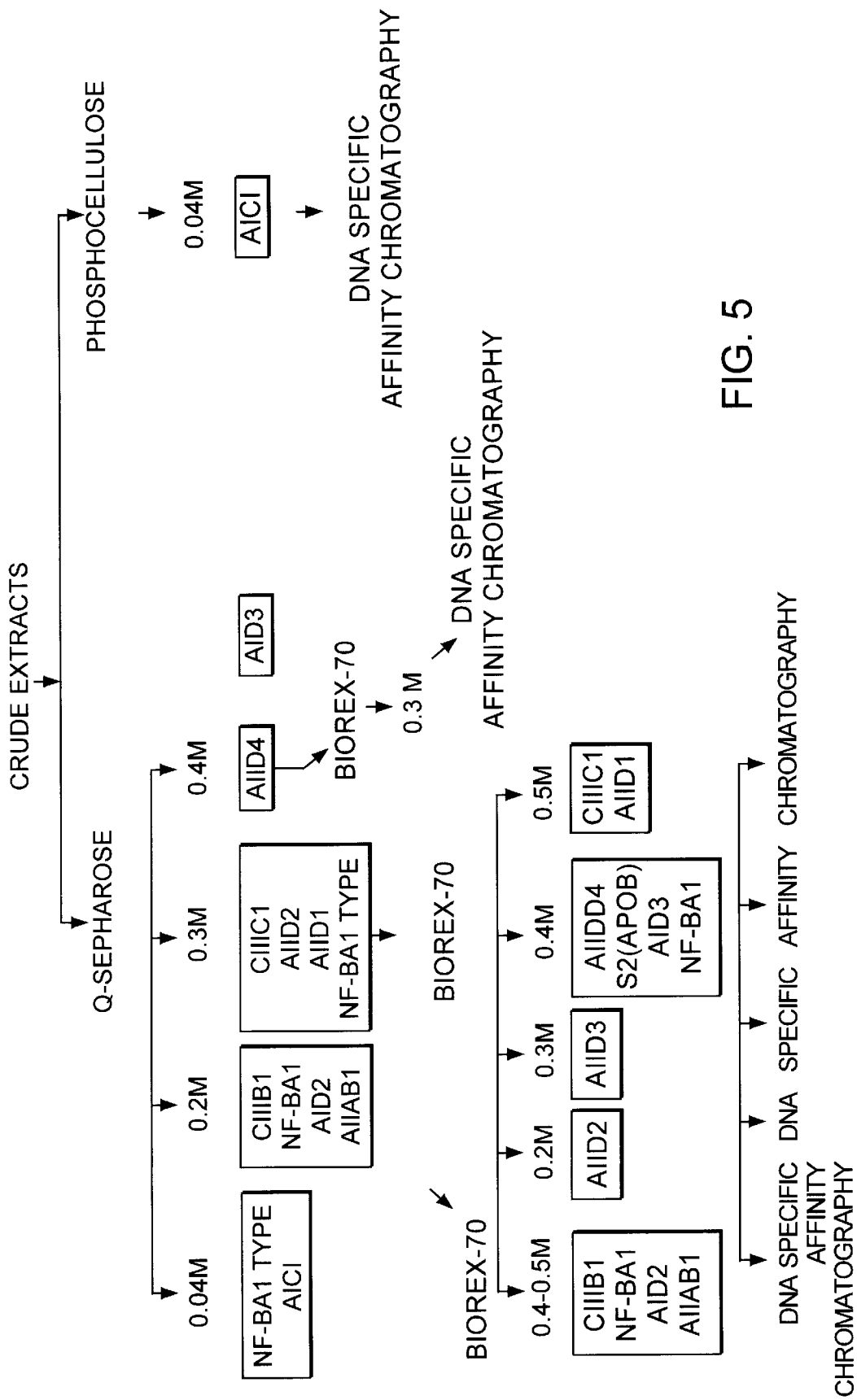
FIG. 5 is an outline of a purification scheme that can be used to isolate apolipoprotein transcription factors.
Figure 6A:
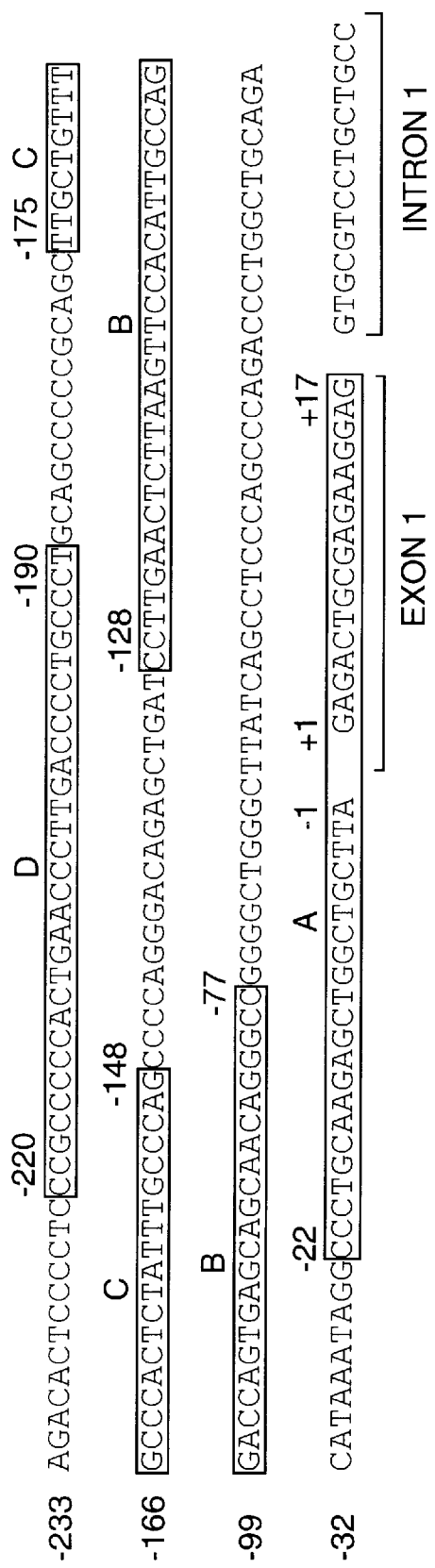

Identified protein factors of the invention can be characterized by purification. The direct isolation of transcription factors from cell extracts offers several advantages. First of all, the purified factor is functionally linked to the target gene that it regulates. A gene encoding the protein factor can be isolated by known techniques such as amino-terminal sequencing coupled with PCR and hybridization screening of cDNA libraries (see, for example, Sambrook et al. supra) and can be assigned a function based on the known relationship between the protein factor and the target gene. Secondly, the purified factor can be directly tested for function in in vitro transcription assays. The purification of different protein factors can be coordinated. For example, the overall purification scheme outlined in FIG. 5 can be used to purify many different protein factors involved in transcriptional regulation of apolipoprotein genes. Where sequence specific DNA affinity chromatography is used in protein purification procedures, the oligonucleotide used as a ligand need not have the exact boundaries as that of the regulatory element to which it corresponds, so long as it includes the entire binding site required for recognition by the protein factor of interest and does not include binding sites for other transcription factors. The absence of binding sites for other transcription factors on a particular oligonucleotide ligand can be assayed, for example, by gel-mobility shift studies as described herein.

EXAMPLES

Example 1

Identification and Characterization of Regulatory Elements and Protein Factors Involved in Transcriptional Regulation of the ApoA-I Gene Materials—Heparin agarose, DEAE-Sepharose, protease inhibitors, aprotinin, and phenylmethylsulfonyl fluoride were purchased from Sigma. Cyanogen bromide-activated Sepharose 4B and Mono Q columns were purchased from Pharmacia LKB Biotechnology Inc. Other materials were obtained from sources reported in Ogami et al. J. Biol. Chem 265:9808–9815, 1990.

ApoA-I Promoter-containing Plasmids and in Vitro Mutagenesis of the apoA-I Promoter—The apoA-I promoter region was derived from an apoA-I genomic clone described in Makrides et al. Eur. J. Biochem, 173:465–471. The PvuII-HindIII fragment (−1467 to +399) was subcloned into intermediate vectors. Derivatives were generated by Ba131 digestion. Two pEMBL8-CAT derivatives containing normal and mutated promoter sequences (−253 to −4 and −253 to +71) were utilized in the present study.

To mutagenize the apoA-I promoter, the region between nucleotides −264 and +5 was reconstructed with six sets of synthetic oligonucleotides, designated 1–6, with complementary single-stranded ends. Initially, the oligonucleotides 1 (containing an Asp-718 site on the 5' end), 5, and 6 (containing an SmaI site on the 3' end) were ligated into the Asp-718 and SmaI sites of the pUCSH-CAT plasmid (Ogami et al. J. Biol. Chem. 265:9808–9815, 1990) to produce the CAT derivative designated pUC-SN-AI-CAT. This derivative contains the apoA-I promoter sequences −264 to −219 (originating from oligonucleotide 1) and −80 to +5 (originating from oligonucleotides 5 and 6), joined by the polylinker region 5'CCGCGGACTCGAGTGCCGGC-3'; (SEQ ID NO:92), which contains SacII, XhoI, and NaeI sites. Digestion of this plasmid with SacII and NaeI allows the introduction of normal or mutated blocks of oligonucleotides 2 (−218 to −178), 3 (−177 to −129), and 4 (−128 to −81), containing footprint areas D, C, and B, respectively. In this manner, we introduced three mutations in the regions −176 to −171, −164 to −159, and −152 to −146, designated M1, M3, and M5, respectively. Two other mutations, designated M2 and M4, were introduced in the regions −171 to −166 and −158 to −153 with site-directed in vitro mutagenesis (Roghani et al. Biochemistry 27:7428–7435, 1988). For this analysis, *Escherichia coli* 71-18 transformed with the pEMBL-CAT AI-253/-4 plasmid were superinfected with helper fl variant ID1 phage at a multiplicity of infection of 20:1. Single-stranded template was prepared and mutagenized with standard techniques as described previously (Roghani et al. supra). Mutations were designed to change purines to the opposite pyrimidine residues and vice versa and were verified by DNA sequencing.

CAT Assays—Human hepatoma (HepG2) (Knowles et al. Science 209:497–499, 1980) cells were grown in 60-mm-diameter dishes in Dulbecco's modified Eagle's medium containing 10% fetal calf serum. The cells were contransfected by the calcium-phosphate DNA coprecipitation method (Graham et al. Virology, 52:456–467, 1973) with 12 $\mu$g of $\beta$-Gal plasmid (Edlund et al. Science 230:912–916, 1985) and harvested 42 h later. The CAT activity of the cell lysate was determined in triplicate and was normalized for the $\beta$-galactosidase activity (Gorman et al. Mol. Cell. Biol. 2:1044–1051, 1982).

Preparation and Fractionation of Nuclear Extracts— Nuclear extracts were prepared from 80 male Sprague-Dawley rat livers essentially as described (Ogami et al. J. Biol. Chem 265:9808–9815, 1990; Gorski et al. Cell. 47:767–776, 1986). The crude extracts in buffer A (20 mM Hepes, pH 7.9, 0.2 mM EDTA, 0.5 mM diothiothreitol, 10% glycerol, 0.1 mM (phenylmethylsulfonyl fluoride, 2 $\mu$g/ml aprotinin, 0.1% Nonidet P-40) were adjusted to 300 mM KCl and loaded on a DEAE-Sepharose column. The flow-through was adjusted to 200 mM KCl in buffer A and loaded onto a heparin-agarose column (100-ml, bead volume). The column was eluted with a linear gradient of 200–700 mM KCl in buffer A. Seventy-five 9-ml fractions were collected. Fractions 30–42, eluting at an average KCl concentration of 350 mM and containing the activity AID2, and fractions 48–57, eluting at an average KCl concentration of 500 mM and containing the activity AID1 (LF-A1), were pooled. The AID2 active fractions were further fractionated with a Mono Q column. At 150 mM KCl in buffer A, factor AID2 is recovered in the flow-through, while a contaminating LF-B1 activity is retained on the column (Frain et al. Cell, 59:145–157, 1989; Hardon et al. EMBO J. 7:1711–1719, 1988). This fraction was used for DNA binding assays and DNase I footprinting. The AID1 (LF-A1) active fractions were purified further by DNA sequence specific affinity chromatography (Hardon et al. supra) and were used for DNase I footprinting analysis. For DNA binding assays, $^{32}$P-labeled doublestranded synthetic oligonucleotides corresponding to either apoA-I (−215 to −191) or $\alpha$1-antitrypsin (−131 to −103) gene sequences were used.

Expression of the Rat C/EBP cDNA in Bacterial Cells; Purification of the C/EBP Protein—The rat C/EBP cDNA, kindly provided by Dr. McKnight, Carnegie Institution of Washington (Landschulz et al. Genes Dev. 2:786–800, 1988), was expressed in *E. coli* using the PT7-7 expression vector (Studier et al. Met. Enzymol. 185:60–89, 1990). C/EBP was purified from cell lysates by DEAE-cellulose fractionation and heat treatment at 70° C. for 5 min as described (Landschulz et al. Science 1681–1688, 1989). The resulting fraction contained a major protein of 40-KDa molecular mass, corresponding to rat C/EBP (Landschulz et al. Science 1681–1688, 1989), and was used for DNA binding and protection assays.

DNase I Footprint and Competition Analysis—ApoA-I regions −253 to +71 and −253 to −4 were excised from the pEMBL8-CAT plasmid derivative with EcoRI and/or XmaI and HindIII digestion at the 5' and 3' ends, respectively. The former fragment was labeled at the 3' HindIII site with [$\gamma$-$^{32}$P]ATP and T4 polynucleotide kinase. The second fragment was labeled at the XmaI site with either [$\gamma$-$^{32}$P]ATP and polynucleotide kinase or [$\alpha$-$^{32}$P]dCTP and Klenow fragment of DNA polymerase I. The −264 to −81 fragment was produced by DNA amplification using the polymerase chain reaction (Mullis et al. Met. Enzymol. 155:335–350, 1987). The pUC derivative described above that carries the −264 to +5 apoA-I region was used as a template for this amplification. The 5' primer used for amplification corresponded to the −264 to −227 apoA-I sequence and contained an EcoRV and Asp-718 site. The 3' primer corresponding to nucleotides −81 to −134 was labeled at the 5' end with [$\gamma$-$^{32}$P]ATP and polynucleotide kinase prior to the amplification. Footprint analysis was performed with a modification of published procedures (Staudt et al. Nature 323:640–643, 1986; Treisman Cell. 46:567–574, 1986). Briefly, 25–55 $\mu$g of nuclear protein extracts prepared as described (Landschulz et al. 1988 supra; Gorski et al. Cell 47:767–776, 1986) were preincubated in a 20 $\mu$l reaction containing 25 mM Hepes,$^2$ pH 7.6, 40 mM KCl, 5 mM MgCl$_2$, 0.1 mM EDTA, 10% glycerol, 1 mM dithiothreitol, and 1 $\mu$g of double-stranded poly(dI-dC). When purified fractions were used, either 10 $\mu$l (1 $\mu$g) of heparin-agarose, Mono Q-fractionated AID2 factor, or 10 $\mu$l (2–10 ng) of affinity-purified LF-A1 factor was employed (Hardon et al. supra. After 15 min on ice, 15,000 cpm of end-labeled fragment was added and the incubation was continued for 90 min at 4° C. Two μl of DNase I, freshly diluted to a final concentration of 6.25–150 μg/ml in 25 mM CaCl$_2$, was added, and the digestion was allowed to proceed for 5 min at 4° C. The reaction was terminated by the addition of 4 μl of 125 mM Tris-HCl, pH 8.0, 125 mM EDTA, 3% sodium dodecyl sulfate, Forty μg of proteinase K and 5 μg of tRNA were added, and the reaction mixture was incubated for 30 min at 65° C. The DNA was extracted once with 100 μl of phenol/chloroform, precipitated with 2.5 volumes of EtOH, resuspended in 98% formamide-dye, and electrophoresed on a 6% polyacrylamide, 7M urea sequencing gel. Competition footprinting was performed in the presence of 50–1000 ng of competitor oligonucleotide, which are shown in Table 1.

TABLE 1

Sequences of Competitor Oligonucleotides

| NAME | SEQUENCE | SEQ ID NO: |
|---|---|---|
| apoA-I | $^{-215}$CCCACTGAACCCTTGACCCCTGCC$^{-191}$ | 17 |
| α-1-Antitrypsin inhibitor, large (α1AT1) | $^{-130}$ATCCAGCCAGTGGACTTAGCCCCTGTTTGCTCCTCC$^{-93}$ | 18 |
| n-1-Antitrypsin, small (α1AT2) | $^{-131}$GATCCCAGCCAGTGGACTTAGCCCCTAG-$^{-103}$ | 19 |
| apoC-IIID | $^{-165}$GTCCTAGGGATTTCCCAACTCTCCCGCCC$^{-137}$ | 20 |
| apoB | $^{-78}$GCCCTTTGGACCTTTTGCAATCCTGGCGCTC$^{-48}$ | 21 |
| Octamer motif binding protein (OCT.BP) | $^{-567}$ATCCTCAACTTATTTTAGAAATGCAAATTACCCAGGTGGT$^{-528}$ | 22 |
| SP1 | GATACGCGTATCGGGGCGGAGAAACACTGC | 23 |
| NFY | $^{-92}$GGAACCAATGAAATGCGAGG$^{-73}$ | 24 |
| NF1 | $^{-140}$AGTCAAACAATTTTTTGGCAAGAATATTATGAAT$^{107}$ | 25 |
| Albumin C/EBP | $^{-115}$TGGTATGATTTTGTAATGGGGTAGGA$^{-90}$ | 26 |
| TK C/EBP | $^{-96}$GCGTCTTGTCATTGGCGAATTCG$^{-74}$ | 27 |
| Nonspecific Oligonucleotide sequence (NS) | GGTGAATTCGAGCTCGGTACCCGGGGATCCTCTAGAGTCGAC | 28 |
| AI(WT) | $^{-177}$GCTTGCTGTTTGCCCACTCTATTTGCCCAGCCCCAG$^{-142}$ | 29 |
| AICM1 | $^{-177}$GAGGTAGGTTTGCCCACTCTATTTGCCCAGCCCCAG$^{-142}$ | 30 |
| AICM2 | $^{-177}$GCTTGCGTGGGTCCCACTCTATTTGCCCAGCCCCAG$^{-142}$ | 31 |
| AICM3 | $^{-177}$GCTTGCTGTTTGCAACAGATATTTGCCCAGCCCCAG$^{-142}$ | 32 |
| AICM4 | $^{-177}$GCTTGCTGTTTGCCCACTCGCGGGTCCCAGCCCCAG$^{-142}$ | 33 |
| AICM5 | $^{-177}$GCTTGCTGTTTGCCCACTCTATTTGAAACTAACCAG$^{-142}$ | 34 |

Synthetic Oligonucleotides—Oligonucleotides corresponding to normal and mutant apoA-I promoter sequences were synthesized by the solid-phase phosphite triester method with an automated oligonucleotide synthesizer (Applied Biosystems, model 380-B) and purified by electrophoresis on 20% polyacrylamide, 7M urea gels. The oligonucleotides were extracted from the gel by overnight incubation at 35° C. in 500 mM NH$_4$OAc, 10 mM MgOAc, 1 mM EDTA, 0.1% sodium dodecyl sulfate and were labeled with $^{32}$p as described (Ogamo et al. J. Biol. Chem. 265:9808–9815, 1990).

DNA Binding Gel Electrophoretic Assays—For this analysis 6–10 μg of nuclear protein extracts or 0.5 μl of purified C/EBP were preincubated for 15 min at 4° C. in a 20-μl reaction containing 25 mM Hepes, pH 7.6,8% Ficoll, 40 mM KCl, 1 mM dithiothreitol, 3 μg of double-stranded poly (dI-dC), and 5 mM MgCl$_2$ in the presence or absence of 100–400 ng of competitor oligonucleotide sequences (see Fried et al. Nuc. Acid. Res. 9:6505–6525, 1981). Next, 30,000 cpm of labeled double-stranded apo-A-I oligonucleotide was added, and the incubation continued for 30 min at 4° C. Free DNA and DNA-protein complexes were resolved on a 4% polyacrylamide gel in 1×TAE buffer (6.7 mM Tris, 3.3 mM sodium acetate, 1 mM EDTA, pH 7.9). Following electrophoresis, the gel was dried onto DE81 (Whatman) paper and exposed to x-ray film.

Purification of AIC1—Phosphocellulose and Q-Sepharose chromatography was performed essentially as described in Ogami et al. J. Biol. Chem. 266:9640–9646, 1991.

Q-Sepharose Fractionation of Factors that bind to apoA-I Element D- Q-Sepharose chromatography was performed essentially as described in Ogami et al. J. Biol. Chem. 266:9640–9646, 1991.

Example 2

Identification and Characterization of Regulatory Elements and Protein Factors Involved in Transcriptional Regulation of the ApoA-II Gene Materials—All materials were purchased from sources described in Ogami et al. Biol. Chem 265:9808–9815, 1990.

Synthetic Oligonucleotides and DNA Fragments Generated by the Polymerase Chain Reaction (PCR)—Oligonucleotides were synthesized by the solid phase phosphite triester method using an automated oligonucleotide synthesizer (Applied Biosystems, model 380-B). The oligonucleotides were purified by electrophoresis on 20% polyacrylamide, 7M urea gels and labeled with $^{32}$p as described (Ogami et al. J. Biol. Chem. 265:9808–9815, 1990). A number of DNA fragments were generated by DNA amplification using the polymerase chain reaction (Mullis et al. Met. Enzymol. 155:335–350, 1987). The fragments generated and the primers used are shown in Table 2. The sequence of the fragments and their orientation in the final constructs were determined by DNA sequencing. PCR reactions were performed using the Perkin-Elmer automated thermocycler according to the manufacturer's specifications.

TABLE 2

Fragments generated by DNA amplification using the PCR

| | 5'-Amplification primers | 3'-Amplification primers |
|---|---|---|
| Synthetic fragments generated by PCR | | |
| 1. ApoA-II (−80/+29) containing an 18-nucleotide polylinker | 1a. ApoA-II (−80 to −57) | 1b. ApoA-II(−4 to +29) with XhoI and BamHI restriction sites |
| 2. ApoA-II (−230/+29) | 2a. ApoA-II (−230 to −202) | 1b. ApoA-II (+4 to +29) with XhoI and BamHI restriction sites (CCATGGATCTGCTCGAG) (SEQ ID NO: 112) at the 5' end |
| 3. ApoA-II (−440/+29) | 3a. ApoA-II (−440 to −414) | 1b. ApoA-II (+4 to +29) with XhoI and BamHI restriction sites (CCATGGATCTGCTCGAG) (SEQ ID NO: 112) at the 5' end |
| 4. ApoA-II (−911/−614) containing 34 nucleotides 5' and 10 nucleotides 3' polylinker region | 4a. Nucleotides 34 to 9 bp upstream of HindIII site of the pUC19 polylinker | 4b. ApoA-II (−641 to −616) with BamHI restriction site (CCATGGATCC) (SEQ ID NO:113) at the 5' end |
| 5. ApoA-II (−781/−523) | 5a. ApoA-II (−781 to −753) | 5b. ApoA-II (−550 to −523) |
| 6. ApoA-II (−671/−379) | 6a. ApoA-II (−671 to −644) | 6b. ApoA-II (−408 to −379) |
| 7. ApoA-II (−440/−160) | 3a. ApoA-II (−440 to −414) | 7b. ApoA-II (−185 to −160) |
| 8. ApoA-II (−911/+29) (−573 to −554) | 8a. ApoA-II (−554 to −523) | 1b. ApoA-II (+4 to +29) with XhoI and BamHI restriction sites) (CCATGGATCTGCTCGAG) (SEQ ID NO: 112) at the 5'-end |
| | 4a. Nucleotides 34 to 9 bp upstream of HindIII site of the pUC19 polylinker | 8b. −523 to −602 Δ(−573 to −554) |
| Deletion mutants of domains L and K | | |
| 1. ApoA-II −911 to +29, Δ (−810 to −768) (deletion L domain) | 9a. Nucleotides 34 to 9 upstream of HindIII site of pUC19 polylinker | 9b. ApoA-II +4 to +29 with XhoI and BamHI restriction sites (CCATGGATCTGCTCCGAG) (SEQ ID NO: 112) at 5'-end |
| 2. ApoA-II −911 to +29, Δ (−761 to −743) (deletion K domain) | 10a. ApoA-II −861 to −810 | 10b. ApoA-II −768 to −712 |
| | 1a | 1b |
| | 11a. ApoA-II −792 to −714, Δ (−761 to −743) | 11b. Apo-AII −743 to −714 |
| Substitution mutants of domains AB, L, and K | | |
| 1. ApoA-II −911 to +29 with | 9a | 9b |
| substitution at residues −48, −49, −52, and −56 to −61 of domain AB. Mutations affect binding of CIIIB1. | 12a. Mutated oligo antisense strand −71 to −32 | 12b. Mutated oligo sense strand −71 to −32 |
| 2. ApoA-II −911 to +29 with | 9a | 9b |
| substitution at residues −783 and −784 of domain L. Mutations affect binding site of CCAAT box activities. | 13a. Mutated oligo antisense strand −810 to −773 | 13b. Mutated oligo sense strand −810 to −773 |
| 3. ApoA-II −911 to +29 with | 9a | 9b |
| substitution at residues −792 and −794 of domain L. Mutation affects binding site of CIIIB1. | 14a. Mutated oligo antisense strand −810 to −773 | 14b. Mutated oligo sense strand −810 to −773 |
| 4. ApoA-II −911 to +29 with | 9a | 9b |
| substitution at residues −746, −747, and −755 to −758 of | 15a. Mutated oligo antisense | 15b. Mutated oligo sense strand −774 to −739 |

TABLE 2-continued

Fragments generated by DNA amplification using the PCR

| | | | |
|---|---|---|---|
| domain K. Mutations affect binding site of CIIIB1. | strand −774 to −739 | | |
| 5. ApoA-II −911 to +29 double | 9a | | 9b |
| mutant in domains K and L. Mutations affect binding site of CIIIB1 in domains K and L. | 14a. Mutated oligo antisense strand −810 to −773 | 14b. Mutated oligo sense strand −810 to −773 | 15b. Mutated oligo sense strand −774 to −379 |
| 6. ApoA-II −911 to +29 triple | 9a | | |
| mutant in domains L, K, and AB. Mutations affect binding site of CIIIB1 in all 3 domains. | 14a. Mutated oligo antisense strand −810 to −773 | 14b. Mutated oligo sense strand −810 to −733 | |
| | | 9b | |
| | 15a. Mutated oligo antisense strand −774 to −739 | 15b. Mutated oligo sense strand −774 to −739 | 4b. Mutated oligo sense strand −71 to −21 |
| | | 12a. Mutated oligo antisense strand −71 to −32 | |

| Deletion mutants of domains A–G, I, J, and M | primers for amplification of the region upstream of the deletion | primers for amplification of the region downstream of the deletion |
|---|---|---|
| 1. apoA-II (−911/+29) Δ(−32 to −42) (deletion A domain) | 16a (nucleotide +34 to +9 upstream of HindIII site of the pUC19 polylinker (sense)) | 16b (apoA-II (+4 to +29) with XhoI and BamHI restriction sites (CCATGGATCTGCTCGAG) (SEQ ID NO: 112) (antisense)) |
| 2. apoA-II (−911/+29) Δ(−42 to −65) (deletion B domain) | 17a (apoA-II (−65 to −42) (antisense)) 16a 18a (apoA-II (−88 to −66) (antisense)) | 17b (apoA-II (−32 to −8) (sense)) 16b 18b (apoA-II (−41 to −13) (sense)) |
| 3. apoA-II (−911/+29) Δ(−32 to −65) | 16a 18a | 16b 17b |
| 4. apoA-II (−911/+29) Δ(−110 to −126) (deletion C domain) | 16a 19a (apoA-II (−154 to −127) (antisense)) | 16b 19b (apoA-II (−154 to −83 Δ(−126 to −110) (sense)) |
| 5. apoA-II (−911/+29) Δ(−255 to −276) (deletion D domain) | 16a 20a (apoA-II (−306 to −277) (antisense)) | 16b 20b (apoA-II (−254 to −226) (sense)) |
| 6. apoA-II (−911/+29) Δ(−364 to −377) (deletion E domain) | 16a 21a (apoA-II (−378 to 407) (antisense)) | 16b 21b (apoA-II (−363 to −334) (sense)) |
| 7. apoA-II (−911/+29) Δ(−4-4 to −384) (deletion F domain) | 16a 22a (apoA-II (−405 to −428) (antisense)) | 16b 22b (apoA-II (−383 to −356) (sense)) |
| 8. A-II (−911/+29) Δ(−455 to −469) (deletion G domain) | 16c 23a (apoA-II (−469 to 493) (antisense)) | 16b 23b (apoA-II −455 to −428) (sense)) |
| 9. apoA-II (−911/+29) Δ(−706 to −675) (deletion I domain) | 16a 24a (aopA-II (−761 to −707) (antisense)) | 16b 24b (apoA-II (−675 to −614) (sense)) |
| 10. apoA-II (−911/+29) Δ(−734 to −716) (deletion J domain) | 16a 25a (apoA-II (−679 to −764)Δ(−734 to −716) (antisense)) | 16b 25b (apoA-II (−711 to −676) (sense)) |
| 11. apoA-II (−911/+29) Δ(−853 to −829) (deletion M domain) | 16a 26a (aopA-II (−802 to −881)Δ(−853 to −829) (antisense)) | 16b 26b (apoA-II (−828 to −802) (sense)) |

Plasmid Constructions—A 3-kb HindIII/HindIII fragment containing the entire apoA-II gene was obtained from a human genomic library and subcloned in plasmid pUC19 to generate pUC-AII. The pUC-AII plasmid was digested with ApaI and BamHI to excise the apo-A-II fragment containing the coding sequences from −80 to +2 kb (Tsao et al. J. Biol. Chem. 260:15222–15231, 1985; Sharpe et al. Nuc. Acid. Res. 12:3917–3932, 1984). The −80 to +29 apoA-II region was obtained from the DNA fragment 1 generated by PCR (see Table I) following digestion with ApaI (−80) and BamHI. The fragment was ligated at the ApaI and BamHI sites of pUCA-II to generate the −911/+29 pUC-AII plasmid. The −911 to +29 apoA-II fragment was excised with HindIII and XhoI from the −911/+29 pUC-AII and cloned into the corresponding sites of pUSCH-CAT to generate the plasmid −911/+29 apoA-II CAT. This plasmid was grown in the dam⁻ *Escherichia coli* strain (GM33) and digested with HindIII (−911) and BclI (−614). The −860 to −614 region was then restored with a set of five double-stranded synthetic oligonucleotides with complementary ends to generate the −860/+29 apoA-II CAT plasmid. The −911/+29 pUC-AII plasmid was digested with BclI (−614) and EcoRV (−900), blunt-ended with T4 polymerase, and relegated to generate the −614 to +29 pUC-AII plasmid. The resulting plasmid was digested with HindIII and XhoI, and the −614/+29 promoter region was cloned into the corresponding sites of the pUCSH-CAT vector to generate the −614/+29 apoA-II CAT plasmid. To generate the CAT construct containing the −84 to +29, −230 to +29, and −440 to +29 apoA-II promoter region, the −911/+29 apoA-II CAT plasmid was digested with EcoRV (−900) and XhoI, and the excised region was replaced with the corresponding synthetic DNA fragments 1, 2, or 3 (Table 2) that were previously digested with XhoI. The last four CAT derivatives also contain the −911 to −900 apoA-II promoter region.

To generate the −911/+29 CAT construct containing the −614 to −230 deletion, synthetic DNA fragments 2 and 4 (Table 2) were digested with XhoI and HindIII, respectively, and ligated into the corresponding sites of the pUCSH-CAT. The primers 2a and 4b (Table 2) used for amplification of fragments 2 and 4 were phosphorylated with T4 polynucleotide kinase prior to amplification. The −911/+29 CAT construct containing the deletion of domain H (−573 to −554) was generated with PCR amplification of the pUC-AH plasmid. The region 3' to nucleotide −554 was amplified using the 5' and 3' amplification primers 8a and 1b, respectively (Table 2). The region upstream of nucleotide −523 was amplified using the 5' and 3' amplification primers 4a and 8b, respectively (Table 2). The 8b primer extends from nucleotides −523 to −602 and contains the desired −573 to −554 deletion. An aliquot containing 4% of the two amplified regions was used for further amplification using the 5' and 3' amplification primers 4 a and 1b (Table 2). The amplified DNA was excised with HindIII and XhoI digestion, purified by elution from agarose gel, and closed into the HindIII and XhoI sites of the pUCSH-CAT vector.

CAT construct −911 to +29 containing a deletion of domain L (nucleotides −810 to −768) was generated by polymerase chain reaction amplification of the pUC-AII plasmid. For deletion of domain L, the region upstream of nucleotide −810 was amplified using the 5'- and 3'-amplification primers 9a and 10a respectively (Table 2). The region downstream of nucleotide −768 was amplified using the −5' and 3'-amplification primers 10b and 9b, respectively. The two amplified fragments were digested with HindIII and XhoI, respectively; purified by electroelution from the agarose gel; and cloned into the corresponding sites of the pUCSH-CAT vector. For deletion of domain K (nucleotides −761 to −743), the region upstream of nucleotide −743 was amplified using the 5'- and 3'amplification primers 9a and 11a, respectively. Primer 11a extends from nucleotides −792 to −714 and contains deletion −761 to −743. The region downstream of nucleotide −743 was amplified using the 5'- and 3'- amplification primers 1b and 9b, respectively. An aliquot containing 4% of the two amplified primers 9a and 9b, respectively. The amplified DNA was digested with HindIII and XhoI, purified by electroelution from the agarose gel, and closed into the HindIII and XhoI sites of pUCSH-CAT.

Nucleotide substitution mutants were generated with four sets of amplification primers. For example, domain L was mutated with nucleotide substitutions at residues −783 and −784 as follows. The region upstream of nucleotide −773 was amplified using, as 5'- and 3'-primers, oligonucleotides 9a and 13a, respectively. The region downstream of nucleotide −810 was similarly amplified using, as 5'- and 3'-primers, oligonucleotides 13b and 9b, respectively (Table 2). Primers 13b and 13a correspond to sense and antisense sequences −810 to −773, respectively, and contain nucleotide substitutions at residues −783 and −784. Aliquots containing 4% of the two amplified regions were mixed and used for further amplification using, as 5'- and 3'-amplification primers, oligonucleotides 9a and 9b, respectively. In a similar manner, nucleotide substitutions were also introduced in domain B (residues −48m−49, −52, and −56 to −61) using mutated oligonucleotides 12a and (residues −792 a (residues −792 and −794) using mutated oligonucleotides 14a and 14b, and in domain K (residues −746, −747, and −755 to −758) using mutated oligonucleotides 15a and 15b. The double mutations in domains K (residues −746, −747 and −755 to −758) and L (residues −792 and −794) were generated by amplifying the region upstream of nucleotide −773 with primers 9a and 14a, the region between nucleotides −810 and −740 with oligonucleotides 14b and 15a, and the region downstream of nucleotide −773 with oligonucleotides 15b and 9b respectively. The triple mutations in domains K, L, and AB were generated by amplifying and mutating the sequences in domains K, L, and AB in four separate reactions. The regions upstream of nucleotide −773 and between nucleotides −810 and −740 were amplified as described above for the double mutations in domains K and L. The region between nucleotides −773 and −32 was amplified with oligonucleotides 7b and 4a, respectively; and the region downstream of nucleotide −71 was amplified with oligonucleotides 4b and 1b, respectively. Aliquots containing 4% of the four amplified regions were mixed and used for further amplification using, as 5'- and 3'-primers, oligonucleotides 1a and 1b, respectively. The amplified DNA was digested with HindIII and XhoI and closed into pUCSH-CAT as described above.

The −911/+29 CAT construct containing the deletion of elements A–M was generated with PCR amplification of the pUC-AII plasmid. For the deletion of regions A, B, AB, D, E, F, G, and I, the sequences upstream and downstream of the intended deletion were amplified separately. For instance, for the deletion of element A, the region upstream of nucleotide −42 was amplified using oligonucleotides 16 and 17a as 5' and 3' primers, and the region downstream of nucleotide −32 was amplified using oligonucleotides 17b and 16b as 5' and 3' primers, respectively (Table 2). The two amplified fragments for each deletion were digested with HindIII and XhoI, respectively, purified by electroelution from the agarose gel, and cloned into the corresponding sites of the pUCSH-CAT vector. Deletions B, AB,D,E,G, and F were generated in a similar manner using the primers listed in Table 2. For deletion of domain C(−126 to −110), the region upstream of nucleotide −126 was amplified using oligonucleotides 16a and 19a as 5' and 3' primers, respectively. The region downstream of nucleotide −154 was amplified using 5' and 3' amplification primers 16b and 19b. The 19b primer extends from nucleotide −154 to −83 and contains the −126 to −110 deletion. An aliquot containing 4% of the two amplified regions was used for further amplification using the 5' and 3' amplification primers 16a and 16b. The amplified DNA was digested with HindIII and XhoI, purified by electroelution from the agarose gel, and cloned into the HindIII and XhoI sites of the pUCSH-CAT. The deletions in domains M and J were constructed in a similar manner using the amplification primers shown in Table 2. The oligonucleotides carrying the deletion of domains J and M were 25a and 26a, respectively. apoA-II promoter plasmids were cotransfected with a β-galactosidase-containing plasmid in HepG2 cells by the calcium phosphate-DNA coprecipitation method (Graham et al. Virology 52: 456–467, 1973). CAT and β-galactosidase assays were performed as described previously (Edlund et al. serence 230:912–916, 1985; Gorman et al. Mol. Cell. Biol. 2:1044–1051, 1982).

Cell Transfection and Cat assays—Human hepatoma (HepG2) and colon carcinoma (CaCo2) and cervical carcinoma HeLa cells were maintained as stocks in Dulbecco's modified Eagle's medium supplemented with 10% and 20% fetal calf serum, respectively. 50 to 60% confluent 60-mm dishes were transfected using the calcium-phosphate DNA co-precipitation method (Graham et al. Virology 52: 456–467, 1976). The transfection mixture contained 10 µg of apoA-II CAT promoter plasmid DNA and 7 µg of βGal plasmid (Edlund et al. Science 230: 912–916, 1985). Cells were harvested 24 h later and lysed by freeze-thawing. CAT assays were performed in triplicate in 150 µl total volume of 0.47 MTris-HCI buffer, pH 7.8, containing 5 µl of [$^{14}$C] chloramphenicol and 0.53 mMacetyl-CoA as described (Gorman et al. Mol. Cell. Biol. 2: 1044–1051, 1982). The reaction times and extract concentrations were selected to ensure linear conversion of the chloramphenicol to the acetylated forms. The nonacetylated and acetylated chloramphenicol forms were separated on AB2 silica gel plates using chloroform/methanol, 95:5, for development. The radioactive spots, detected by autoradiography, were scraped from the thin layer plates and counted. The β-galactosidase activity of the cell lysates were determined as described in Edlund et al. supra, and the values were used to normalize variabilities in the efficiency of transfection.

Preparation of Nuclear Extracts and DNase I Footprinting Assays—Rat liver nuclear extracts were prepared as described in Gorski et al. Cell 47: 767–776, 1986. The synthetic DNA fragments 2, 4, 5, 6 and 7 (Table 2) were used to footprinting analysis. Either the 5' or the 3' primer was labeled with [γ-$^{32}$P]ATP and T4 polynucleotide kinase prior to the PCR amplification. Footprint analysis was performed in a 20 all reaction containing 25 mM Hepes, pH 7.6, 40 mMKCl, 5 mM MgCl$_2$, 0.1 mMEDTA, 10% glycerol, 1 mMdithiothreitol, and 1 µg of double-stranded poly(dI-dC), 18 to 72 µg of nuclear extracts, and 1.5×10$^4$ cpm of end-labeled fragment. Following an incubation of 90 min at 4° C., 2 µl of DNase I, freshly diluted to a final concentration of 20 to 140 µg/ml in 25 mMCaCl$_2$, was added, and the digestion was allowed to proceed for 5 min at 4° C. The reaction was stopped by the addition of 4 µl 125 mM Tris-HCl, pH 8.0, 125 mM EDTA, and 3% sodium dodecyl sulfate. Forty µg of proteinase K and 5 µg of tRNA were added, and the reaction mixture was incubated for 30 min at 65° C. The DNA was extracted once with phenol/chloroform, precipitated with 2.0 volumes of EtOH, resuspended in 98% formamide-dye, and electrophoresed on a 6% acrylamide, 7 Murea sequencing gel.

DNA Binding Gel Electrophoretic Assays-For this analysis, 6 to 10 µg of nuclear extracts were preincubated for 15 min at 4° C. in a 20 µl reaction containing 25 mM Hepes, pH 7.6, 8% Ficoll, 40 mMKCl, 1 mM dithiothreitol, 3 µg of double-stranded poly(dI-dC), and 5 mM MgCl$_2$ in the presence or absence of 25- to 600-fold excess of competitor oligonucleotide sequences (see Fried et al. Nuc. Acid. Res. 9: 6505–6525, 1981). The sequence of synthetic oligonucleotides used as competitors is presented in Table 3. Next, 30,000 cpm of labeled double-stranded apoA-II oligonucleotide was added, and the incubation continued for 30 min at 4° C. Free DNA and DNA-protein complexes were resolved on a 4% polyacrylamide gel in 1×TAE (1×TAE=6.7 mM Tris, 3.3 mMsodium acetate, 1 mM EDTA, pH 7.9) (27). The gel was dried and exposed to x-ray film. C/EBPα cDNA (Landschulz et al. Genes Dev. 2:786–800, 1988) was the generous gift of Dr. McKnight of Carnegie Institution of Washington and was expressed in *Escherichia coli* and purified as described (Papazafiri et al. J. Biol. Chem. 266:5790–5797, 1991). Extracts from COS-1 cells transiently transfected with HNF4, ARP1, EAR2, and EAR3 expression plasmids were prepared as described in Ladias et al. J. Biol. Chem. 267:15849–15860.

TABLE 3

Sequences of Competitor Oligonucleotides

| NAME | SEQUENCE | SEQ ID NO: |
|---|---|---|
| AIC | $^{-178}$AGCTTGCTGTTTGCCCACTCTATTTGCCCAGCCCCAG$^{-142}$ | 35 |
| AID | $^{-218}$GCCCCCACTGAAACCCTTGACCCCTGCCCTGC$^{-188}$ | 36 |
| AIIH | $^{-573}$TCTCATTACACATTAACTC$^{-553}$ | 37 |
| AIIN | $^{-905}$TATCTATTTAACTGATTTCACCCAA$^{-877}$ | 38 |
| CIIIB | $^{-92}$GGTCAGCAGGTGACCTTTGCCCAGCG$^{-67}$ | 39 |
| CIIIC | $^{-138}$CCGCTTGCTGCATCTCTGGACA$^{-119}$ | 40 |
| CIIID | $^{-165}$GTCCTAGGGATTTCCCAACTCTCCCGCCC$^{-137}$ | 20 |
| BA1 | $^{-88}$CCCGGGAGGCGCCCTTTGGAGCTTTTG$^{-62}$ | 41 |
| BA2 | $^{-61}$CAATCCTGGCGCTCTTGCAGCCTGGG$^{-36}$ | 42 |
| BA3 | $^{-78}$GCCCTTTGGACCTTTTGCAATCCTGGCGCT$^{-49}$ | 43 |
| BC1 | $^{-116}$GCCAGTGTAGAAAAGCAAA$^{-98}$ | 44 |
| α1AT1 | $^{-130}$ATCCCAGCCAGTGGACTTAGCCCCTGTTTGCTCCTCC$^{-93}$ | 18 |
| HNF1/LFB1 | $^{-70}$AGTATGGTTAATGATCTACAG$^{-50}$ | 45 |
| NFY | $^{-92}$GGAACCAATGAAATGCGAGG$^{-73}$ | 24 |
| NF1 | $^{-133}$ACAATTTTTTGGCAAGAATATTAT$^{-110}$ | 46 |
| A1bD | $^{-115}$TGGTATGATTTTGTAATGGGGTAGGA$^{-90}$ | 47 |
| TK/CEBP | $^{-96}$GCGTCTTGTCATTGGCGAATTCG$^{-74}$ | 27 |
| AP1 | $^{-110}$AGCCGCAAGTGACTCAGCGCGGGGCGTGTGCA$^{-77}$ | 48 |
| AP2/3 | $^{-225}$GTTAGGGTGTGGAAAGTCCCCAGGCTCCCCAG$^{-224}$ | 49 |

TABLE 3-continued

Sequences of Competitor Oligonucleotides

| NAME | SEQUENCE | SEQ ID NO: |
|---|---|---|
| OTF | $^{-74}$TTCCCAATGATTTGCATGCTCTCACT$^{-49}$ | 50 |
| AIIAB | $^{-67}$AGTCCTGTCACCTGACAGGGGGTGGGTAAACAGACA$^{-32}$ | 51 |
| AIIBMI | $^{-71}$CCATAGTCCTTATCTATGATAGTCGGTGGGTAAACAGACA$^{-32}$ | 52 |
| AIIC | $^{-128}$CTCCCCCATTTCTCCAACTTG$^{-108}$ | 53 |
| AIID | $^{-278}$TGCTTCCTGTTGCATTCAAGTCCAAG$^{-253}$ | 54 |
| AIIE | $^{-349}$ATAATGGAATAAAGACAC$^{-362}$ | 55 |
| AIIF | $^{-406}$GATAAGGTTGAGAGATGAGATCTAC$^{-382}$ | 56 |
| AIIG | $^{-471}$GATTTCAATTCCTTTCTC$^{-454}$ | 57 |
| AIIH | $^{-572}$GTCTCATTACACATTAACTC$^{-555}$ | 58 |
| AIII | $^{-706}$ATTCACCTCTTTTCCTGCCAGAGCCC$^{-681}$ | 59 |
| AIIJ | $^{-739}$TGCCTTCAACCTTTACCCTGGTAG$^{-716}$ | 60 |
| AIIK | $^{-760}$TAAGGTGATCAAATGACC$^{-745}$ | 61 |
| AIIKM1 | $^{-772}$GCCTAGAACTGATATCTCGATCAAAATACCAGGT$^{-739}$ | 62 |
| AIIL | $^{-810}$GGCTATTGCCCCTGCTGACTCAATATTGGCTAATCACT$^{-773}$ | 63 |
| AIILM1 | $^{-810}$GGCTATTGCCCCTGCTGACTCAATATATGGCTAATCACT$^{-773}$ | 64 |
| AIILM2 | $^{-810}$GGCTATTGCCCCTGCTCAGTCAATATTGGCTAATCACT$^{-773}$ | 65 |
| AIIM | $^{-885}$ACCTCTCCCCCTCCCCCACCCCCAACAGGA$^{-826}$ | 66 |

Methylation Interference Assay—For this analysis, each strand of the synthetic oligonucleotide corresponding to the apoA-II region −903 to −879 was labeled at the 5'-end with T4 polynucleotide kinase and [γ-$^{32}$P]ATP. Each labeled strand was annealed with the unlabeled complementary strand, and the 5'-labeled double-stranded oligonucleotides (4×10$^6$ cpm) were partially methylated at G residues using dimethyl sulfate (Maxam et al. Proc. Natl. Acad. Sci. U.S.A. 74: 560–564, 1977). The methylated probes were incubated with rat liver nuclear extracts and analyzed by preparative DNA binding gel electrophoretic assay. The complexed and free oligonucleotides detected by autoradiography were excised from the gel, purified by electroelution, and treated with 1 Mpiperidine at 90° C. for 30 min (Maxam et al. supra). The samples were subsequently analyzed by electrophoresis on 20% acrylamide/urea sequencing gel and autoradiography.

Fractionation of Nuclear Extracts, DNase I Footprinting, and Competition Assays using Fractionated Extracts—Rat liver nuclear extracts were prepared as described in Gorski et al. Cell 47: 767–776, 1986. 20 ml of nuclear extracts; (220 mg of protein) were dialyzed against two changes of nuclear dialysis buffer (NDB) (25 mM Hepes, pH 7.6 5 mM MgCl$_2$, 0.1 mMEDTA, 10% glycerol, 1 mM dithiothreitol, 0.1 nMbenzamidine, 2 μg/ml aprotinin, 1 μg/ml papstatin, and 1 μg/ml leupeptin added just prior to use) containing 40 mMKCl and were used for purification. The extracts were heated at 85° C. for 5 min using a dry block and the precipitate was removed by centriguation at 10,000 rpm for 5 min at 4° C. The supernatant was loaded onto a column (1.5×10 cm) of Bio-Rex 70 (2.5-ml bead volume) equilibrated in NDB containing 40 mMKCl. The column was eluted stepwise with NDB containing 0.2, 0.3, and 0.4MKCl. The 0.4M KCl fraction was diluted to 4 mM KCl. The 0.4M KCl fraction was diluted to 40 mMKCl, applied to a 1-ml MonoS column, and eluted with a linear gradient of 0.2–0.6 MKCl. In another purification, 20 ml of nuclear extracts (200 mg of protein) in NDB containing 40 mM KCl were applied to a column (2.5×20 cm) of Q-Sepharose (25-ml bead volume) equilibrated in NDB containing 40 mMKCl at a flow rate of 60 ml/h. The column was eluted stepwise with NDB containing 0.1, 0.2 and 0.3M KCl. Fractions eluating at 0.2 MKCl from the Q-Serpharose column containing the NFY and CIIIB1 type activities were used for methylation interference analysis. The fraction eluting at 0.3 MKCl from the BioRex 70 column and the 0.4 and 0.45 Mfractions of the MonoS column were utilized further in DNA binding, protection assays, DNase I footprinting, and competition assays. A synthetic DNA fragment corresponding to apoA-II region −911 to −614 was generated by DNA amplification and was used for footprinting analysis. The 5'-primer was labeled with [γ-$^{32}$P]ATP and T4 polynucleotide kinase prior to polymerase chain reaction amplification. Footprint analysis was performed in a 20-μl reaction containing 25 mMHepes, pH 7.6, 40 mMKCl, 5 mM MgCl$_2$ 0.1 mM EDTA, 10% glycerol, 1 mM dithiothreitol, 1 μg of double-stranded poly(dI-dC), 18–72 μg of nuclear extracts, and 1.5×10$^4$ cpm end-labeled fragment. For competition experiments, the competitor DNA was added at 50–100 fold molar excess. Following incubation for 90 min at 4° C., 2 μl of DNase I, freshly diluted to a final concentration of 20–140 μg/ml in 25 mM CaCl$_2$, were added; and the digestion was allowed to proceed for 5 min at 4° C. The reaction was stopped by the addition of 4 μl of 125 mMTris-HCl, pH 8.0, 125 mMEDTA, and 3% sodium dodecyl sulfate. 40 μg of proteinase K and 5 μg of tRNA were added, and the reaction mixture was incubated for 30 min at 65° C. The DNA was extracted once with phenol/chloroform; precipitated with 2.5 volumes of EtOH; resuspended in 98% formamide/dye; and electrophoresed on a 6% acrylamide, 7Murea sequencing gel.

Fractionation of Activities Bound to the Regulatory Elements J and D of the apoA-II Promoters. All buffers contained 1 mM DTT, 0.1 mM benzamidine, 2 μg/mL aprotinin, 1 μg/mL pepstatin, and 1 μg/mL leupeptin added just prior to use. Nuclear dialysis buffer (NDB) contained 25 mM Hepes (pH 7.6), 5 mM MgCl$_2$, 0.1 mN EDTA, and 10% glycerol. All purification steps were carried out at 4° C. Nuclear extracts were prepared from the livers of 10 rats (approximately 120 g of liver) as described (Gorski et al. 1986). The extracts (10 mL, 90 mg of protein) were dialyzed against two changes of NDB buffer containing 40 mM KCl and used for purification.

Q-Sepharose Chromatography. Five milliliters of dialyzed nuclear extracts were applied to a column (1.6 cm diameter, 20 cm length) of Q-Sepharose (10 ML bead volume) equilibrated in NDB buffer containing 40 mM KCl at a flow rate of 30 mL/h. The column was eluted stepwise with NDB containing 0.2–1M KCl. In this and subsequent fractionations, fractions of 3 mL were collected and analyzed for DNA binding activity by a DNA binding gel electrophoretic assay.

Biorex-70 Chromatography. Another 5 mL of dialyzed nuclear extracts was applied to a column of Biorex-70 similar to that described above and equilibrated in NDB buffer containing 40 mM KCl. The column was eluted stepwise with NDB buffer containing 0.2–1M KCl.

Example 3

Identification and Characterization of Regulatory Elements and Protein Factors Involved in Transcriptional Regulation of the ApoB Gene Materials—Protease inhibitors were purchased from Sigma. Ribonuclease inhibitor RNasin was purchased from Promega Biotech. Q-Sepharose, S-Sepharose, and cyanogen bromide-activated Sepharose 4B were purchased from Pharmacia. Bio-Rex 70 and chromatography columns were purchased from Bio-Rad. Reagents for polymerase chain reaction amplification were purchased from Perkin Elmer Cetus. Other materials were obtained from reported sources (Kardassis et al. Mol. Cell. Biol. 10: 2653–2659, 1990).

Plasmid Constructions and Cat assays—The LM5 CAT construct containing the substitution of nucleotides −97 to −89 was generated using the polymerase chain reaction (PCR) procedure (Ho et al. Gene (Amst) 77: 51–59, 1989). Briefly, two apoB promoter fragments extending from −268 to −74 and −115 to +8 were obtained by PCR amplification and further ligated. The ligated fragments were digested with Asp-718 and cloned into the pUCSH-CAT vector. The fragment −268 to −74 was generated by PCR amplification, using as 3' primer the oligonucleotide PCR-LM5 5'-AGGGCGCCTCCCGGGAAGTCAAGTTTTGCTTTT-CTACACTGG-3'; (SEQ ID NO:93), which corresponds to the antisense strand of the apoB promoter region −115 to −74 and contains the LM5 mutation, and using as a 5' primer the oligonucleotide rev-5-26 (5'-TCACACAGGAAACAGCTATGACCATG-3'; SEQ ID NO:94) that is present upstream of the polylinker region of the pUCSH-CAT vector (Ogami et al. J. Biol. Chem. 265: 9808–9815, 1990).

The fragment −115 to +8 was generated by PCR amplification, using as 5' primer the oligonucleotide PCR-LM5c (5'-CCAGTGTAGAAAAGCAAAACTTGA-CTTCCCGGGAGGCGCCCT-3'; SEQ ID NO:95) corresponding to the sense strand of the apoB promoter region −115 to −74 and also containing the LM5 mutation and using as 3' primer the oligonucleotide PCR-B8R (5'-GGTGGGAATGCGCGGCCGGCGCCCGC-3'; SEQ ID NO:96), which corresponds to the antisense strand of the apoB promoter region −17 to +8. Aliquots containing 4% each of the amplified regions were mixed and used for another round of PCR amplification in the presence of the rev-5–26 and PCR-B8R oligonucleotides. The ligated fragment was digested with Asp-718, gel-purified, and cloned into pUCSH-CAT at the Asp0718 and SmaI sites to generate plasmid LM5 CAT. The LM5 CAT, using the oligonucleotide primers PCR-LM6 (5'-CCAGTGTAGAAAATAAAACAGGTCAGGCCC-3'; SEQ ID NO:97), PCR-LM6c (5'-GGGCCTGACCTGTTTTATTTTCTACACTGG-3'; SEQ ID NO:98) rev-5–26, and PCR-B8R. The mutated promoter plasmids were further verified by DNA sequence analysis. Plasmids LM5 CAT and LM6 CAT were cotransfected with a β-galactosidase-containing plasmid in HepG2 cells by the calcium phosphate-DNA coprecipitation method. CAT and β-galactosidase assays were performed as described in Kardassis et al. Mol. Cell. Biol. 10:2653–2659, 1990 and Ogami et al. J. Biol. Chem. 265:9808–9815, 1990.

Plasmids P10[380] containing the G-minus cassette (Sawadogo et al. Proc. Natl. Acad. Sci. U.S.A. 82: 4394–4398, 1985) and plasmid AdML 404 [180], containing the −404 to +9 region of the adenovirus major late promoter in front of an 180-bp G-minus cassette, were kindly provided by Dr. R. Cortese. The plasmid P10[380] contains 11 guanosine residues at the 3' end of the G-minus cassette (Manaci et al. EMBOJ. 7: 2075–2087, 1988). This plasmid was digested with SstI, blunt ended with T4 polymerase, digested with EcoRI, and ligated with the synthetic oligonucleotide:

5'-AATT CGGTA CCGCC GGCCG CGCAT TCCCA
CC-3'                                                     SEQ ID NO:99

3'-GCCAT GGCGG CCGGC GCGTA AGGGT
GG-5'                                                     SEQ ID NO:100

This oligonucleotide places the apoB promoter sequence from −10 to +8 in front of the G-minus cassette and generates the NaeI site located nine nucleotides upstream of the apoB transcription initiation site. The derivative plasmid was digested with NaeI and ligated with the apoB promoter −268 to −9 NaeI fragment to yield plasmid apoB268[380]. Plasmids containing the mutant apoB promoter region −268 to +8 with nucleotide substitutions in the −77 to −73 region (BM2) and −72 to −68 region (BM3) were constructed in a similar way utilizing the mutated −268 to −9 NaeI fragments (Kardassis et al. Mol. Cell. Biol. 10: 2653–2659, 1990). Plasmid (BA1)$_5$[380] was constructed by blocks of synthetic oligonucleotides containing the apoB promoter sequence from −35 to +8 and five times the BA1 sequence (−79 to −63). The oligonucleotides were cloned in plasmid P10[380] as described above.

Fractionation of Heat-treated Nuclear Extracts—Rat liver nuclear extracts were prepared as described previously (Kardassis et al. J. Biol. Chem. 265: 21733–21740, 1990; Ogami et al. J. Biol. Chem. 265: 9808–9815, 1990). Two hundred mg of crude rat liver nuclear extracts in NDB buffer (25 mM Hepes, pH 7.6, 40 mM KCl, 0.1 mM EDTA, 10% glycerol, 5 mM MgCl$_2$, 1 mM dithiothreitol) (total volume, 20 ml) were aliquoted into Eppendorf tubes (1 ml) and heated at 85° C. for 5 min in a dry heat block. After heat treatment, the extracts were placed on ice for 5 min and centrifuged for 5 min at 4° C. The supernatants were transferred and pooled into a 50-ml tube, and the new protein concentration was measured spectrophotometrically (Kalb et al. Anal. Biochem. 82: 362–371, 1977) (11 mg of protein remained after heat treatment).

These extracts were applied to a 2.5-ml Bio-Rex 70 column equilibrated with NDB containing 0.04M KCl, at a flow rate of 1.5 ml/5 min. After washing the column extensively, the bound proteins were step-eluted with NDB containing 0.2, 0.3, 0.4, 0.5, 0.6, and 1.0M KCl at a flow rate of 1.5 ml/3 min. Half milliliter fractions were collected, and aliquots were tested in gel electrophoretic mobility shift assays. The 0.4M KCl fractions were pooled, dialyzed against NDB buffer, and loaded on a 1-ml Mono-8 FPLC column (Pharmacia KLB Biotechnology Inc.) equilibrated with the same buffer. The extracts were passed through the column at a flow rate of 0.5 ml/min. The column was washed with 5 volumes of NDB, and the bound proteins were eluted with a linear gradient of NDB containing 0.2–0.6M KCl (total volume of gradient, 40 ml). Half-milliliter fractions were collected, and every other fraction was tested in gel electrophoretic mobility shift assay. The concentration of KCl in each fraction was estimated from the chromatographic plot.

Fractionation of Factors Binding to the −115 to −86 (BCB) Region of the apoB Promoter—Eighty mg of crude rat liver nuclear extracts were diluted to 6 mg/ml with NDB containing 0.1M KCl and passed through a 12-ml heparin-Sepharose column equilibrated in 0.1M KCl buffer at a flow rate of 0.5 ml/min using an FPLC apparatus (Pharmacia LKB Biotechnology Inc.). The column was washed with 50 ml of 0.1M KCl, and the bound proteins were eluted stepwise with NDB containing 0.2, 0.3, 0.4, 0.5, and 0.6M KCl (35 ml each). Two-ml fractions were collected, and the peak fractions were tested in gel electrophoretic mobility shift assay using the BCB oligonucleotide as probe (see Table 4).

bromphenol blue, 0.1% xylene cyanol, 5 mM EDTA), electrophoresed on a 6% polyacrylamide, 7M urea sequencing gel, and analyzed by autoradiography.

In the cases where partially purified factors or bacterially expressed C/EBP was used, the footprint assay was performed with 7–13 $\mu$l of factor, 200 ng of poly(dI-dC) competitor, and 20 $\mu$g of bovine serum albumin. In competition experiments, the competitor oligonucleotide was included during the preincubation period. The sequences of the competitor oligonucleotides used are given in Table 5.

TABLE 4

Sequence of apoB Promoter Oligonucleotides

| NAME | SEQUENCE | SEQ ID NO. |
|---|---|---|
| BA | $^{-88}$CCCGGGAGGCGCCCTTTGGACCTTTTGCAATCCTGGCGCTCTTGCAGCCTGGG$^{-36}$ | 67 |
| BA1 | $^{-88}$CCCGGGAGGCGCCCTTTGGACCTTTTG$^{-62}$ | 41 |
| BA2 | $^{-61}$CAATCCTGGCGCTCTTGCAGCCTGGG$^{-36}$ | 42 |
| BA3 | $^{-78}$GCCCTTTGGACCTTTTGCAATCCTGGCGCT$^{-48}$ | 43 |
| BA4 | $^{-72}$TGGACCTTTTGCAATCCT$^{-54}$ | 68 |
| BC1 | $^{-116}$GCCAGTGTAGAAAAGCAA$^{-99}$ | 44 |
| BE | $^{-31}$CTTCTCGGTTGCTGCCGCTGAGGA$^{-52}$ | 69 |
| BCB | $^{-115}$CCAGTGTAGAAAGCAAACAGGTCAGGCCC$^{-86}$ | 70 |

DNaseI Footprinting Assays—The apoB promoter fragment extending from position −268 to +8 was amplified by the polymerase chain reaction procedure, using as 5' and 3'

TABLE 5

Sequence of Competitor Oligonucleotides

| NAME | SEQUENCE | SEQ ID NO: |
|---|---|---|
| CIIIC | $^{-158}$CCGCTTGCTGCATCTGGACA$^{-119}$ | 40 |
| NFY | $^{-92}$GGAACCAATGAAATGGGAGG$^{-73}$ | 24 |
| TK-CEBP | $^{-96}$GCGTCTTGTCATTGGCGAATTCG$^{-74}$ | 27 |
| NF1 | $^{-133}$ACAATTTTTTGGCAAGAATATTAT$^{-110}$ | 46 |
| A1bD | $^{-115}$TGGTATGATTTTGTAATGGGGTAGGA$^{-90}$ | 47 |
| AP1 | $^{-110}$AGCCGCAAGTGACTCAGCGCGGGGCGTGTGCA$^{-77}$ | 48 |
| AP2/3 | $^{-255}$GTTAGGGTGTGGAAAGTCCCCAGGCTCCCCAG$^{-224}$ | 49 | primers the oligonucleotides rev-5-26 and PCR-B8R, respectively (see "Plasmid Constructions and CAT Assays"). The 3' primer was labeled with [$\gamma^{32}$P]ATP and T4 polynucleotide kinase prior to the PCR amplification.

DNaseI footprinting (27, 28) was performed with 55 $\mu$g of rat liver nuclear extracts in a 20-$\mu$l reaction volume containing 25 mM Hepes, pH 7.6, 40 mM KCl, 5 mM MgCl$_2$, 0.1 mM EDTA, 10% glycerol, 1 mM dithiothreitol, and 1 $\mu$g of poly (dI-dC) competitor DNA, unless otherwise indicated. After 15 min on ice, 1–2 ng of end-labeled fragment (10–15,000 cpm) was added, and the incubation was continued for 90 min on ice. Two $\mu$l of DNaseI, freshly diluted to a final concentration of 40–70 $\mu$g/ml in 10 mM CaCl$_2$ was added, and the digestion was allowed to proceed for 5 min on ice. The reaction was stopped by the addition of 4 $\mu$l of 125 mM Tris-HCl, pH 8.0, 125 mM EDTA, and 3% sodium dodecyl sulfate. Forty $\mu$g of Proteinase K and 5 $\mu$g of carrier tRNA were added, and the reaction mixture was incubated for 20 min at 65° C. The DNA was precipitated with 1 vol of 5M ammonium acetate, pH 8.0, and 2 volumes of ethanol, resuspended in formamide dye (98% formamide, 0.1%

Gel Electrophoretic Mobility Shift Assays—Gel electrophoretic mobility shift assays were performed using 6 $\mu$l of partially purified factors in a 20-$\mu$l reaction volume containing 25 mM Hepes, pH 7.6, 8% Ficoll 400, 40 mM KCl, 1 mM dithiothreitol, 5 mM MgCl$_2$, 3 $\mu$g (crude) or 200 ng (partially purified factors) of poly(dI-dC), and varying amounts of competitor oligonucleotides. The competitor oligonucleotides were added 15 min prior to the addition of the labeled probe (see Fried et al. Nuc. Acid. Res. 9: 6505–6525, 1981; Strauss et al. Cell 37: 889–901, 1984). Following a 15-min incubation on ice, 3 fmol (30,000 cpm) of labeled double-stranded oligonucleotide was added, and the incubation continued for 30 min on ice. The reaction mixture was then loaded directly onto a 4% polyacrylamide gel in 1×TAE (10×TAE:67 mM Tris, 33 mM sodium acetate, 10 mM EDTA, pH 7.9) and electrophoresed at 10 Volts/cm of gel for 2–3 h at 4° C. with recircularization of the buffer. After the run, the gel was dried and analyzed by autoradiography. The sequences and the position of oligonucleotides used in the DNA binding experiments are presented in Tables 4, 5 and 6. Bold letters in Table 6 indicate sequences that have been changed relative to the wild type sequence.

TABLE 6

Sequence of BCB mutant Oligonucleotides

| NAME | SEQUENCE | SEQ ID NO: |
|---|---|---|
| BCB | -115CCAGTGTAGAAAGCAAACAGGTCAGGCCC-86 | 70 |
| LM1 | GATATCTAGAAAAGCAAACAGGTCAGGCCC | 71 |
| LM2 | CCAGTGTAGAGATATCAACAGGTCAGGCCC | 72 |
| LM3 | CCAGTGTAGAAAAGCAAACGATATCGGCCC | 73 |
| LM4 | CCAGTGTAGAAAATACCCCAGGTCAGGCCC | 74 |
| LM5 | CCAGTGTAGAAAAGCAAAACTTGACTTCCC | 75 |
| LM6 | CCAGTGTAGAAAATAAAACAGGTCAGGCCC | 76 |
| LM7 | CCAGTGTAGAAAAGCCCACAGGTCAGGCCC | 77 |
| LM8 | CCAGTAGAAAAGCAACAAGGTCAGGCCC | 78 |
| LM9 | CCAGTGTAGAAAAGCAAACCTCTGAGGCCC | 79 |
| LM10 | CCAGTGTAGAAAAGCAAACAGTGCAGGCCC | 80 |
| LM11 | CCAGTGTAGAAAAGCAAACAGGTACGGCCC | 81 |
| LM12 | CCAGTGTAGAAAAGCAAACAGGTCATTCCC | 82 |
| LM13 | CCAGTGTAGACAGTTAAATAGATCAGGCCC | 83 |
| LM14 | CCAGTGTAGACACGCAAACAGGTCAGGCCC | 84 |
| LM15 | CCAGTGTAGCACAGCAAACAGGTCAGGCCC | 85 |
| LM16 | CCAGTGTCTAAAAGCAAACAGGTCAGGCCC | 86 |
| LM17 | CCAGTTGAGAAAAGCAAACAGGTCAGGCCC | 87 |

Purification of Bacterially Expressed Rat C/EBP Protein—The rat C/EBP cDNA, kindly provided by Dr. S. McKnight (Carnegie Institute of Washington, Baltimore, Md.) (Landschultz et al. Genes Dev. 2: 786–800, 1988), was expressed in *Escherichia coli* using the pT7-7 expression vector (Studier et al. Met. Enzymol. 185: 60–89, 1990). Initially, the C/EBP cDNA was amplified using the polymerase chain reaction. The 5'-oligonucleotide used for amplification corresponded to the amino acids 1–9 and contained the initiation codon ATG inside an NdeI restriction site. The 3'-oligonucleotide primer extended from the termination codon TGA to residue 1183 and contained the Asp-718 and HindIII restriction sites. The amplified DNA was digested with NdeI and HindIII, and the C/EBP cDNA fragment was cloned into the corresponding sites of the pT7-7 expression plasmid. The expression of recombinant C/EBP in bacterial cells was performed using the protocol described by Studier et al. (Studier et al. supra). Cell pellets from 2 liters of culture medium were harvested by centrifugation, resuspended in phosphate-buffered saline containing protease inhibitors and 5M urea and lysed by freeze-thawing and sonication. C/EBP was purified from cell lysate by DEAE-cellulose fractionation and heat treatment at 85° C. for 5 min, as previously described (in Landscultz et al. Science 245: 1681–1688, 1989). The resulting fraction contained a major protein of molecular mass of 40 kDa, corresponding to rat C/EBP, and was used for DNA binding and protection assays.

Purification of Nuclear Factor BA1 (NF-BA1) and DNA Binding Studies—All buffers contained 1 mM dithiothreitol, 0.1 mM benzamidine, 2 μg/ml aprotinin, 1 μg/ml pepstatin, and 1 μg/ml leupeptin added just prior to use. NDB buffer contained 25 mM Hepes, pH 7.6, 5 mM $MgCl_2$, 0.1 mM EDTA, and 10% glycerol. All purification steps were carried out at 4° C. A nuclear extract was prepared from livers of 180 rats (approximately 1500 g of liver) as described (in Gorski et al. Cell 47: 767–776, 1986 and Parker et al. Cell 37: 273–283, 1984). The extract (125 ml, 1.733 g of protein) was dialyzed against two changes of NDB buffer containing 40 mM KCl and used for purification.

Step 1

Q-Sepharose Chromatography—The dialyzed nuclear extracts were applied to a column (5×30 cm) of Q-Sepharose (250 ml bead volume) equilibrated in NDB buffer containing 40 mM KCl at a flow rate of 60 ml/h. The column was washed with 3 volumes of the same buffer and was eluted with a linear gradient of NDB containing 40–300 mM KCl. Fractions of 10 ml were collected and analyzed for NF-BA1 activity by DNA-binding gel electrophoresis assays. To fractionate the original 125-ml extracts, this step was performed twice.

Step 2

Bio-Rex 70 Chromatography—Fractions from the Q-Sepharose column containing NF-BA1 activity were pooled and applied directly to a column (5×30 cm) of Bio-Rex 70 (200 ml bead volume) equilibrated in NDB buffer containing 200 mM KCl. The column was washed with the same buffer and eluted stepwise with NDB buffer containing 0.4, 0.5, and 1M KCl. Fractions of 5 ml were collected and analyzed for NF-BA1 activity as described above.

Step 3

S-Sepharose Chromatography—The fractions eluting at 0.4M KCl in Step 2 containing the NF-BA1 activity were adjusted to 100 mM KCl by dilution with NDB and applied to a column (2.5×20 cm) of S-Sepharose (80 ml bead volume) equilibrated in NDB containing 100 mM KCl. The column was washed with the same buffer and eluted stepwise with NDB containing 0.2, 0.3, and 0.4M KCl. Fractions of 4 ml were collected and analyzed for NF-BA1 activity as above. The 0.3M KCl fractions containing the NF-BA1 activity were pooled, adjusted to 100 mM KCl and 10 μg/ml of sonicated salmon sperm DNA, and used for affinity chromatography.

Step 4

DNA Sequence-specific Affinity Chromatography—The double-stranded synthetic oligonucleotide:

| 5'-TTG CGCCC TTTGG ACCTT-3' | SEQ ID NO:101 |
|---|---|
| 3'-GCGGG AAACC TGCAA AAC-5' | SEQ ID NO:102 | corresponding to the apoB promoter sequence (−80 to −63) was polymerized to form oligomers and coupled to cyanogen bromide-activated Sepharose 4B as described (Kadonaga et al. Proc. Natl. Acad. Sci. U.S.A. 83: 5889–5893, 1986). One hundred-thirty-five milliliters (25 mg of protein) of the S-Sepharose fraction were loaded onto 10 ml of DNA-specific affinity column equilibrated in NDB containing 0.1M KCl in NDB. Fractions of 1 ml were collected. All the NF-BA1 binding activity was recovered in the 0.5M KCl fractions. The NF-BA1 -containing fractions were pooled and diluted to 0.1M KCl. Three cycles of oligonucleotide affinity chromatography were performed. The active fractions were pooled and concentrated using Mono-Q column chromatography. The NF-BA1 protein eluted from Mono-Q at 0.2–0.3M KCl was dialyzed in NDB containing 40 mM KCl and stored at −70° C.

For this analysis nuclear extracts or various in a 20-μl reaction volume containing 25 mM Hepes, pH 7.6, 8% Ficoll, 40 mM KCl, 1 mM dithiothreitol, 5 mM $MgCl_2$, and varying amounts of poly(dI-dC)(see Fried et al. Nuc. Acid. Res. 9: 6506–6525, 1981). Labeled double-stranded apoB oligonucleotide (−88 to −62; SEQ ID NOs:101 and 102) was added (30,000 cpm), and the incubation continued for 30 min at 4° C. The reaction mixture was then loaded directly onto a 4% polyacrylamide gel in 1×TAE (1×TAE-6.7 mM sodium acetate, 1 mM EDTA, pH 7.9) and electrophoresed at 100 V for 3 h at 4° C. The gel was dried and analyzed by autoradiography.

The apoB (−268 to +8) and apoCIII (−283 to +24) promoter fragments were labeled with $[\gamma-^{32}P]$ATP at the +8 and +24 nucleotides, respectively, ad described previously (20,28). The apoAI (−264 to +5) and apoAII (−911 to −616) promoter fragments were end-labeled using the polymerase chain reaction procedure (Ho et al. Gene (Amst.) 177: 51–59, 1989). Oligonucleotides PCR264AI:5'-GATATCG-GTACCGACCCCACCCGGGAGACCTGCAAGCCTGC-AGACACTC-3' (SEQ ID NO:103) and OL-AI-1c 5'-AT-TAAAATATTGTGTGTAAGCAGCCAGCTCTTG-3' (SEQ ID NO:104) were used for the amplification and labeling of the apoAI promoter region −264 to +5. Oligonucleotides PCRAII3: 5'-CCATGGATCCCTGAACATA-CCCTACCCCCAGTAAAAC-3' (SEQ ID NO:105) and REV-5-26 5'-TCACACAGGAAACAGCTATGACCA-TG-3' (SEQ ID NO:94) were used for the amplification and labeling of the apoAII promoter region −911 to −616. Twenty-five picomoles of each of the oligonucleotides PCR264AI and PCRAII3 were labeled with [γ-$^{32}$P]ATP prior to use. Polymerase chain reactions were performed in 25-μl total volume containing 10 mM Tris-HCl, pH 8.3, 1.5 mM Tris-HCl, pH 8.3, 1.5 mM MgCl$_2$, 0.01% gelatin, 1.25 mM each dNTP, 1 ng of template DNA, 25 pmol of each primer, and 5 units of Taq polymerase. After amplification, the labeled fragments were gel-purified prior to DNase I footprinting analysis. DNaseI footprinting reactions were performed in a total volume of 20 μl containing 25 mM Hepes, pH 7.6, 40 mM KCl, 5 mM MgCl$_2$, 0.1 mM dithiothreitol, 50 ng of poly(dI-DC), 7–13 μl of affinity-purified NF-BA1, and 20 μg of bovine serum albumin, and incubated for 90 min at 40° C. as described in Kardassis et al. Mol. Cell. Biol. 10: 2653–2659, 1990 and Ogami et al. J. Biol. Chem. 265: 9808–9815, 1990.

Photoaffinity Cross-linking—Photoaffinity cross-linking of affinity-purified NF-BA1 protein to its cognate DNA sequence containing bromodeoxyuridine was performed by a modification of a previously described procedure (Ogata et al. Proc. Natl. Acad. Sci. U.S.A. 74: 4973–4976, 1977). The single-stranded oligonucleotide 5'-GCGCCCTTTGGACCTTTT-3' (SEQ ID NO:106) corresponding to the coding sequence (−80 to −63; 39 to 56 of SEQ ID NO:12) of the apoB gene was synthesized in an Applied Biosystems 380B model DNA synthesizer using 5-bromodeoxyuridine cyanoethyl phosphoramidite. The end product contained 5 residues of bromodeoxyuridine at positions −65, −66, −72, −73, and −74. The bromodeoxyuridine containing oligonucleotide was annealed to its complementary strand and labeled as described (in Kardassis et al. Mol. Cell. Biol. 10: 2653–2659, 1990 and Ogami et al. J. Biol. Chem. 265: 9808–9815, 1990). Binding reactions contained 0.6 ng of end-labeled probe, 100 ng of salmon sperm DNA, 10 μg of bovine serum albumin, and 2 ng of affinity-purified protein. When indicated, competitor oligonucleotides were added at ng. Samples were incubated as described above, diluted with 1 volume of binding buffer, placed on top of Saran wrap laid on top of a UV lamp (UVG-54 short wavelength 254 nM) and irradiated for 10 min at 4° C. After irradiation, the cross-linked proteins were analyzed by SDS-polyacrylamide gel electrophoresis and autoradiography as described (Zannis Met. Enzymol. 128: 823–851, 1986).

Preparation of Depleted Nuclear Extracts and In Vitro Transcription—Two-hundred-fifty μl of nuclear extracts (10 mg/ml) were mixed with 30 μg of salmon sperm DNA and incubated at 4° C. for 15 min. An aliquot of 50 μl of DNA-specific affinity resin was added, and the sample was rotated at 4° C. for 30 min. The resin was removed by low speed centrifugation, and the supernatant was stored in small aliquots at −70° C. DNA binding gel electrophoretic analysis showed that 80% of the NF-BA1 binding activity was removed from native nuclear extracts by the addition of the DNA-specific affinity resin. In vitro transcription reactions on native or depleted nuclear extracts were performed essentially as described (In Gorski et al. Cell 47: 767–776, 1986). The DNA templates used for transcription included 400 ng of the wild type and mutant apoB plasmid (apoB 268[380]) or the (BA1)$_5$[380] plasmid mixed with 100 ng of the adenovirus major late promoter plasmid (AdML404 [180]) which served as an internal control. Transcription reactions contained 500 ng of DNA template, 300–600 ng of salmon sperm DNA, 25 mM Hepes, pH 7.6, 6 mM MgCl$_2$ 50 mM KCl, 30 units of RNasin in 10% glycerol, 0.6 mM CTP, 35 μM UTP, 7 μCi of [α-$^{32}$P]UTP, 0.1 mM EDTA, 0.1 mM 3'-O-methyl-GTP, and 40 μg of nuclear extract in a total volume of 20 μl. In competition experiments the competitor oligonucleotide was added and incubated with the nuclear extract at 4° C. for 10 min prior to the addition of the DNA template. The reactions were performed at 30° C. for 45 min. Each reaction was terminated by the addition of 5 μl of stop buffer (final concentration 50 mM Tris-HCl, pH 7.5, 1% SDS, 100 μg/ml proteinase K, and incubated at 65° C. for 20 min. The RNA produced was EtOH precipitated, dried, dissolved in sequence loading buffer (85% formamide, 0.01% bromphenol blue, and 0.091% xylene cyanol), and electrophoresed on 6% polyacrylamide-7M urea sequencing gel.

Example 4
Characterization and Purification of the CIIIB1 Protein Transcription Factor Materials—Bromodeoxyuridine cyanoethyl phosphoramidite was purchased from Cruachem, Inc. (Bend, Oreg.). Protease inhibitors leupeptin, pepstatin, aprotinin, benzamidine, and phenylmethylsulfonyl fluoride were purchased from Sigma. Polynucleotide kinase, double-stranded poly(dI-dC), anion-exchange (Q-Sepharose) and cation-exchange (S-Sepharose) chromatography columns, and cyanogen bromide-activated Sepharose 4B were purchased from Pharmacia LKB Biotechnology Inc. The cation-exchange chromatography column (Bio-Rex 70) and the silver stain kit were purchased from Bio-Rad. All other reagents were purchased from sources described previously (Ogami et al. J. Biol. Chem. 265: 9808–9815, 1990; Kardassis et al. J. Biol. Chem. 265: 21733–21740, 1990).

Bromodeoxyuridine cyanoethyl phosphoramidite was purchased from Cruachem, Inc. (Bend, Oreg.). Protease inhibitors leupeptin, pepstatin, aprotinin, benzamidine, and phenylmethylsulfonyl fluoride were purchased from Sigma. Polynucleotide kinase, double-stranded poly(dI-dC), anion-exchange (Q-Sepharose) and cation-exchange (S-Sepharose) chromatography columns, and cyanogen bromide-activated Sepharose 4B were purchased from Pharmacia LKB Biotechnology Inc. The cation-exchange chromatography column (Bio-Rex 70) and the silver stain kit were purchased from Bio-Rad. All other reagents were purchased from sources described previously (Ogami et al. J. Biol. Chem. 265: 9808–9815, 1990; Kardassis et al. J. Biol. Chem. 265: 21733–21740, 1990).

Purification of Nuclear Factor CIIIB1—All buffers contained 1 mM dithiothreitol, 0.1 mM benzamidine, 2 μg/ml aprotinin, 1 μg/ml pepstatin, and 1 μg/ml leupeptin added just prior to use. All purification steps were carried out at 4° C. Nuclear extracts were prepared from livers of 180 rats (approximately 1500 g of liver) as described (Gorski et al. Cell 47: 767–776, 1986). The extract (125 ml, 1.733 g of protein) was dialyzed against two changes of NDB[1] buffer (25 mM Hepes, pH 7.6, 5 mM MgCl$_2$, 0.1 mM EDTA, and 10% glycerol) containing 40 mM KCl and used for purification. The DNA binding activity throughout the purification was followed by DNA binding gel electrophoretic assays using the $^{32}$P-labeled −92 to −67 apoC-III oligonucleotide CIIIB (WT) (SEQ ID NO:39) as a probe which binds both CIIIB1 and CIII2.

[1]The abbreviations used are: NDB, nuclear dialysis buffer; Hepes, 4-(2-hydroxyethyl)-1-piperazineethanesulfonic acid; SDS, sodium dodecyl sulfate; WT, wild type.

The activity of each fraction is expressed in units where 1 unit is the amount of protein bound to 1 ng of oligonucleotide probe. For these calculations, DNA binding assays were performed at an optimum concentration of competitor salmon sperm DNA which ensured maximum specific binding. This concentration varied from 3 μg per reaction for the crude extracts to 50 ng per reaction for the fractions eluted from the first affinity column. With the exception of the affinity-purified fraction, the protein concentration was estimated spectrophotometrically based on the $A_{230}$ and $A_{260}$ absorbance measurements as described (Kalb et al. Anal. Biochem. 82: 362–371). The protein concentration following affinity purification was estimated from the total units of DNA binding activity present in the purified fraction. For this estimation, we assume that a protein of $M_r$ 41,000 bind either as a monomer or a dimer to one molecule of the −92 to −67 apoC-III oligonucleotide. This estimation also assumes that the purified CIIIB1 fully maintains its binding activity.

Step 1

Q-Sepharose Chromatography-The dialyzed nuclear extracts were applied to a column (5×30 cm) of Q-Sepharose (250-ml bead volume) equilibrated in NDB buffer containing 40 mM KCl at a flow rate of 60 ml/h. The column was eluted stepwise with NDB containing 01., 02., and 0.3M KCl. In this and subsequent steps 2 and 3 fractions of 4–10 ml were collected and analyzed for CIIIB1 activity by DNA binding gel electrophoretic assay.

Step 2

Bio-Rex 70 Chromatography—Fractions eluting at 0.2M KCl from the Q-Sepharose column containing CIIIB1 activity were pooled and directly applied to a column (5×30 cm) of Bio-Rex 70 (200-ml bead volume) equilibrated in NDB buffer containing 200 mM KCl. The column was eluted stepwise with NDB buffer containing 0.4, 0.5 and 1M KCl.

Step 3

S-Sepharose Chromatography-The fractions eluting at 0.4M KCl in Step 2 containing the CIIIB1 activity were adjusted to 100 mM KCl by dilution with NDB and applied to a column (2.5×20 cm) of S-Sepharose (80-ml bead volume) equilibrated in NDB containing 100 mM KCl. The column was eluted stepwise with NDB containing 0.2, 0.3, and 0.4M KCl. The 0.2M KCl fractions containing the CIIIB1 activity were pooled, adjusted to 100 mM KCl and 10 μg/ml of sonicated salmon sperm DNA, and used for affinity chromatography purification.

Step 4

DNA Sequence-specific Affinity Chromatography—The ligand used for the affinity chromatography was the double-stranded synthetic oligonucleotide as follows.

5'-AGG TCAGC AGGTG ACGAC AGATC AGCAG GTGAC
GACAG A-3'                                    SEQ D NO:107

3'-AGTCG TCCAC TGCTG TCTAG TCGTC CACTG CTGTC
TTCC-5'                                       SEQ ID NO:108

This oligonucleotide is a dimer of the −90 to −73 apoC-III sequence carries substitutions of nucleotides −78 to −75 and −73. Prior mutagenesis experiments indicate that this mutated sequence (CIIIBM5) contains the binding site for CIIIB1 but not CIIIB2 factor (Ogami et al. J. Biol. Chem. 265: 9808–9815, 1990). This sequence was polymerized to form oligomers containing an average of 15 copies and coupled to cyanogen bromide-activated Sepharose 4B as described (in Kadonaga et al. Proc. Natl. Acad. Sci. U.S.A. 83: 5889–5893, 1986). 99 ml (138 mg of protein) of the S-Sepharose fraction adjusted to 0.1M KCl and 10 μg/ml of sonicated salmon sperm DNA were loaded onto the DNA sequence-specific affinity column equilibrated in NBD containing 0.1M KCl. The column was eluted with a step gradient of 0.5M and 1M KCl in NBD. Fractions of 1 ml were collected. All the CIIIB1 binding activity was recovered in the 0.5M KCl fractions. The CIIIB1-containing fractions were pooled and diluted to 0.1M KCl with NDB and reloaded onto the same regenerated affinity column. The column was regenerated by washing the resin with 2.5M NaCl and was equilibrated in NDB containing 0.1M KCl. The active fractions obtained by affinity purification were pooled and concentration with Mono-Q column chromatography. The CIIIB1 protein eluted from Mono-Q at 0.2–0.3M KCl was dialyzed in NBD containing 40 mM CK1 and heated at 85° C. for 5 min. Protein aggregates were removed by centrifugation and the supernatant was stored at −70° C.

DNA Binding and DNA Protection Assays—DNA binding gel electrophoretic assays were performed with crude nuclear extracts and purified CIIIB1 fractions as described (in Ogami et al. J. Biol. Chem. 265: 9808–9815, 1990) using the apoC-III −92 to −67 oligonucleotide (SEQ ID NO:39) as a probe (Table 7). This oligonucleotide and the other oligonucleotides of Table 7, used for DNA binding and competition, carry GGG or CCC overhands on the 5' ends of sense and antisense sequences, respectively. The oligonucleotides used as probes were labeled with [α-$^{32}$P]GTP and [α-$^{32}$P]CTP with the Klenow fragment of DNase polymerase I. DNase I footprinting was performed as described in Ogami et al. id with the affinity-purified heat-treated fractions. The apoC-III (−163 to +24) fragment was labeled with [γ-$^{32}$P]ATP at nucleotides +24 and −163. The apoA-II (−230 to +29) fragment was similarly labeled at nucleotide +29 and used for footprinting analysis.

TABLE 7

Sequence of Competitor Oligonucleotides

| NAME | SEQUENCE | SEQ ID NO: |
|---|---|---|
| HNF1/LFB1 | $^{-70}$AGTATGGTTAATGATCTACAG$^{-50}$ | 45 |
| NFY | $^{-92}$GGAACCAATGAAATGCGAGG$^{-75}$ | 24 |
| NF1 | $^{-133}$ACAATTTTTTGGCAAGAATATTAT$^{-110}$ | 46 |
| A1bD | $^{-115}$TGGTATGATTTTGTAATGGGGTAGGA$^{-90}$ | 47 |
| TK/CEBP | $^{-96}$GCGTCTTGTCATTGGCGAATTCG$^{-74}$ | 27 |
| AP1 | $^{-110}$AGCCGCAAGTGACTCAGCGCGGGGCGTGTGCA$^{-77}$ | 48 |

TABLE 7-continued

Sequence of Competitor Oligonucleotides

| NAME | SEQUENCE | SEQ ID NO: |
|---|---|---|
| AP2 | $^{-255}$GTTAGGGTGTGGAAAGTCCCCAGGCTCCCCAG$^{-224}$ | 49 |
| OTF | $^{-74}$TTCCCAATGATTTGCATGCTCTCACT$^{-49}$ | 50 |
| BA3 | $^{-78}$GCCCTTTGGACCTTTTGCAATCCTGGCGCT$^{-49}$ | 43 |
| CIIIB(WT) | $^{-92}$GGTCAGCAGGTGACCTTTGCCCAGCG$^{-67}$ | 39 |
| CIIIBM1 | GGTCAGATATCGACCTTTGCCCAGCG | 88 |
| CIIIBM2 | GGTCAGCAGGATATCTTTGCCCAGCG | 89 |
| CIIIBM5 | GGTCAGCAGGTGACGACAGA | 90 |

Photoaffinity Cross-linking—Photoaffinity cross-linking of affinity-purified CIIIB2 protein to its cognate DNA sequence containing bromodeoxyuridine was performed by a modification of a procedure described in Ogata et al. Proc. Natl. Acad. Sci. U.S.A. 83: 5889–5893, 1986. The single-stranded oligonucleotide CCCTCTGTCGTCACCTGCTGACC, corresponding to the mutated noncoding (CIIIBM5; SEQ ID NO:90) sequence (−73 to −92 and 3 C. residues at the 5' end) of apoC-III, was synthesized in an Applied Biosystems 380B model DNA synthesizer with 5-bromodeoxyuridine cyanoethyl phosphoramidite. The end product contains 3 residues of bromodeoxyuridine at positions −80, −85, and −88 and has a MT of 8,000. The bromodeoxyuridine-containing oligonucleotide was labeled as described above and annealed to its complementary strand. Binding reactions contained 0.6 ng (100,000 cpm) of end-labeled probe, 100 ng of salmon sperm DNA, 10 µg of bovine serum albumin, and 18 ng of affinity-purified protein. When indicated, competitor oligonucleotides were added at 100 ng. Samples were incubated as described above, diluted with 1 volume of binding buffer, placed on top of Saran™ wrap laid on top of a UV lamp (UVG-54, short wavelength, 254 nm) and irradiated for 10 min at 4° C. After irradiation, the cross-linked proteins were analyzed by SDS-polyacrylamide gel electrophoresis and autoradiography as described.

Expression of the Rat C/EBP cDNA in Bacterial Cells: Purification of the C/EBP Protein—The rat C/EBP cDNA, kindly provided by Dr. McKnight (Landschultz et al. Genes. Dev. 2: 786–800, 1988), was expressed in *Escherichia coli* using the PT7-7 expression vector (Studies et al. Met. Enzymol. 185: 60–89, 1990) C/EBP was purified from cell lysates by DEA-E cellulose fractionation and heat treatment at 70° C. for 5 min as described in Landschultz et al. Science 245: 1681–1688, 1989. The resulting fraction contained a major protein of approximate molecular mass 40 kDa corresponding to rat C/EBP (Landschultz et al. id and was used for DNA binding assays.

Example 5
The Role of Steroid Hormone Superfamily Members HNF-4, ARP-1, EAR-2, and EAR-3 in Apolipoprotein Gene Regulation Plasmid constructions—Construct pMARP1 containing the full length cDNA of ARP-1 in the expression vector pMT2 (Kaufman et al. Mol. Cell. Biol. 9:946–958, 1989) is described in Ladiasetal Science 251:561–565, 1991. Construct pMARP1 was previously referred to as pMA. All other plasmid constructs were made using standard procedures (Sambrook et al. Molecular cloning: A Laboratory Manual, New York: Cold Spring Harbor Press, 1989 (2nd Gd), incorporated herein by reference. The structures of the resulting constructs were verified by restriction mapping and limited nucleotide sequencing.

The EAR-3 cDNA was derived from a HeLa 1ft11 library (Clontech), using as probe a DNA fragment corresponding to ARP-1 DNA binding domain. The 5' untranslated region of EAR-3 was modified using the polymerase chain reaction (PCR) (Saiki et al. Science 23A: 487–491, 1988) with the primer 5'-GACGCAGAATTCAAGCTTGCCGCCGCCA-TGGCAATGGTAGTTAGCAGCTGGCGAG-3' (SEQ ID NO:109) which provides a strong translation initiation sequence specified by Kozak (Kozak J. Cell Biol. 108: 229–241, 1989), a primer corresponding to the SP6 promoter and the EAR-3 cDNA closed in pGEM-7Zf(—) as a template. The PCR product was closed in the EcoRI site of pMT2 vector, to generate construct pMEAR3.

Plasmid ev2 that contains the human EAR-2 cDNA in the pGEM-3Zf(-) vector, was a kind gift from Dr. Tadashi Yamamoto of the University of Tokyo. The EAR-2 cDNA was excised from the vector and closed in the EcoRI site of pMT2, using EcoRI linkers (New England Biolabs), to generate construct pMEAR2.

HNF-4 was cloned from rat liver lgt1 1 library (Clontech) using PCR and primers (Genosys) based on the published sequence (Sladek et al. Genes Dev. 4:2353–2365, 1990). The forward primer 5'-GACAGAATTCGCCGCCGCCAT-GGACATGGCTGACTACAGTGCT-3' (SEQ ID NO:110) which provides a strong translation initiation sequence specified by Kozak, and the reverse primer 5'-GACAGAATTCAAGCTTTCTCTGAGGGTGGGAG-CCAGCAGAAGCCT-3' (SEQ ID NO:111) were used in a PCR containing ~2×10$^7$ recombinants as described in Sladek et al. id. The PCR product was digested with EcoRI and closed in the EcoRI site of pMT2 vector to generate construct pMHNF4.

The construction of a series of reporter plasmids containing 5' deletion or substitution mutations of the apoB, apoCIII, and apoAII promoters ligated to the chloramphenicol acetyltransferase (CAT) gene have been previously in Kardassis et al. Mol. Cell. Biol. 10:2653–2659, 1990; Ogami et al. J. Biol. Chem. 265:9808–9815; and Chambaz et al. J. Biol. Chem 266, 11676–11685, 1991.

Cell transfections and CAT assays—HepG2 cells were maintained as stocks in Dulbecco's modified Eagle's medium (DMEM) supplemented with 10% fetal calf serum (FCS). Fifty to 60% confluent 60-mm dishes were transfected using the calcium-phosphate DNA coprecipitation method (Graham et al. Virology 52:456–467, 1973). The transfection mixture contained 6 µg of promoter plasmid DNA, 6 µg of either pMHNF4, pMARP1, pMEAR2, and pMEAR3 plasmids, and 5 ug of β-galactosidase plasmid (Edlund et al. Science 230: 912–916, 1985). Cells were harvested 42 h later and lysed by freeze-thawing. CAT assays were performed in a total volume of 150 µl, 0.47M Tris-HCl buffer pH 7.8 containing 0.5 µCi of [$^{14}$C] chloramphenicol and 0.53 mM acetyl-CoA as described (in Gorman et al. Mol. Cell.

Biol. 2;1044–1051, 1982). The reaction times and extract concentrations were selected to ensure linear conversions of the chloramphenicol to the acetylated forms. The non-acetylated and acetylated chloramphenicol forms were separated in OB2 silica gel plates using chloroform/methanol 95:5 for development. The radioactive spots, detected by autoradiography, were scraped from the thin layer plates and counted. The β-galactosidase activity of the cell lysates was determined as described in Edlund et al. Science 230: 912–916, 1985 and the values were used to normalize variabilities in the efficiency of transfection.

Preparation of extracts from COS-1 transfected cells— COS-1 cells were maintained as stocks in DMEM supplemented with 10% FCS. Fifty to 60% confluent 150-mm dishes were transfected with 42 ug of pMHNF4, pMARP1, pMEAR2, and pMEAR3 plasmids. Forty hours after transfection cells were collected in 40 mM Tris-HCl pH 7.4, 1 mM EDTA, 0.15M NaCl and pelleted by low speed centrifugation. Cells were resuspended in 400 $\mu$l of a buffer containing 20 mM Tris-HCl pH 7.4, 0.4M KCL, 2 mM dithiothreotol, 10% glycerol, 1 mM dithiothreitol, 3 $\mu$g of poly (dI-dC) competitor DNA, and 3–6 $\mu$l of whole cell extracts obtained from transiently transfected COS-1 cells expressing HNF-4, ARP-1, EAR-2, and EAR-3. After 15 min on ice, 10–15,000 cpm of end-labeled fragment was added and the incubation contained for 90 min on ice. Two $\mu$l of DNase I, freshly diluted to a final concentration of 150 ug/ml in 10 mM $CaCl_2$ was added and the digestion was allowed to proceed for 5 min on ice. The reaction was stopped by the addition of 4 $\mu$l of 125 mM Tris-HCl pH 8.0, 125 mM EDTA and 3% SDS. Forty $\mu$g of Proteinase K and 5 ug of carrier tRNA were added and the reaction mixture was incubated for 20 min at 65° C. The DNA was precipitated with 1 vol of 5M Ammonium Acetate pH 8.0 and 2 vol of Ethanol, resuspended in formamide dye (98% formamide, 0.1% Bromophenol blue, 0.1% xylene cyanol, 5mM EDTA, electrophoresed on a 6% polyacrylamide, 7M urea sequencing gel and analyzed by autoradiography.

Gel electrophoretic mobility shift assays—Gel electrophoretic mobility shift assays were performed in a 20 $\mu$l reaction volume containing 25 mM Hepes pH 7.6, 8% Ficoll 400, 40 mM KCl, 1 mM dithiothreitol, 5 mM $MgCl_2$, 1 $\mu$g of poly(dI-dC) and varying amounts (1–5 $\mu$l) of whole cell extracts diluted 10-fold (See Fried et al. Nuc. Acid Res. 9:6505–6525, 1981; Strauss et al. Cell 37:889–901, 1984). When indicated 20 ng of competitor oligonucleotides were added 15 min prior to the addition of the labeled probe. Following a 15 min incubation on ice, 3 fmoles (30,000 cpm) of the labeled double-stranded oligonucleotide was added and the incubation continued for 30 min on ice. The reaction mixture was then loaded directly onto a 4% polyacrylamide gel in 1×TAE (10×TAE=67 mM Tris, 33 mM Sodium Acetate, 10 mM EDTA pH 7.9) and electrophoresed at 10 Volts/cm of gel for 2–3 hr at 4° C. with recircularization of the buffer (Strauss et al. id.) Alternatively, gels were fun in 1×TBE at 4° C. without recirculization. After the run, gels were dried and analyzed and autoradiography.

The dissociation constant values (Kd) of ARP-1, EAR-2, and HNG-4 were obtained from binding reactions performed with a constant amount of protein extract and increasing concentrations of radiolabelled BA1 probe (specific radioactivity $0.5 \times 10^9$ cpm/$\mu$g). After gel electrophoresis and autoradiography, the radioactive bands corresponding to the bound and free oligonucleotide were excised and the radioactivity was measured by scintillation spectroscopy. The Kd values were calculated by using the equation $B_p/F_p = 1/K_d \times [B]_p + T_p/K_d$ where $B_P$, $F_P$, and $T_p$ are the bound, free and total (bound+free) radiolabelled oligonucleotide BA1.

Methylation interference—The coding strands of synthetic oligonucleotides BA1 and CIIIB were labeled at the 5' end with T4 polynucleotide kinase and [g-$^{32}$p] ATP. Each labelled strand was annealed with the unlabelled complementary strand as described in Maxam et al. Proc. Natl. Acad. Sci. U.S.A. 74:560–564, 1977. End labelled double-stranded oligonucleotides ($4 \times 10^6$ cpm) were partially methylated at G residues using dimethyl sulphate (DMS) (Maxam et al. id). The methylated probes were incubated with whole cell extracts from COS-1 cells expressing HNG-4, ARP-1, EAR-2, or EAR-3 and the complexes were analyzed in a preparative mobility shift gel. The gel was exposed for 1 hr and both the complexed and free oligonucleotides were excised from the gel, electroeluted and treated with 1M Piperdine at 90° C. for 30 min (Maxam et al. id). The samples were dried, dissolved in 98% formamide dye and electrophoresed on 20% polyacrylamide/urea sequencing gels. Bands were visualized by autoradiography.

EQUIVALENTS

It will be understood that the preceding is merely a detailed description of certain preferred embodiments of the present invention. The detailed description is not meant to be limiting and it will be appreciated by those skilled in the art that various modifications and equivalents can be made without departing from the spirit or scope of the invention.

We claim:

1. An isolated apoA-I gene regulatory sequence element having a nucleotide sequence consisting of the sequence found between nucleotide number 212 and nucleotide number 250 of SEQ ID NO:10.

2. An isolated apoA-I gene regulatory sequence element having a nucleotide sequence consisting of the sequence found between nucleotide number 106 and nucleotide number 157 of SEQ ID NO:10.

3. An isolated apoA-I gene regulatory sequence element having a nucleotide sequence consisting of the sequence found between nucleotide number 59 and nucleotide number 86 of SEQ ID NO:10.

4. An isolated apoA-I gene regulatory sequence element having a nucleotide sequence consisting of the sequence found between nucleotide number 14 and nucleotide number 44 of SEQ ID NO:10.

5. An oligonucleotide having a nucleotide sequence consisting of the binding site portion of an apoA-I gene regulatory sequence element, which apoA-I gene regulatory sequence element is selected from the group consisting of:

element A, consisting of nucleotides 212 to +250 of SEQ ID NO:10;
   element B, consisting of nucleotides 106 to 157 of SEQ ID NO:10;
   element C, consisting of nucleotides 59 to 86 of SEQ ID NO:10; and
   element D, consisting of nucleotides 14 to 44 of SEQ ID NO:10.

6. The oligonucleotide of claim 5, said oligonucleotide being double-stranded.

7. The oligonucleotide of claim 5, said oligonucleotide being single stranded and consisting of the sense strand of said regulatory sequence element.

8. The oligonucleotide of claim 5, said oligonucleotide being single stranded and consisting of the antisense strand of said regulatory sequence element.

9. An oligonucleotide having a nucleotide sequence consisting of multiple copies of the binding site portion of an apoA-I gene regulatory sequence element, which apoA-I gene regulatory sequence element is selected from the group consisting of:

element A, consisting of nucleotides 212 to +250 of SEQ ID NO:10;
   element B, consisting of nucleotides 106 to 157 of SEQ ID NO:10;
   element C, consisting of nucleotides 59 to 86 of SEQ ID NO:10; and
   element D, consisting of nucleotides 14 to 44 of SEQ ID NO:10.

10. A recombinant nucleic acid molecule comprising:

a gene other than apoA-I operably linked to
   an isolated apoA-I gene regulatory sequence element consisting of a nucleotide sequence consisting of a sequence selected from the group consisting of:
      element A, consisting of nucleotides 212 to +250 of SEQ ID NO:10;
      element B, consisting of nucleotides 106 to 157 of SEQ ID NO:10;
      element C, consisting of nucleotides 59 to 86 of SEQ ID NO:10; and
      element D, consisting of nucleotides 14 to 44 of SEQ ID NO:10; and combinations thereof.

* * * * *

SEQUENCE LISTING ( 1 ) GENERAL INFORMATION:

( i i i ) NUMBER OF SEQUENCES: 113

( 2 ) INFORMATION FOR SEQ ID NO:1:

( i ) SEQUENCE CHARACTERISTICS:
        ( A ) LENGTH: 262 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: apoA-II promoter region - 911 to -650

(x i) SEQUENCE DESCRIPTION: SEQ ID NO:1:

| AAGCTTCTGA | TATCTATTTA | ACTGATTTCA | CCCAAATGCT | TTGAACCTGG | GAATGTACCT | 60 |
| CTCCCCCTCC | CCCACCCCCA | ACAGGAGTGA | GACAAGGGCC | AGGCTATTGC | CCCTGCTGAC | 120 |
| TCAATATTGG | CTAATCACTG | CCTAGAACTG | ATAAGGTGAT | CAAATGACCA | GGTGCCTTCA | 180 |
| ACCTTTACCC | TGGTAGAAGC | CTCTTATTCA | CCTCTTTTCC | TGCCAGAGCC | CTCCATTGGG | 240 |
| AGGGACGGGC | GGAAGTGTTT | TC | | | | 262 |

(2) INFORMATION FOR SEQ ID NO:2:

(i) SEQUENCE CHARACTERISTICS:
        (A) LENGTH: 17 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: apoB promoter region -79 to -63

(x i) SEQUENCE DESCRIPTION: SEQ ID NO:2:

| CGCCCTTTGG | ACCTTTT | 17 |

(2) INFORMATION FOR SEQ ID NO:3:

(i) SEQUENCE CHARACTERISTICS:
        (A) LENGTH: 79 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: apoB promoter sequences in apoB-CAT construct (x i) SEQUENCE DESCRIPTION: SEQ ID NO:3:

| GAAGCCAGTG | TAGAAAAGCA | AACAGGTCAG | GCCCGGGAGG | CGCCCTTTGG | ACCTTTTGCA | 60 |
| ATCCTGGCGC | TCTTGCAGC | | | | | 79 |

(2) INFORMATION FOR SEQ ID NO:4:

(i) SEQUENCE CHARACTERISTICS:
        (A) LENGTH: 207 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: apoB promoter sequences - 154 to +53

(x i) SEQUENCE DESCRIPTION: SEQ ID NO:4:

| GGGCCCCCTC | CCCGAGGCTC | TTCAAGGCTC | AAAGAGAAGC | CAGTGTAGAA | AAGCAAACAG | 60 |
| GTCAGGCCCG | GGAGGCGCCC | TTTGGACCTT | TTGCAATCCT | GGCGCTCTTG | CAGCCTGGGC | 120 |
| TTCCTATAAA | TGGGGTGCGG | GCGCCGGCCG | CGCATTCCCA | CCGGGACCTG | CGGGGCTGAG | 180 |
| TGCCCTTCTC | GGTTGCTGCC | GCTGAGG | | | | 207 |

(2) INFORMATION FOR SEQ ID NO:5:

(i) SEQUENCE CHARACTERISTICS:
        (A) LENGTH: 27 base pairs (B) TYPE: nucleic acid
(C) STRANDEDNESS: both
(D) TOPOLOGY: Not Relevant (ii) MOLECULE TYPE: DNA (genomic)

(vii) IMMEDIATE SOURCE:
(B) CLONE: apoB promoter region -88 to -62

(xi) SEQUENCE DESCRIPTION: SEQ ID NO:5:

| CCCGGGAGGC | GCCCTTTGGA | CCTTTTG | | | | 27 |
|---|---|---|---|---|---|---|

(2) INFORMATION FOR SEQ ID NO:6:

(i) SEQUENCE CHARACTERISTICS:
(A) LENGTH: 86 base pairs
(B) TYPE: nucleic acid
(C) STRANDEDNESS: both
(D) TOPOLOGY: Not Relevant (ii) MOLECULE TYPE: DNA (genomic)

(vii) IMMEDIATE SOURCE:
(B) CLONE: apoB promoter elements I to IV (xi) SEQUENCE DESCRIPTION: SEQ ID NO:6:

| AAGCCAGTGT | AGAAAAGCAA | ACAGGTCAGG | CCCGGGAGGC | GCCCTTTGGA | CCTTTTGCAA | 60 |
|---|---|---|---|---|---|---|
| TCCTGGCGCT | CTTGCAGCCT | GGGCTT | | | | 86 |

(2) INFORMATION FOR SEQ ID NO:7:

(i) SEQUENCE CHARACTERISTICS:
(A) LENGTH: 1434 base pairs
(B) TYPE: nucleic acid
(C) STRANDEDNESS: both
(D) TOPOLOGY: Not Relevant (ii) MOLECULE TYPE: DNA (genomic)

(vii) IMMEDIATE SOURCE:
(B) CLONE: apoCIII promoter region - 1411 to +24

(xi) SEQUENCE DESCRIPTION: SEQ ID NO:7:

| GAATTCTGAG | GGCAGAGCGG | GCCACTTTCT | CAGGCCTCTG | ATTTCATACT | GTGGTGTTAG | 60 |
|---|---|---|---|---|---|---|
| TTACTTCTGA | GAGGACAGCT | TGCGCCAGAG | CTCTATTTTT | TATGTTAGAG | GCTCCTTCTG | 120 |
| CCTGCAGACT | CTGCTGTCTG | GGAAGGGCAC | AGCGTTAGGA | GGGAGAGGGA | GGTGTGAGTC | 180 |
| CCTCCGTGGA | CCCGCTGCTT | TGTACTTCTC | TATCTCATTT | CCTTTTCAGC | ACCACTCTGG | 240 |
| GAAATCAGTA | TTCCAGCCCC | ATTTTATCCT | CAGAAAATTG | AGGCTCTGAG | ATGTTATCTC | 300 |
| TGTGACCTGG | GTCCTATTAC | GTGCCAAAGG | CATCATTTAA | GCCTAAGATG | TCCTGGCTCC | 360 |
| AAGGTGTCAG | CATCTGGAAG | ACAGGCGCCC | TCATCCTGCC | ATCCCTGCTG | CGGCTTCACT | 420 |
| GTGGGCCCAG | GGACATCTC | AGCCCCGAGA | AGGTCAGCGG | CCCCTCCTGG | ACCACCGACT | 480 |
| CCCCGCAGAA | CTCCTCTGTG | CCCTCTCCTC | ACCAGACCTT | GTTCCTCCCA | GTTGCTCCCA | 540 |
| CAGCCAGGGG | GCAGTGAGGG | CTGCTCTTCC | CCCAGCCCCA | CTGAGGAACC | CAGGAAGGTG | 600 |
| AACGAGAGAA | TCAGTCCTGG | TGGGGCTGG | GGAGGGCCCA | GACATGAGAC | CAGCTCCTCC | 660 |
| CCCAGGGATG | TTATCAGTGG | GTCCAGAGGG | CAAAATAGGG | AGCCTGGTGG | AGGGAGGGGC | 720 |
| AAAGGCCTCG | GGCTCTGAGC | GGCCTTGGCT | TCTCCACCAA | CCCCTGCCCT | ACACTCAGGG | 780 |
| GGAGGCGGCG | GTGGGGCACA | CAGGGTGGGG | GCGGGTGGGG | GGCTGCTGGG | TGAGCAGCAC | 840 |
| TCGCCTGCCT | GGATTGAAAC | CCAGAGATGG | AGGTGCTGGG | AGGGGCTGTG | AGAGTCAGCC | 900 |
| CTGTAACCAG | GCCTTGCGAG | CCACTGATGC | CCGGTCTTCT | GTGCCTTTAC | TCCAAACATC | 960 |

-continued

| | | | | | |
|---|---|---|---|---|---|
| CCCCAGCCCA | AGCCACCCAC | TTGTTCTCAA | GTCTGAAGAA | GCCCCTCACC | CCTCTACTCC | 1020
| AGGCTGTGTT | CAGGGCTTGG | GGCTGGTGGA | GGGAGGGGCC | TGAAATTCCA | GTGTGAAAGG | 1080
| CTGAGATGGG | CCCGACCCCT | GGCCTATGTC | CAAGCCATTT | CCCCTCTCAC | CAGCCTCTCC | 1140
| CTGGGGAGCC | AGTCAGCTAG | GAAGGAATGA | GGCTCCCCAG | GCCCACCCCC | AGTTCCTGAG | 1200
| CTCATCTGGG | CTGCAGGGCT | GGCGGGACAG | CAGCGTGGAC | TCAGTCTCCT | AGGGATTTCC | 1260
| CAACTCTCCC | GCCCGCTTGC | TGCATCTGGA | CACCCTGCCT | CAGGCCCTCA | TCTCCACTGG | 1320
| TCAGCAGGTG | ACCTTTGCCC | AGCGCCCTGG | GTCCTCAGTG | CCTGCTGCCC | TGGAGATGAT | 1380
| ATAAACAGG | TCAGAACCCT | CCTGCCTGTC | TGCTCAGTTC | ATCCCTAGAG | GCAG | 1434

( 2 ) INFORMATION FOR SEQ ID NO:8:

( i ) SEQUENCE CHARACTERISTICS:
        ( A ) LENGTH: 265 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: apoA-I promoter regions A through D ( x i ) SEQUENCE DESCRIPTION: SEQ ID NO:8:

| | | | | | |
|---|---|---|---|---|---|
| AGACACTCCC | CTCCGCCCC | CACTGAACCC | TTGACCCCTG | CCCTGCAGCC | CCCGCAGCTT | 60
| GCTGTTTGCC | CACTCTATTT | GCCCAGCCCC | AGGGACAGAG | CTGATCCTTG | AACTCTTAAG | 120
| TTCCACATTG | CCAGGACCAG | TGAGCAGCAA | CAGGGCCGGG | GCTGGGCTTA | TCAGCCTCCC | 180
| AGCCCAGACC | CTGGCTGCAG | ACATAAATAG | GCCCTGCAAG | AGCTGGCTGC | TTAGAGACTG | 240
| CGAGAAGGAG | GTGCGTCCTG | CTGCC | | | | 265

( 2 ) INFORMATION FOR SEQ ID NO:9:

( i ) SEQUENCE CHARACTERISTICS:
        ( A ) LENGTH: 940 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: apoA-II promoter regions A through M ( x i ) SEQUENCE DESCRIPTION: SEQ ID NO:9:

| | | | | | |
|---|---|---|---|---|---|
| AAGCTTCTGA | TATCTATTTA | ACTGATTTCA | CCCAAATGCT | TTGAACCTGG | GAATGTACCT | 60
| CTCCCCCTCC | CCCACCCCCA | ACAGGAGTGA | GACAAGGGCC | AGGCTATTGC | CCCTGCTGAC | 120
| TCAATATTGG | CTAATCACTG | CCTAGAACTG | ATAAGGTGAT | CAAATGACCA | GGTGCCTTCA | 180
| ACCTTTACCC | TGGTAGAAGC | CTCTTATTCA | CCTCTTTTCC | TGCCAGAGCC | CTCCATTGGG | 240
| AGGGACGGGC | GGAAGTGTTT | TCTGAATTTG | TTTACTGGG | GGTAGGGTAT | GTTCAGTGAT | 300
| CAGCATCCAG | GTCATTCTGG | GCTCTCCTGT | TTTCTCCCCG | TCTCATTACA | CATTAACTCA | 360
| AAAACGGACA | AGATCATTTA | CACTTGCCCT | CTTACCCGAC | CCTCATTCCC | CTAACCCCCA | 420
| TAGCCCTCAA | CCCTGTCCCT | GATTTCAATT | CCTTTCTCCT | TTCTTCTGCT | CCCCAATATC | 480
| TCTCTGCCAA | GTTGCAGTAA | AGTGGGATAA | GGTTGAGAGA | TGAGATCTAC | CCATAATGGA | 540
| ATAAAGACAC | CATGAGCTTT | CCATGGTATG | ATGGGTTGAT | GGTATTCCAT | GGGTTGATAT | 600
| GTCAGAGCTT | TCCAGAGAAA | TAACTTGGAA | TCCTGCTTCC | TGTTGCATTC | AAGTCCAAGG | 660

| | | | | | |
|---|---|---|---|---|---|
| ACCTCAGATC | TCAAAAGAAT | GAACCTCAAA | TATACCTGAA | GTGTACCCCC | TTAGCCTCCA | 720 |
| CTAAGAGCTG | TACCCCCTGC | CTCTCACCCC | ATCACCATGA | GTCTTCCATG | TGCTTGTCCT | 780 |
| CTCCTCCCCC | ATTTCTCCAA | CTTGTTTATC | CTCACATAAT | CCCTGCCCCA | CTGGGCCCAT | 840 |
| CCATAGTCCT | GTCACCTGAC | AGGGGGTGGG | TAAACAGACA | GGTATATAGC | CCCTTCCTCT | 900 |
| CCAGCCAGGG | CAGGCACAGA | CACCAAGGAC | AGAGACGCTG | | | 940 |

( 2 ) INFORMATION FOR SEQ ID NO:10:

( i ) SEQUENCE CHARACTERISTICS:
        ( A ) LENGTH: 265 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: ApoA-I -233 to +32

( x i ) SEQUENCE DESCRIPTION: SEQ ID NO:10:

| | | | | | |
|---|---|---|---|---|---|
| AGACACTCCC | CTCCCGCCCC | CACTGAACCC | TTGACCCCTG | CCCTGCAGCC | CCCGCAGCTT | 60 |
| GCTGTTTGCC | CACTCTATTT | GCCCAGCCCC | AGGGACAGAG | CTGATCCTTG | AACTCTTAAG | 120 |
| TTCCACATTG | CCAGGACCAG | TGAGCAGCAA | CAGGGCCGGG | GCTGGGCTTA | TCAGCCTCCC | 180 |
| AGCCCAGACC | CTGGCTGCAG | ACATAAATAG | GCCCTGCAAG | AGCTGGCTGC | TTAGAGACTG | 240 |
| CGAGAAGGAG | GTGCGTCCTG | CTGCC | | | | 265 |

( 2 ) INFORMATION FOR SEQ ID NO:11:

( i ) SEQUENCE CHARACTERISTICS:
        ( A ) LENGTH: 940 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
        ( B ) CLONE: Apo A-II -911 to +29

( x i ) SEQUENCE DESCRIPTION: SEQ ID NO:11:

| | | | | | |
|---|---|---|---|---|---|
| AAGCTTCTGA | TATCTATTTA | ACTGATTTCA | CCCAAATGCT | TTGAACCTGG | GAATGTACCT | 60 |
| CTCCCCCTCC | CCCACCCCCA | ACAGGAGTGA | GACAAGGGCC | AGGCTATTGC | CCCTGCTGAC | 120 |
| TCAATATTGG | CTAATCACTG | CCTAGAACTG | ATAAGGTGAT | CAAATGACCA | GGTGCCTTCA | 180 |
| ACCTTTACCC | TGGTAGAAGC | CTCTTATTCA | CCTCTTTTCC | TGCCAGAGCC | CTCCATTGGG | 240 |
| AGGGACGGGC | GGAAGTGTTT | TCTGAATTTG | TTTTACTGGG | GGTAGGGTAT | GTTCAGTGAT | 300 |
| CAGCATCCAG | GTCATTCTGG | GCTCTCCTGT | TTTCTCCCCG | TCTCATTACA | CATTAACTCA | 360 |
| AAAACGGACA | AGATCATTTA | CACTTGCCCT | CTTACCCGAC | CCTCATTCCC | CTAACCCCCA | 420 |
| TAGCCCTCAA | CCCTGTCCCT | GATTTCAATT | CCTTTCTCCT | TTCTTCTGCT | CCCCAATATC | 480 |
| TCTCTGCCAA | GTTGCAGTAA | AGTGGGATAA | GGTTGAGAGA | TGAGATCTAC | CCATAATGGA | 540 |
| ATAAAGACAC | CATGAGCTTT | CCATGGTATG | ATGGGTTGAT | GGTATTCCAT | GGGTTGATAT | 600 |

-continued

```
GTCAGAGCTT  TCCAGAGAAA  TAACTTGGAA  TCCTGCTTCC  TGTTGCATTC  AAGTCCAAGG    660

ACCTCAGATC  TCAAAAGAAT  GAACCTCAAA  TATACCTGAA  GTGTACCCCC  TTAGCCTCCA    720

CTAAGAGCTG  TACCCCCTGC  CTCTCACCCC  ATCACCATGA  GTCTTCCATG  TGCTTGTCCT    780

CTCCTCCCCC  ATTTCTCCAA  CTTGTTTATC  CTCACATAAT  CCCTGCCCCA  CTGGGCCAT     840

CCATAGTCCT  GTCACCTGAC  AGGGGGTGGG  TAAACAGACA  GGTATATAGC  CCCTTCCTCT    900

CCAGCCAGGG  CAGGCACAGA  CACCAAGGAC  AGAGACGCTG                            940
```

( 2 ) INFORMATION FOR SEQ ID NO:12:

( i ) SEQUENCE CHARACTERISTICS:
           ( A ) LENGTH: 86 base pairs
           ( B ) TYPE: nucleic acid
           ( C ) STRANDEDNESS: single
           ( D ) TOPOLOGY: linear ( i i ) MOLECULE TYPE: DNA (genomic)

( i i i ) HYPOTHETICAL: NO ( i v ) ANTI-SENSE: NO ( v i i ) IMMEDIATE SOURCE:
           ( B ) CLONE: Apo B -118 to -33

( x i ) SEQUENCE DESCRIPTION: SEQ ID NO:12:

```
AAGCCAGTGT  AGAAAAGCAA  ACAGGTCAGG  CCCGGGAGGC  GCCCTTTGGA  CCTTTTGCAA    60

TCCTGGCGCT  CTTGCAGCCT  GGGCTT                                           86
```

( 2 ) INFORMATION FOR SEQ ID NO:13:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: DNA (genomic)

( v i i ) IMMEDIATE SOURCE:
           ( B ) CLONE: Apo B +33 to +52

( x i ) SEQUENCE DESCRIPTION: SEQ ID NO:13:

```
TCTCGGTTGC  TGCCGCTGAG  G                                                21
```

( 2 ) INFORMATION FOR SEQ ID NO:14:

( i ) SEQUENCE CHARACTERISTICS:
           ( A ) LENGTH: 21 base pairs
           ( B ) TYPE: nucleic acid
           ( C ) STRANDEDNESS: single
           ( D ) TOPOLOGY: linear ( i i ) MOLECULE TYPE: DNA (genomic)

( v i i ) IMMEDIATE SOURCE:
           ( B ) CLONE: Apo B +33 to +52

( x i ) SEQUENCE DESCRIPTION: SEQ ID NO:14:

```
TCTCGGTTGC  TGCCGCTGAG  G                                                21
```

( 2 ) INFORMATION FOR SEQ ID NO:15:

( i ) SEQUENCE CHARACTERISTICS:
           ( A ) LENGTH: 8 base pairs
           ( B ) TYPE: nucleic acid
           ( C ) STRANDEDNESS: both

```
            ( D ) TOPOLOGY: linear ( i i ) MOLECULE TYPE: DNA (genomic)

( v i i ) IMMEDIATE SOURCE:
            ( B ) CLONE: direct repeat found at - 210 to -203 of apoA-I
                    promoter ( x i ) SEQUENCE DESCRIPTION: SEQ ID NO:15:
```

TGAACCCT                                                                                        8

( 2 ) INFORMATION FOR SEQ ID NO:16:

```
    ( i ) SEQUENCE CHARACTERISTICS:
            ( A ) LENGTH: 8 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: direct repeat at -202 to - 195 of apoA-I
                    element D ( x i ) SEQUENCE DESCRIPTION: SEQ ID NO:16:
```

TGACCCCT                                                                                        8

( 2 ) INFORMATION FOR SEQ ID NO:17:

```
    ( i ) SEQUENCE CHARACTERISTICS:
            ( A ) LENGTH: 24 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: oligonucleotide of apoA-I promoter sequences
                    - 215 to -191

( x i ) SEQUENCE DESCRIPTION: SEQ ID NO:17:
```

CCCACTGAAC    CCTTGACCCC    TGCC                                                                 2 4

( 2 ) INFORMATION FOR SEQ ID NO:18:

```
    ( i ) SEQUENCE CHARACTERISTICS:
            ( A ) LENGTH: 37 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: oligonucleotide corresponding to alpha1AT1
                    - 130 to -93

( x i ) SEQUENCE DESCRIPTION: SEQ ID NO:18:
```

ATCCCAGCCA    GTGGACTTAG    CCCCTGTTTG    CTCCTCC                                                 3 7

( 2 ) INFORMATION FOR SEQ ID NO:19:

```
    ( i ) SEQUENCE CHARACTERISTICS:
            ( A ) LENGTH: 28 base pairs
            ( B ) TYPE: nucleic acid
            ( C ) STRANDEDNESS: both
            ( D ) TOPOLOGY: Not Relevant ( i i ) MOLECULE TYPE: DNA (genomic)
```

( v i i ) IMMEDIATE SOURCE:
        ( B ) CLONE: oligonucleotide corresponding to alpha1AT2
           - 131 to -103

( x i ) SEQUENCE DESCRIPTION: SEQ ID NO:19:

GATCCCAGCC AGTGGACTTA GCCCCTAG　　　　　　　　　　　　　　　　　　28

( 2 ) INFORMATION FOR SEQ ID NO:20:

( i ) SEQUENCE CHARACTERISTICS:
        ( A ) LENGTH: 29 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: apoCIIID oligonucleotide (-165 to -137)

( x i ) SEQUENCE DESCRIPTION: SEQ ID NO:20:

GTCCTAGGGA TTTCCCAACT CTCCCGCCC　　　　　　　　　　　　　　　　　29

( 2 ) INFORMATION FOR SEQ ID NO:21:

( i ) SEQUENCE CHARACTERISTICS:
        ( A ) LENGTH: 31 base pairs
        ( B ) TYPE: nucleic acid
        ( C ) STRANDEDNESS: both
        ( D ) TOPOLOGY: linear ( i i ) MOLECULE TYPE: DNA (genomic)

( v i i ) IMMEDIATE SOURCE:
        ( B ) CLONE: oligonucleotide corresponding to apoB
           sequences - 78 to -48

( x i ) SEQUENCE DESCRIPTION: SEQ ID NO:21:

GCCCTTTGGA CCTTTTGCAA TCCTGGCGCT C　　　　　　　　　　　　　　31

( 2 ) INFORMATION FOR SEQ ID NO:22:

( i ) SEQUENCE CHARACTERISTICS:
        ( A ) LENGTH: 40 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: OCT.BP oligonucleotide ( x i ) SEQUENCE DESCRIPTION: SEQ ID NO:22:

ATCCTCAACT TATTTTAGAA ATGCAAATTA CCCAGGTGGT　　　　　　　　　40

( 2 ) INFORMATION FOR SEQ ID NO:23:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: SP1 oligonuceotide ( x i ) SEQUENCE DESCRIPTION: SEQ ID NO:23:

GATACGCGTA TCGGGGCGGA GAAACACTGC　　　　　　　　　　　　　　　30

( 2 ) INFORMATION FOR SEQ ID NO:24:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: NFY oligonucleotide ( x i ) SEQUENCE DESCRIPTION: SEQ ID NO:24:

GGAACCAATG AAATGCGAGG        20

( 2 ) INFORMATION FOR SEQ ID NO:25:

( i ) SEQUENCE CHARACTERISTICS:
        ( A ) LENGTH: 34 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: NF1 oligonucleotide (-140 to -107)

( x i ) SEQUENCE DESCRIPTION: SEQ ID NO:25:

AGTCAAACAA TTTTTTGGCA AGAATATTAT GAAT        34

( 2 ) INFORMATION FOR SEQ ID NO:26:

( i ) SEQUENCE CHARACTERISTICS:
        ( A ) LENGTH: 26 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: oligonucleotide corresponding to albumin
            C/EBP site ( x i ) SEQUENCE DESCRIPTION: SEQ ID NO:26:

TGGTATGATT TTGTAATGGG GTAGGA        26

( 2 ) INFORMATION FOR SEQ ID NO:27:

( i ) SEQUENCE CHARACTERISTICS:
        ( A ) LENGTH: 23 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: oligonucleotide corresponding to TK C/EBP
            binding site ( x i ) SEQUENCE DESCRIPTION: SEQ ID NO:27:

GCGTCTTGTC ATTGGCGAAT TCG        23

( 2 ) INFORMATION FOR SEQ ID NO:28:

( i ) SEQUENCE CHARACTERISTICS:
        ( A ) LENGTH: 42 base pairs (B) TYPE: nucleic acid
(C) STRANDEDNESS: both
(D) TOPOLOGY: Not Relevant (i i) MOLECULE TYPE: DNA (genomic)

(v i i) IMMEDIATE SOURCE:
(B) CLONE: nonspecific oligonucleotide (x i) SEQUENCE DESCRIPTION: SEQ ID NO:28:

GGTGAATTCG AGCTCGGTAC CCGGGGATCC TCTAGAGTCG AC 42

(2) INFORMATION FOR SEQ ID NO:29:

(i) SEQUENCE CHARACTERISTICS:
(A) LENGTH: 36 base pairs
(B) TYPE: nucleic acid
(C) STRANDEDNESS: both
(D) TOPOLOGY: Not Relevant (i i) MOLECULE TYPE: DNA (genomic)

(v i i) IMMEDIATE SOURCE:
(B) CLONE: AI(WT) oligonucleotide (x i) SEQUENCE DESCRIPTION: SEQ ID NO:29:

GCTTGCTGTT TGCCCACTCT ATTTGCCCAG CCCCAG 36

(2) INFORMATION FOR SEQ ID NO:30:

(i) SEQUENCE CHARACTERISTICS:
(A) LENGTH: 36 base pairs
(B) TYPE: nucleic acid
(C) STRANDEDNESS: both
(D) TOPOLOGY: Not Relevant (i i) MOLECULE TYPE: DNA (genomic)

(v i i) IMMEDIATE SOURCE:
(B) CLONE: AICM1 oligonucleotide (x i) SEQUENCE DESCRIPTION: SEQ ID NO:30:

GAGGTAGGTT TGCCCACTCT ATTTGCCCAG CCCCAG 36

(2) INFORMATION FOR SEQ ID NO:31:

(i) SEQUENCE CHARACTERISTICS:
(A) LENGTH: 36 base pairs
(B) TYPE: nucleic acid
(C) STRANDEDNESS: both
(D) TOPOLOGY: Not Relevant (i i) MOLECULE TYPE: DNA (genomic)

(v i i) IMMEDIATE SOURCE:
(B) CLONE: AICM2 oligonucleotide (x i) SEQUENCE DESCRIPTION: SEQ ID NO:31:

GCTTGCGTGG GTCCCACTCT ATTTGCCCAG CCCCAG 36

(2) INFORMATION FOR SEQ ID NO:32:

(i) SEQUENCE CHARACTERISTICS:
(A) LENGTH: 36 base pairs
(B) TYPE: nucleic acid
(C) STRANDEDNESS: both
(D) TOPOLOGY: Not Relevant (i i) MOLECULE TYPE: DNA (genomic)

(v i i) IMMEDIATE SOURCE:
(B) CLONE: AICM3 oligonucleotide ( x i ) SEQUENCE DESCRIPTION: SEQ ID NO:32:

GCTTGCTGTT TGCAACAGAT ATTTGCCCAG CCCCAG 36

( 2 ) INFORMATION FOR SEQ ID NO:33:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AICM4 oligonucleotide ( x i ) SEQUENCE DESCRIPTION: SEQ ID NO:33:

GCTTGCTGTT TGCCCACTCG CGGGTCCAG CCCCAG 36

( 2 ) INFORMATION FOR SEQ ID NO:34:

( i ) SEQUENCE CHARACTERISTICS:
        ( A ) LENGTH: 36 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AICM5 oligonucleotide ( x i ) SEQUENCE DESCRIPTION: SEQ ID NO:34:

GCTTGCTGTT TGCCCACTCT ATTTGAAACT AACCAG 36

( 2 ) INFORMATION FOR SEQ ID NO:35:

( i ) SEQUENCE CHARACTERISTICS:
        ( A ) LENGTH: 37 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AIC oligonucleotide ( x i ) SEQUENCE DESCRIPTION: SEQ ID NO:35:

AGCTTGCTGT TTGCCCACTC TATTTGCCCA GCCCCAG 37

( 2 ) INFORMATION FOR SEQ ID NO:36:

( i ) SEQUENCE CHARACTERISTICS:
        ( A ) LENGTH: 32 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AID oligonucleotide ( x i ) SEQUENCE DESCRIPTION: SEQ ID NO:36:

GCCCCCACTG AAACCCTTGA CCCCTGCCCT GC 32

( 2 ) INFORMATION FOR SEQ ID NO:37:

( i ) SEQUENCE CHARACTERISTICS:
    ( A ) LENGTH: 19 base pairs
    ( B ) TYPE: nucleic acid
    ( C ) STRANDEDNESS: both
    ( D ) TOPOLOGY: Not Relevant ( i i ) MOLECULE TYPE: DNA (genomic)

( v i i ) IMMEDIATE SOURCE:
    ( B ) CLONE: AIIH oligonucleotide ( x i ) SEQUENCE DESCRIPTION: SEQ ID NO:37:

TCTCATTACA CATTAACTC　　　　　　　　　　　　　　　　　　　19

( 2 ) INFORMATION FOR SEQ ID NO:38:

( i ) SEQUENCE CHARACTERISTICS:
    ( A ) LENGTH: 25 base pairs
    ( B ) TYPE: nucleic acid
    ( C ) STRANDEDNESS: both
    ( D ) TOPOLOGY: Not Relevant ( i i ) MOLECULE TYPE: DNA (genomic)

( v i i ) IMMEDIATE SOURCE:
    ( B ) CLONE: AIIN oligonucleotide ( x i ) SEQUENCE DESCRIPTION: SEQ ID NO:38:

TATCTATTTA ACTGATTTCA CCCAA　　　　　　　　　　　　　　25

( 2 ) INFORMATION FOR SEQ ID NO:39:

( i ) SEQUENCE CHARACTERISTICS:
    ( A ) LENGTH: 26 base pairs
    ( B ) TYPE: nucleic acid
    ( C ) STRANDEDNESS: both
    ( D ) TOPOLOGY: Not Relevant ( i i ) MOLECULE TYPE: DNA (genomic)

( v i i ) IMMEDIATE SOURCE:
    ( B ) CLONE: CIIIB oligonucleotide ( x i ) SEQUENCE DESCRIPTION: SEQ ID NO:39:

GGTCAGCAGG TGACCTTTGC CCAGCG　　　　　　　　　　　　26

( 2 ) INFORMATION FOR SEQ ID NO:40:

( i ) SEQUENCE CHARACTERISTICS:
    ( A ) LENGTH: 22 base pairs
    ( B ) TYPE: nucleic acid
    ( C ) STRANDEDNESS: both
    ( D ) TOPOLOGY: Not Relevant ( i i ) MOLECULE TYPE: DNA (genomic)

( v i i ) IMMEDIATE SOURCE:
    ( B ) CLONE: CIIIC oligonucleotide ( x i ) SEQUENCE DESCRIPTION: SEQ ID NO:40:

CCGCTTGCTG CATCTCTGGA CA　　　　　　　　　　　　　　　22

( 2 ) INFORMATION FOR SEQ ID NO:41:

( i ) SEQUENCE CHARACTERISTICS:
    ( A ) LENGTH: 27 base pairs
    ( B ) TYPE: nucleic acid
    ( C ) STRANDEDNESS: both
    ( D ) TOPOLOGY: Not Relevant ( i i ) MOLECULE TYPE: DNA (genomic)

(vii) IMMEDIATE SOURCE:
  (B) CLONE: BA1 oligonucleotide (xi) SEQUENCE DESCRIPTION: SEQ ID NO:41:

CCCGGGAGGC GCCCTTTGGA GCTTTTG  27

(2) INFORMATION FOR SEQ ID NO:42:

(i) SEQUENCE CHARACTERISTICS:
    (A) LENGTH: 26 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: BA2 oligonucleotide (xi) SEQUENCE DESCRIPTION: SEQ ID NO:42:

CAATCCTGGC GCTCTTGCAG CCTGGG  26

(2) INFORMATION FOR SEQ ID NO:43:

(i) SEQUENCE CHARACTERISTICS:
    (A) LENGTH: 30 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: BA3 oligonucleotide (xi) SEQUENCE DESCRIPTION: SEQ ID NO:43:

GCCCTTTGGA CCTTTTGCAA TCCTGGCGCT  30

(2) INFORMATION FOR SEQ ID NO:44:

(i) SEQUENCE CHARACTERISTICS:
    (A) LENGTH: 19 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: BC1 oligonucleotide (xi) SEQUENCE DESCRIPTION: SEQ ID NO:44:

GCCAGTGTAG AAAAGCAAA  19

(2) INFORMATION FOR SEQ ID NO:45:

(i) SEQUENCE CHARACTERISTICS:
    (A) LENGTH: 21 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: HNF1/LFB1 oligonucleotide (xi) SEQUENCE DESCRIPTION: SEQ ID NO:45:

AGTATGGTTA ATGATCTACA G  21

(2) INFORMATION FOR SEQ ID NO:46:

(i) SEQUENCE CHARACTERISTICS:
    (A) LENGTH: 24 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: NF1 oligonucleotide (-133 to -110)

(xi) SEQUENCE DESCRIPTION: SEQ ID NO:46:

ACAATTTTTT GGCAAGAATA TTAT                                  24

(2) INFORMATION FOR SEQ ID NO:47:

(i) SEQUENCE CHARACTERISTICS:
    (A) LENGTH: 26 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: AlbD oligonucleotide (xi) SEQUENCE DESCRIPTION: SEQ ID NO:47:

TGGTATGATT TTGTAATGGG GTAGGA                                26

(2) INFORMATION FOR SEQ ID NO:48:

(i) SEQUENCE CHARACTERISTICS:
    (A) LENGTH: 32 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: AP1 oligonucleotide (xi) SEQUENCE DESCRIPTION: SEQ ID NO:48:

AGCCGCAAGT GACTCAGCGC GGGGCGTGTG CA                         32

(2) INFORMATION FOR SEQ ID NO:49:

(i) SEQUENCE CHARACTERISTICS:
    (A) LENGTH: 32 base pairs
    (B) TYPE: nucleic acid
    (C) STRANDEDNESS: both
    (D) TOPOLOGY: Not Relevant (ii) MOLECULE TYPE: DNA (genomic)

(vii) IMMEDIATE SOURCE:
    (B) CLONE: AP2/3 oligonucleotide (xi) SEQUENCE DESCRIPTION: SEQ ID NO:49:

GTTAGGGTGT GGAAAGTCCC CAGGCTCCCC AG                         32

(2) INFORMATION FOR SEQ ID NO:50:

(i) SEQUENCE CHARACTERISTICS:
    (A) LENGTH: 26 base pairs
    (B) TYPE: nucleic acid
    (C) STRANDEDNESS: both
    (D) TOPOLOGY: Not Relevant (i i) MOLECULE TYPE: DNA (genomic)

(v i i) IMMEDIATE SOURCE:
    (B) CLONE: OTF oligonucleotide (x i) SEQUENCE DESCRIPTION: SEQ ID NO:50:

TTCCCAATGA TTTGCATGCT CTCACT      26

(2) INFORMATION FOR SEQ ID NO:51:

(i) SEQUENCE CHARACTERISTICS:
        (A) LENGTH: 36 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: AIIAB oligonucleotide (x i) SEQUENCE DESCRIPTION: SEQ ID NO:51:

AGTCCTGTCA CCTGACAGGG GGTGGGTAAA CAGACA      36

(2) INFORMATION FOR SEQ ID NO:52:

(i) SEQUENCE CHARACTERISTICS:
        (A) LENGTH: 40 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: AIIBM1 oligonucleotide (x i) SEQUENCE DESCRIPTION: SEQ ID NO:52:

CCATAGTCCT TATCTATGAT AGTCGGTGGG TAAACACACA      40

(2) INFORMATION FOR SEQ ID NO:53:

(i) SEQUENCE CHARACTERISTICS:
        (A) LENGTH: 21 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: AIIC oligonucleotide (x i) SEQUENCE DESCRIPTION: SEQ ID NO:53:

CTCCCCCATT TCTCCAACTT G      21

(2) INFORMATION FOR SEQ ID NO:54:

(i) SEQUENCE CHARACTERISTICS:
        (A) LENGTH: 26 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: AIID oligonucleotide (x i) SEQUENCE DESCRIPTION: SEQ ID NO:54:

TGCTTCCTGT TGCATTCAAG TCCAAG      26

( 2 ) INFORMATION FOR SEQ ID NO:55:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AIIE oligonucleotide ( x i ) SEQUENCE DESCRIPTION: SEQ ID NO:55:

ATAATGGAAT AAAGACAC                              18

( 2 ) INFORMATION FOR SEQ ID NO:56:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: unknown ( i i ) MOLECULE TYPE: DNA (genomic)

( v i i ) IMMEDIATE SOURCE:
        ( B ) CLONE: AIIF oligonucleotide ( x i ) SEQUENCE DESCRIPTION: SEQ ID NO:56:

GATAAGGTTG AGAGATGAGA TCTAC                       25

( 2 ) INFORMATION FOR SEQ ID NO:57:

( i ) SEQUENCE CHARACTERISTICS:
        ( A ) LENGTH: 18 base pairs
        ( B ) TYPE: nucleic acid
        ( C ) STRANDEDNESS: both
        ( D ) TOPOLOGY: unknown ( i i ) MOLECULE TYPE: DNA (genomic)

( v i i ) IMMEDIATE SOURCE:
        ( B ) CLONE: AIIG oligonucleotide ( x i ) SEQUENCE DESCRIPTION: SEQ ID NO:57:

GATTTCAATT CCTTTCTC                              18

( 2 ) INFORMATION FOR SEQ ID NO:58:

( i ) SEQUENCE CHARACTERISTICS:
        ( A ) LENGTH: 20 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AIIH oligonucleotide ( x i ) SEQUENCE DESCRIPTION: SEQ ID NO:58:

GTCTCATTAC ACATTAACTC                           20

( 2 ) INFORMATION FOR SEQ ID NO:59:

( i ) SEQUENCE CHARACTERISTICS:
        ( A ) LENGTH: 26 base pairs
        ( B ) TYPE: nucleic acid
        ( C ) STRANDEDNESS: both (D) TOPOLOGY: Not Relevant (i i) MOLECULE TYPE: DNA (genomic)

(v i i) IMMEDIATE SOURCE:
   (B) CLONE: AIII oligonucleotide (x i) SEQUENCE DESCRIPTION: SEQ ID NO:59:

ATTCACCTCT TTTCCTGCCA GAGCCC 26

(2) INFORMATION FOR SEQ ID NO:60:

(i) SEQUENCE CHARACTERISTICS:
      (A) LENGTH: 24 base pairs
      (B) TYPE: nucleic acid
      (C) STRANDEDNESS: both
      (D) TOPOLOGY: Not Relevant (i i) MOLECULE TYPE: DNA (genomic)

(v i i) IMMEDIATE SOURCE:
      (B) CLONE: AIIJ oligonucleotide (x i) SEQUENCE DESCRIPTION: SEQ ID NO:60:

TGCCTTCAAC CTTTACCCTG GTAG 24

(2) INFORMATION FOR SEQ ID NO:61:

(i) SEQUENCE CHARACTERISTICS:
      (A) LENGTH: 18 base pairs
      (B) TYPE: nucleic acid
      (C) STRANDEDNESS: double
      (D) TOPOLOGY: Not Relevant (i i) MOLECULE TYPE: DNA (genomic)

(v i i) IMMEDIATE SOURCE:
      (B) CLONE: AIIK oligonucleotide (x i) SEQUENCE DESCRIPTION: SEQ ID NO:61:

TAAGGTGATC AAATGACC 18

(2) INFORMATION FOR SEQ ID NO:62:

(i) SEQUENCE CHARACTERISTICS:
      (A) LENGTH: 34 base pairs
      (B) TYPE: nucleic acid
      (C) STRANDEDNESS: double
      (D) TOPOLOGY: Not Relevant (i i) MOLECULE TYPE: DNA (genomic)

(v i i) IMMEDIATE SOURCE:
      (B) CLONE: AIIKM1 oligonucleotide (x i) SEQUENCE DESCRIPTION: SEQ ID NO:62:

GCCTAGAACT GATATCTCGA TCAAAATACC AGGT 34

(2) INFORMATION FOR SEQ ID NO:63:

(i) SEQUENCE CHARACTERISTICS:
      (A) LENGTH: 38 base pairs
      (B) TYPE: nucleic acid
      (C) STRANDEDNESS: both
      (D) TOPOLOGY: Not Relevant (i i) MOLECULE TYPE: DNA (genomic)

(v i i) IMMEDIATE SOURCE:
      (B) CLONE: AIIL oligonucleotide (x i) SEQUENCE DESCRIPTION: SEQ ID NO:63:

GGCTATTGCC CCTGCTGACT CAATATTGGC TAATCACT 38

( 2 ) INFORMATION FOR SEQ ID NO:64:

( i ) SEQUENCE CHARACTERISTICS:
        ( A ) LENGTH: 39 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AIILM1 oligonucleotide ( x i ) SEQUENCE DESCRIPTION: SEQ ID NO:64:

GGCTATTGCC CCTGCTGACT CAATATATGG CTAATCACT 39

( 2 ) INFORMATION FOR SEQ ID NO:65:

( i ) SEQUENCE CHARACTERISTICS:
        ( A ) LENGTH: 38 base pairs
        ( B ) TYPE: nucleic acid
        ( C ) STRANDEDNESS: double
        ( D ) TOPOLOGY: Not Relevant ( i i ) MOLECULE TYPE: DNA (genomic)

( v i i ) IMMEDIATE SOURCE:
        ( B ) CLONE: AIILM2 oligonucleotide ( x i ) SEQUENCE DESCRIPTION: SEQ ID NO:65:

GGCTATTGCC CCTGCTCAGT CAATATTGGC TAATCACT 38

( 2 ) INFORMATION FOR SEQ ID NO:66:

( i ) SEQUENCE CHARACTERISTICS:
        ( A ) LENGTH: 30 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: AIIM oligonucleotide ( x i ) SEQUENCE DESCRIPTION: SEQ ID NO:66:

ACCTCTCCCC CTCCCCCACC CCCAACAGGA 30

( 2 ) INFORMATION FOR SEQ ID NO:67:

( i ) SEQUENCE CHARACTERISTICS:
        ( A ) LENGTH: 53 base pairs
        ( B ) TYPE: nucleic acid
        ( C ) STRANDEDNESS: both
        ( D ) TOPOLOGY: Not Relevant ( i i ) MOLECULE TYPE: DNA (genomic)

( v i i ) IMMEDIATE SOURCE:
        ( B ) CLONE: BA oligonucleotide ( x i ) SEQUENCE DESCRIPTION: SEQ ID NO:67:

CCCGGGAGGC GCCCTTTGGA CCTTTTGCAA TCCTGGCGCT CTTGCAGCCT GGG 53

( 2 ) INFORMATION FOR SEQ ID NO:68:

( i ) SEQUENCE CHARACTERISTICS:
        ( A ) LENGTH: 18 base pairs ( B ) TYPE: nucleic acid
( C ) STRANDEDNESS: both
( D ) TOPOLOGY: Not Relevant ( i i ) MOLECULE TYPE: DNA (genomic)

( v i i ) IMMEDIATE SOURCE:
( B ) CLONE: BA4 oligonucleotide ( x i ) SEQUENCE DESCRIPTION: SEQ ID NO:68:

TGGACCTTTT GCAATCCT 18

( 2 ) INFORMATION FOR SEQ ID NO:69:

( i ) SEQUENCE CHARACTERISTICS:
( A ) LENGTH: 24 base pairs
( B ) TYPE: nucleic acid
( C ) STRANDEDNESS: both
( D ) TOPOLOGY: Not Relevant ( i i ) MOLECULE TYPE: DNA (genomic)

( v i i ) IMMEDIATE SOURCE:
( B ) CLONE: BE oligonucleotide ( x i ) SEQUENCE DESCRIPTION: SEQ ID NO:69:

CTTCTCGGTT GCTGCCGCTG AGGA 24

( 2 ) INFORMATION FOR SEQ ID NO:70:

( i ) SEQUENCE CHARACTERISTICS:
( A ) LENGTH: 29 base pairs
( B ) TYPE: nucleic acid
( C ) STRANDEDNESS: both
( D ) TOPOLOGY: Not Relevant ( i i ) MOLECULE TYPE: DNA (genomic)

( v i i ) IMMEDIATE SOURCE:
( B ) CLONE: BCB oligonucleotide ( x i ) SEQUENCE DESCRIPTION: SEQ ID NO:70:

CCAGTGTAGA AAGCAAACAG GTCAGGCCC 29

( 2 ) INFORMATION FOR SEQ ID NO:71:

( i ) SEQUENCE CHARACTERISTICS:
( A ) LENGTH: 30 base pairs
( B ) TYPE: nucleic acid
( C ) STRANDEDNESS: both
( D ) TOPOLOGY: Not Relevant ( i i ) MOLECULE TYPE: DNA (genomic)

( v i i ) IMMEDIATE SOURCE:
( B ) CLONE: LM1 oligonucleotide ( x i ) SEQUENCE DESCRIPTION: SEQ ID NO:71:

GATATCTAGA AAAGCAAACA GGTCAGGCCC 30

( 2 ) INFORMATION FOR SEQ ID NO:72:

( i ) SEQUENCE CHARACTERISTICS:
( A ) LENGTH: 30 base pairs
( B ) TYPE: nucleic acid
( C ) STRANDEDNESS: both
( D ) TOPOLOGY: Not Relevant ( i i ) MOLECULE TYPE: DNA (genomic)

( v i i ) IMMEDIATE SOURCE:
( B ) CLONE: LM2 oligonucleotide (x i) SEQUENCE DESCRIPTION: SEQ ID NO:72:

CCAGTGTAGA GATATCAACA GGTCAGGCCC         30

(2) INFORMATION FOR SEQ ID NO:73:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: LM3 oligonucleotide (x i) SEQUENCE DESCRIPTION: SEQ ID NO:73:

CCAGTGTAGA AAAGCAAACG ATATCGGCCC         30

(2) INFORMATION FOR SEQ ID NO:74:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: LM4 oligonucleotide (x i) SEQUENCE DESCRIPTION: SEQ ID NO:74:

CCAGTGTAGA AAATACCCCA GGTCAGGCCC         30

(2) INFORMATION FOR SEQ ID NO:75:

(i) SEQUENCE CHARACTERISTICS:
        (A) LENGTH: 30 base pairs
        (B) TYPE: nucleic acid
        (C) STRANDEDNESS: double
        (D) TOPOLOGY: Not Relevant (i i) MOLECULE TYPE: DNA (genomic)

(v i i) IMMEDIATE SOURCE:
        (B) CLONE: LM5 oligonucleotide (x i) SEQUENCE DESCRIPTION: SEQ ID NO:75:

CCAGTGTAGA AAAGCAAAAC TTGACTTCCC         30

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (i i) MOLECULE TYPE: DNA (genomic)

(v i i) IMMEDIATE SOURCE:
        (B) CLONE: LM6 oligonucleotide (x i) SEQUENCE DESCRIPTION: SEQ ID NO:76:

CCAGTGTAGA AAATAAAACA GGTCAGGCCC         30

(2) INFORMATION FOR SEQ ID NO:77:

( i ) SEQUENCE CHARACTERISTICS:
            ( A ) LENGTH: 30 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: LM7 oligonucleotide ( x i ) SEQUENCE DESCRIPTION: SEQ ID NO:77:

CCAGTGTAGA AAAGCCCACA GGTCAGGCCC                               30

( 2 ) INFORMATION FOR SEQ ID NO:78:

( i ) SEQUENCE CHARACTERISTICS:
            ( A ) LENGTH: 28 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: LM8 oligonucleotide ( x i ) SEQUENCE DESCRIPTION: SEQ ID NO:78:

CCAGTAGAAA AGCAACAAGG TCAGGCCC                                 28

( 2 ) INFORMATION FOR SEQ ID NO:79:

( i ) SEQUENCE CHARACTERISTICS:
            ( A ) LENGTH: 30 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: LM9 oligonuicleotide ( x i ) SEQUENCE DESCRIPTION: SEQ ID NO:79:

CCAGTGTAGA AAAGCAAACC TCTGAGGCCC                               30

( 2 ) INFORMATION FOR SEQ ID NO:80:

( i ) SEQUENCE CHARACTERISTICS:
            ( A ) LENGTH: 30 base pairs
            ( B ) TYPE: nucleic acid
            ( C ) STRANDEDNESS: both
            ( D ) TOPOLOGY: Not Relevant ( i i ) MOLECULE TYPE: DNA (genomic)

( v i i ) IMMEDIATE SOURCE:
            ( B ) CLONE: LM10 oligonucleotide ( x i ) SEQUENCE DESCRIPTION: SEQ ID NO:80:

CCAGTGTAGA AAAGCAAACA GTGCAGGCCC                               30

( 2 ) INFORMATION FOR SEQ ID NO:81:

( i ) SEQUENCE CHARACTERISTICS:
            ( A ) LENGTH: 30 base pairs
            ( B ) TYPE: nucleic acid
            ( C ) STRANDEDNESS: double
            ( D ) TOPOLOGY: Not Relevant ( i i ) MOLECULE TYPE: DNA (genomic)

(vii) IMMEDIATE SOURCE:
    (B) CLONE: LM11 oligonucleotide (xi) SEQUENCE DESCRIPTION: SEQ ID NO:81:

CCAGTGTAGA AAAGCAAACA GGTACGGCCC  30

(2) INFORMATION FOR SEQ ID NO:82:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: LM12 oligonucleotide (xi) SEQUENCE DESCRIPTION: SEQ ID NO:82:

CCAGTGTAGA AAAGCAAACA GGTCATTCCC  30

(2) INFORMATION FOR SEQ ID NO:83:

(i) SEQUENCE CHARACTERISTICS:
        (A) LENGTH: 30 base pairs
        (B) TYPE: nucleic acid
        (C) STRANDEDNESS: double
        (D) TOPOLOGY: Not Relevant (ii) MOLECULE TYPE: DNA (genomic)

(vii) IMMEDIATE SOURCE:
        (B) CLONE: LM13 oligonucleotide (xi) SEQUENCE DESCRIPTION: SEQ ID NO:83:

CCAGTGTAGA CAGTTAAATA GATCAGGCCC  30

(2) INFORMATION FOR SEQ ID NO:84:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: LM14 oligonucleotide (xi) SEQUENCE DESCRIPTION: SEQ ID NO:84:

CCAGTGTAGA CACGCAAACA GGTCAGGCCC  30

(2) INFORMATION FOR SEQ ID NO:85:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: LM15 oligonucleotide (xi) SEQUENCE DESCRIPTION: SEQ ID NO:85:

CCAGTGTAGC ACAGCAAACA GGTCAGGCCC  30

(2) INFORMATION FOR SEQ ID NO:86:

(i) SEQUENCE CHARACTERISTICS:
       (A) LENGTH: 30 base pairs
       (B) TYPE: nucleic acid
       (C) STRANDEDNESS: both
       (D) TOPOLOGY: Not Relevant (ii) MOLECULE TYPE: DNA (genomic)

(vii) IMMEDIATE SOURCE:
       (B) CLONE: LM16 oligonucleotide (xi) SEQUENCE DESCRIPTION: SEQ ID NO:86:

CCAGTGTCTA AAAGCAAACA GGTCAGGCCC                                                                  30

(2) INFORMATION FOR SEQ ID NO:87:

(i) SEQUENCE CHARACTERISTICS:
       (A) LENGTH: 30 base pairs
       (B) TYPE: nucleic acid
       (C) STRANDEDNESS: both
       (D) TOPOLOGY: Not Relevant (ii) MOLECULE TYPE: DNA (genomic)

(vii) IMMEDIATE SOURCE:
       (B) CLONE: LM17 oligonucleotide (xi) SEQUENCE DESCRIPTION: SEQ ID NO:87:

CCAGTTGAGA AAAGCAAACA GGTCAGGCCC                                                                  30

(2) INFORMATION FOR SEQ ID NO:88:

(i) SEQUENCE CHARACTERISTICS:
       (A) LENGTH: 26 base pairs
       (B) TYPE: nucleic acid
       (C) STRANDEDNESS: double
       (D) TOPOLOGY: Not Relevant (ii) MOLECULE TYPE: DNA (genomic)

(vii) IMMEDIATE SOURCE:
       (B) CLONE: CIIBM1 oligonucleotide (xi) SEQUENCE DESCRIPTION: SEQ ID NO:88:

GGTCAGATAT CGACCTTTGC CCAGCG                                                                      26

(2) INFORMATION FOR SEQ ID NO:89:

(i) SEQUENCE CHARACTERISTICS:
       (A) LENGTH: 26 base pairs
       (B) TYPE: nucleic acid
       (C) STRANDEDNESS: both
       (D) TOPOLOGY: Not Relevant (ii) MOLECULE TYPE: DNA (genomic)

(vii) IMMEDIATE SOURCE:
       (B) CLONE: CIIIBM2 oligonucleotide (xi) SEQUENCE DESCRIPTION: SEQ ID NO:89:

GGTCAGCAGG ATATCTTTGC CCAGCG                                                                      26

(2) INFORMATION FOR SEQ ID NO:90:

(i) SEQUENCE CHARACTERISTICS:
       (A) LENGTH: 20 base pairs
       (B) TYPE: nucleic acid
       (C) STRANDEDNESS: both
       (D) TOPOLOGY: Not Relevant ( i i ) MOLECULE TYPE: DNA (genomic)

( v i i ) IMMEDIATE SOURCE:
   ( B ) CLONE: CIIIBM5 oligonucleotide ( x i ) SEQUENCE DESCRIPTION: SEQ ID NO:90:

GGTCAGCAGG TGACGACAGA                     20

( 2 ) INFORMATION FOR SEQ ID NO:91:

( i ) SEQUENCE CHARACTERISTICS:
   ( A ) LENGTH: 8 base pairs
   ( B ) TYPE: nucleic acid
   ( C ) STRANDEDNESS: both
   ( D ) TOPOLOGY: Not Relevant ( i i ) MOLECULE TYPE: DNA (genomic)

( v i i ) IMMEDIATE SOURCE:
   ( B ) CLONE: octameric motif ( x i ) SEQUENCE DESCRIPTION: SEQ ID NO:91:

CAGGTGAC                             8

( 2 ) INFORMATION FOR SEQ ID NO:92:

( i ) SEQUENCE CHARACTERISTICS:
   ( A ) LENGTH: 20 base pairs
   ( B ) TYPE: nucleic acid
   ( C ) STRANDEDNESS: both
   ( D ) TOPOLOGY: Not Relevant ( i i ) MOLECULE TYPE: DNA (genomic)

( v i i ) IMMEDIATE SOURCE:
   ( B ) CLONE: polylinker region unsed in constructing
     plasmids ( x i ) SEQUENCE DESCRIPTION: SEQ ID NO:92:

CCGCGGACTC GAGTGCCGGC                     20

( 2 ) INFORMATION FOR SEQ ID NO:93:

( i ) SEQUENCE CHARACTERISTICS:
   ( A ) LENGTH: 42 base pairs
   ( B ) TYPE: nucleic acid
   ( C ) STRANDEDNESS: both
   ( D ) TOPOLOGY: Not Relevant ( i i ) MOLECULE TYPE: DNA (genomic)

( v i i ) IMMEDIATE SOURCE:
   ( B ) CLONE: primer PCR-LM5

( x i ) SEQUENCE DESCRIPTION: SEQ ID NO:93:

AGGGCGCCTC CCGGGAAGTC AAGTTTTGCT TTTCTACACT GG        42

( 2 ) INFORMATION FOR SEQ ID NO:94:

( i ) SEQUENCE CHARACTERISTICS:
   ( A ) LENGTH: 26 base pairs
   ( B ) TYPE: nucleic acid
   ( C ) STRANDEDNESS: both
   ( D ) TOPOLOGY: Not Relevant ( i i ) MOLECULE TYPE: DNA (genomic)

( v i i ) IMMEDIATE SOURCE:
   ( B ) CLONE: primer rev-5-26

( x i ) SEQUENCE DESCRIPTION: SEQ ID NO:94:

TCACACAGGA AACAGCTATG ACCATG 26

(2) INFORMATION FOR SEQ ID NO:95:

(i) SEQUENCE CHARACTERISTICS:
        (A) LENGTH: 42 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: primer PCR-LM5c (xi) SEQUENCE DESCRIPTION: SEQ ID NO:95:

CCAGTGTAGA AAAGCAAAAC TTGACTTCCC GGGAGGCGCC CT 42

(2) INFORMATION FOR SEQ ID NO:96:

(i) SEQUENCE CHARACTERISTICS:
        (A) LENGTH: 26 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: primer PCR-B8R (xi) SEQUENCE DESCRIPTION: SEQ ID NO:96:

GGTGGGAATG CGCGGCCGGC GCCCGC 26

(2) INFORMATION FOR SEQ ID NO:97:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: primer PCR-LM6

(xi) SEQUENCE DESCRIPTION: SEQ ID NO:97:

CCAGTGTAGA AAATAAAACA GGTCAGGCCC 30

(2) INFORMATION FOR SEQ ID NO:98:

(i) SEQUENCE CHARACTERISTICS:
        (A) LENGTH: 30 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: primer PCR-LM6c (xi) SEQUENCE DESCRIPTION: SEQ ID NO:98:

GGGCCTGACC TGTTTTATTT TCTACACTGG 30

(2) INFORMATION FOR SEQ ID NO:99:

(i) SEQUENCE CHARACTERISTICS:
        (A) LENGTH: 31 base pairs
        (B) TYPE: nucleic acid ( C ) STRANDEDNESS: single
( D ) TOPOLOGY: Not Relevant ( i i ) MOLECULE TYPE: DNA (genomic)

( v i i ) IMMEDIATE SOURCE:
( B ) CLONE: top strand of double stranded cloning
oligonucleotide ( x i ) SEQUENCE DESCRIPTION: SEQ ID NO:99:

AATTCGGTAC CGCCGGCCGC GCATTCCCAC C  31

( 2 ) INFORMATION FOR SEQ ID NO:100:

( i ) SEQUENCE CHARACTERISTICS:
( A ) LENGTH: 27 base pairs
( B ) TYPE: nucleic acid
( C ) STRANDEDNESS: single
( D ) TOPOLOGY: Not Relevant ( i i ) MOLECULE TYPE: DNA (genomic)

( v i i ) IMMEDIATE SOURCE:
( B ) CLONE: bottom strand of double stranded cloning
oligonucleotide ( x i ) SEQUENCE DESCRIPTION: SEQ ID NO:100:

GCCATGGCGG CCGGCGCGTA AGGGTGG  27

( 2 ) INFORMATION FOR SEQ ID NO:101:

( i ) SEQUENCE CHARACTERISTICS:
( A ) LENGTH: 18 base pairs
( B ) TYPE: nucleic acid
( C ) STRANDEDNESS: single
( D ) TOPOLOGY: Not Relevant ( i i ) MOLECULE TYPE: DNA (genomic)

( v i i ) IMMEDIATE SOURCE:
( B ) CLONE: top strand of affinity chromatography
oligonucleotide ( x i ) SEQUENCE DESCRIPTION: SEQ ID NO:101:

TTGCGCCCTT TGGACCTT  18

( 2 ) INFORMATION FOR SEQ ID NO:102:

( i ) SEQUENCE CHARACTERISTICS:
( A ) LENGTH: 18 base pairs
( B ) TYPE: nucleic acid
( C ) STRANDEDNESS: single
( D ) TOPOLOGY: Not Relevant ( i i ) MOLECULE TYPE: DNA (genomic)

( v i i ) IMMEDIATE SOURCE:
( B ) CLONE: bottom strand of affinity chromatography
oligonucleotide ( x i ) SEQUENCE DESCRIPTION: SEQ ID NO:102:

GCGGGAAACC TGCAAAAC  18

( 2 ) INFORMATION FOR SEQ ID NO:103:

( i ) SEQUENCE CHARACTERISTICS:
( A ) LENGTH: 49 base pairs
( B ) TYPE: nucleic acid
( C ) STRANDEDNESS: both
( D ) TOPOLOGY: Not Relevant ( i i ) MOLECULE TYPE: DNA (genomic)

( v i i ) IMMEDIATE SOURCE:
  ( B ) CLONE: oligonucleotide PCR264AI ( x i ) SEQUENCE DESCRIPTION: SEQ ID NO:103:

GATATCGGTA CCGACCCCAC CCGGGAGACC TGCAAGCCTG CAGACACTC  49

( 2 ) INFORMATION FOR SEQ ID NO:104:

( i ) SEQUENCE CHARACTERISTICS:
  ( A ) LENGTH: 34 base pairs
  ( B ) TYPE: nucleic acid
  ( C ) STRANDEDNESS: both
  ( D ) TOPOLOGY: Not Relevant ( i i ) MOLECULE TYPE: DNA (genomic)

( v i i ) IMMEDIATE SOURCE:
  ( B ) CLONE: oligonucleotide OL-AI- 1c ( x i ) SEQUENCE DESCRIPTION: SEQ ID NO:104:

ATTTAAAATA TTGTGTGTAA GCAGCCAGCT CTTG  34

( 2 ) INFORMATION FOR SEQ ID NO:105:

( i ) SEQUENCE CHARACTERISTICS:
  ( A ) LENGTH: 37 base pairs
  ( B ) TYPE: nucleic acid
  ( C ) STRANDEDNESS: both
  ( D ) TOPOLOGY: Not Relevant ( i i ) MOLECULE TYPE: DNA (genomic)

( v i i ) IMMEDIATE SOURCE:
  ( B ) CLONE: oligonucleotide PCRAII3

( x i ) SEQUENCE DESCRIPTION: SEQ ID NO:105:

CCATGGATCC CTGAACATAC CCTACCCCCA GTAAAAC  37

( 2 ) INFORMATION FOR SEQ ID NO:106:

( i ) SEQUENCE CHARACTERISTICS:
  ( A ) LENGTH: 18 base pairs
  ( B ) TYPE: nucleic acid
  ( C ) STRANDEDNESS: both
  ( D ) TOPOLOGY: Not Relevant ( i i ) MOLECULE TYPE: DNA (genomic)

( v i i ) IMMEDIATE SOURCE:
  ( B ) CLONE: oligonucleotide corresponding to apoB -80 to
       - 63

( x i ) SEQUENCE DESCRIPTION: SEQ ID NO:106:

GCGCCCTTTG GACCTTTT  18

( 2 ) INFORMATION FOR SEQ ID NO:107:

( i ) SEQUENCE CHARACTERISTICS:
  ( A ) LENGTH: 39 base pairs
  ( B ) TYPE: nucleic acid
  ( C ) STRANDEDNESS: single
  ( D ) TOPOLOGY: Not Relevant ( i i ) MOLECULE TYPE: DNA (genomic)

( v i i ) IMMEDIATE SOURCE:
  ( B ) CLONE: top strand of apoCIII -90 to -73
       oligonucleotide ( x i ) SEQUENCE DESCRIPTION: SEQ ID NO:107:

AGGTCAGCAG GTGACGACAG ATCAGCAGGT GACGACAGA                          39

(2) INFORMATION FOR SEQ ID NO:108:

(i) SEQUENCE CHARACTERISTICS:
        (A) LENGTH: 39 base pairs
        (B) TYPE: nucleic acid
        (C) STRANDEDNESS: single
        (D) TOPOLOGY: Not Relevant (ii) MOLECULE TYPE: DNA (genomic)

(vii) IMMEDIATE SOURCE:
        (B) CLONE: bottom strand of apoCIII - 90 to -73
            oligonucleotide (xi) SEQUENCE DESCRIPTION: SEQ ID NO:108:

AGTCGTCCAC TGCTGTCTAG TCGTCCACTG CTGTCTTCC                          39

(2) INFORMATION FOR SEQ ID NO:109:

(i) SEQUENCE CHARACTERISTICS:
        (A) LENGTH: 55 base pairs
        (B) TYPE: nucleic acid
        (C) STRANDEDNESS: both
        (D) TOPOLOGY: Not Relevant (ii) MOLECULE TYPE: DNA (genomic)

(vii) IMMEDIATE SOURCE:
        (B) CLONE: primer with strong translation initiation
            sequence (xi) SEQUENCE DESCRIPTION: SEQ ID NO:109:

GACGCAGAAT TCAAGCTTGC CGCCGCCATG GCAATGGTAG TTAGCAGCTG GCGAG         55

(2) INFORMATION FOR SEQ ID NO:110:

(i) SEQUENCE CHARACTERISTICS:
        (A) LENGTH: 43 base pairs
        (B) TYPE: nucleic acid
        (C) STRANDEDNESS: single
        (D) TOPOLOGY: Not Relevant (ii) MOLECULE TYPE: DNA (genomic)

(vii) IMMEDIATE SOURCE:
        (B) CLONE: forward primer used to clone rat HNF4 by PCR (xi) SEQUENCE DESCRIPTION: SEQ ID NO:110:

GACAGAATTC GCCGCCGCCA TGGACATGGC TGACTACAGT GCT                     43

(2) INFORMATION FOR SEQ ID NO:111:

(i) SEQUENCE CHARACTERISTICS:
        (A) LENGTH: 45 base pairs
        (B) TYPE: nucleic acid
        (C) STRANDEDNESS: single
        (D) TOPOLOGY: Not Relevant (ii) MOLECULE TYPE: DNA (genomic)

(vii) IMMEDIATE SOURCE:
        (B) CLONE: reverse primer used to clone rat HNF4 by PCR (xi) SEQUENCE DESCRIPTION: SEQ ID NO:111:

GACAGAATTC AAGCTTTCTC TGAGGGTGGG AGCCAGCAGA AGCCT                   45

(2) INFORMATION FOR SEQ ID NO:112:

(i) SEQUENCE CHARACTERISTICS:

(A) LENGTH: 17 base pairs
        (B) TYPE: nucleic acid
        (C) STRANDEDNESS: both
        (D) TOPOLOGY: Not Relevant (ii) MOLECULE TYPE: DNA (genomic)

(vi) ORIGINAL SOURCE:
        (B) STRAIN: XhoI/BamHI linker (xi) SEQUENCE DESCRIPTION: SEQ ID NO:112:

CCATGGATCT GCTCGAG                                                                                              17

(2) INFORMATION FOR SEQ ID NO:113:

(i) SEQUENCE CHARACTERISTICS:
        (A) LENGTH: 10 base pairs
        (B) TYPE: nucleic acid
        (C) STRANDEDNESS: both
        (D) TOPOLOGY: Not Relevant (ii) MOLECULE TYPE: DNA (genomic)

(vi) ORIGINAL SOURCE:
        (B) STRAIN: BamHI linker (xi) SEQUENCE DESCRIPTION: SEQ ID NO:113:

CCATGGATCC                                                                                                      10